United States Patent
Diem et al.

(10) Patent No.: US 11,421,035 B2
(45) Date of Patent: Aug. 23, 2022

(54) STABLE ANTIBODY VARIABLE DOMAIN FRAMEWORK COMBINATIONS AND METHODS OF USE THEREOF

(71) Applicant: Numab Therapeutics AG, Wädenswil (CH)

(72) Inventors: Dania Diem, Eschenbach (CH); Christian Hess, Zurich (CH); Sebastian Meyer, Eggenwil (CH); David Urech, Jona (CH)

(73) Assignee: Numab Therapeutics AG, Waedenswil (CH)

( * ) Notice: Subject to any disclaimer, the term of this patent is extended or adjusted under 35 U.S.C. 154(b) by 89 days.

(21) Appl. No.: 16/648,588

(22) PCT Filed: Sep. 19, 2018

(86) PCT No.: PCT/EP2018/075377
§ 371 (c)(1),
(2) Date: Mar. 18, 2020

(87) PCT Pub. No.: WO2019/057787
PCT Pub. Date: Mar. 28, 2019

(65) Prior Publication Data
US 2020/0255533 A1    Aug. 13, 2020

(30) Foreign Application Priority Data
Sep. 20, 2017    (EP) .................................... 17192206

(51) Int. Cl.
*A61K 39/00*    (2006.01)
*C07K 16/28*    (2006.01)
*C07K 16/24*    (2006.01)

(52) U.S. Cl.
CPC ........ *C07K 16/2866* (2013.01); *C07K 16/241* (2013.01); *A61K 2039/505* (2013.01); *C07K 2317/24* (2013.01); *C07K 2317/515* (2013.01); *C07K 2317/565* (2013.01); *C07K 2317/92* (2013.01); *C07K 2317/94* (2013.01)

(58) Field of Classification Search
CPC .............. C07K 16/241; C07K 16/2866; C07K 2317/24; C07K 2317/515; C07K 2317/565; C07K 2317/92; C07K 2317/94; A61K 2039/505
See application file for complete search history.

(56) References Cited

FOREIGN PATENT DOCUMENTS

| WO | WO-9708320 A1 * | 3/1997 | ............. C07K 1/047 |
|---|---|---|---|
| WO | 2007/076524 A2 | 7/2007 | |
| WO | 2014/206561 A1 | 12/2014 | |

OTHER PUBLICATIONS

International Search Report and Written Opinion, International Application No. PCT/EP2018/075377.
Kim et al., "Antibody light chain variable domains and their biophysically improved versions for human immunotherapy", MABS, 6(1) (Jan. 20, 2014) pp. 219-235.

* cited by examiner

*Primary Examiner* — Robert S Landsman
(74) *Attorney, Agent, or Firm* — Prismatic Law Group PLLC; Ron Kamis

(57) ABSTRACT

The present invention relates to novel antibody variable domain combinations with advantageous properties.

28 Claims, 6 Drawing Sheets

Specification includes a Sequence Listing.

Figure 1:

|  | Variable heavy consensus domains | | | | | | | |
|---|---|---|---|---|---|---|---|---|
|  | VH1A | VH1B | VH2 | VH3 | VH4 | VH5 | VH6 | |
| Vk1 | Vk1/VH1A | Vk1/VH1B | Vk1/VH2 | Vk1/VH3 | Vk1/VH4 | Vk1/VH5 | Vk1/VH6 | λ-capped |
| Vk2 | Vk2/VH1A | Vk2/VH1B | Vk2/VH2 | Vk2/VH3 | Vk2/VH4 | Vk2/VH5 | Vk2/VH6 | |
| Vk3 | Vk3/VH1A | Vk3/VH1B | Vk3/VH2 | Vk3/VH3 | Vk3/VH4 | Vk3/VH5 | Vk3/VH6 | |
| Vk1 | Vk1/VH1A | Vk1/VH1B | Vk1/VH2 | Vk1/VH3 | Vk1/VH4 | Vk1/VH5 | Vk1/VH6 | uncapped |
| Vk2 | Vk2/VH1A | Vk2/VH1B | Vk2/VH2 | Vk2/VH3 | Vk2/VH4 | Vk2/VH5 | Vk2/VH6 | |
| Vk3 | Vk3/VH1A | Vk3/VH1B | Vk3/VH2 | Vk3/VH3 | Vk3/VH4 | Vk3/VH5 | Vk3/VH6 | |

Variable light consensus domains

STABLE ANTIBODY VARIABLE DOMAIN FRAMEWORK COMBINATIONS AND METHODS OF USE THEREOF

CROSS-REFERENCE TO RELATED APPLICATIONS

This application is a 371 National Phase of International Patent Application No. PCT/EP2018/075377 filed on Sep. 19, 2018, which claims priority to EP 17192206.5 filed on Sep. 20, 2017, the content of each of which applications is incorporated herein by reference.

INCORPORATION OF SEQUENCE LISTING

This application contains a sequence listing submitted electronically via EFS-web, which serves as both the paper copy and the computer readable form (CRF) and consists of a file entitled "WRN14NP_seqlist2.txt", which was created on Mar. 15, 2022, which is 43,883 bytes in size, and which is herein incorporated by reference in its entirety.

FIELD OF THE INVENTION

The present invention relates to novel antibody variable domain combinations with advantageous properties.

BACKGROUND OF THE INVENTION

This invention relates to novel combinations of human antibody heavy chain domains with chimeric human antibody light chain frameworks, comprising framework regions I to III from Vκ and framework region IV from Vλ, with advantageous properties, such as high stability, reduced aggregation propensity, and improved binding affinity.

In the past forty years since the development of the first monoclonal antibodies ("mAbs"; Köhler & Milstein, Nature, 256 (1975) 495-7), antibodies have become an increasingly important class of biomolecules for research, diagnostic and therapeutic purposes. Initially, antibodies were exclusively obtained by immunizing animals with the corresponding antigen of interest. While antibodies of non-human origin can be used in research and diagnostics, in therapeutic approaches the human body may recognize non-human antibodies as foreign and raise an immune response against the non-human antibody drug substance, rendering it less or not effective. Thus, recombinant methods have been set up to render non-human antibodies less immunogenic.

Initial efforts to convert non-human mAbs into less immunogenic therapeutics entailed the engineering of chimeric antibodies consisting of animal (for example rodent) variable domains and human constant regions (Boulianne et al., Nature 312, (1984) 643-646). Further approaches aimed at the humanization of the rodent mAbs by introducing the complementarity-determining regions (CDRs) in human variable domain scaffolds (Jones et al., Nature 321 (1986) 522-525; Riechmann et al., Nature 332 (1988) 323-7) or by resurfacing the variable domains (Roguska et al., Proc. Natl. Acad. Sci. USA 91 (1994) 969-973).

For the humanization by CDR loop grafting a human acceptor framework is either chosen based on homology to the donor framework (e.g. Roguska et al., Protein Engineering 9 (1996) 895-904; WO 2008/144757 (for rabbits)) or based on a preferred stability profile (Ewert et al., Methods 34 (2004) 184-199). The latter concept has been utilized for the humanization of rabbit antibodies onto a universal variable domain framework (U.S. Pat. No. 8,193,235).

With any chosen approach the resulting mAb or functional fragment ideally retains the desired pharmacodynamic properties of the donor mAb, while displaying drug-like biophysical properties and minimal immunogenicity. With respect to the biophysical properties of mAbs or functional fragments thereof, the propensity for aggregation has been a major concern for the developability of therapeutic molecules, mainly for the following three reasons:

First, protein aggregates generally show a higher potential to elicit an immune reaction in the host leading to the formation of anti-drug antibodies and eventually to drug neutralizing antibodies (Joubert et al., J. Biol. Chem. 287 (2012) 25266-25279).

Second, aggregates affect the manufacturing yield due to the increased effort for their removal (Cromwell et al., AAPS Journal 8 (2006), Article 66).

Third, off-target effects may be observed. The concern about oligomer formation is even more pronounced for applications where monovalent binding is preferred, including bispecific (or multi-specific) antibody formats with only one valency per target and construct, because oligomer formation in these cases results in protein conglomerates with multivalent binding properties potentially leading to off-target effects. An example for such unspecific activities is the use of a construct with a single CD3ε-binding domain in a bispecific antibody format. Such a format may for example bind with one of its two binding domains to a cancer antigen and with its second, CD3ε-binding domain recruiting cytotoxic T cells. Because cross-linking of the monovalent CD3ε-binding moiety is required to induce signaling through CD3ε, T cells will only be stimulated when engaged by multiple bispecific constructs bound to the surface of the target cell—and therefore adopting the properties of a cross-linked molecule—resulting in a specific T cell response that is exclusively directed towards the cancer cell. On the contrary, oligomers of such a construct would exhibit the properties of a cross-linked bispecific antibody and therefore activate cytotoxic T cells, even when not bound to cancer cells, thereby leading to systemic activation of T cells. Such unspecific and systemic activation of T cells could result is elevated cytokine levels leading to adverse effects.

Antibody stability is in addition of crucial importance for production, purification, shelf-life and, as a consequence, the cost of goods for antibody therapeutics. Even minor improvements in one or more of these parameters may be highly relevant for the question of whether research and development of an antibody drug are going to be commercially viable.

Furthermore, a reliable and universally applicable acceptor framework is beneficial to enable a robust method of humanizing non-human antibodies, since cloning, expression and purification methods may be standardized.

To meet the above mentioned criteria for the humanization of non-human mAbs the published methodology proposes the use of human consensus variable domain framework sequences as acceptor scaffold for the engraftment of non-human complementarity determining regions. Based on the assumption that for each amino acid position in a protein, residues that contribute to protein stability have been enriched in the pool of germline sequences during evolution, it is the common understanding that the closer the resulting humanized variable domains are to the human germline consensus sequence of the respective variable domain family, the higher is the expected stability. This concept as described by Steipe (Steipe et al., J. Mol. Biol. 240 (1994) 188-92) and reviewed by Wörn (Wörn et al., J. Mol. Biol. 305 (2001) 989-1010) is widely accepted and finds wide-ranging application. Non-limiting examples are (a) the use of consensus sequence variable domains for the humanization of non-human antibodies (Carter et al., Proc. Natl. Acad. Sci. USA 89 (1992) 4285-4289); (b) the use of consensus sequence variable domains to construct CDR libraries for in vitro screening of stable target-binding antibodies (Knappik et al., J. Mol. Biol. 296 (2000) 57-86); and (c) knowledge-based approaches to improve stability of antibody variable domains by exchanging non-consensus residues into consensus residues (Steipe et al., J Mol Biol, 240 (1994), 188-92).

In addition, stabilities of the different variable domain families are described with VH3 being the most stable variable heavy domain. Importantly, in case of the variable light chain domains the Vκ family rather than the Vλ family is preferred (Ewert et al., J Mol Biol, 325 (2003) 531-53). In particular, the human consensus sequences of VH3 and Vκ1 have been described as having favorable biophysical properties (Ewert et al., J Mol Biol, 325 (2003) 531-53) and as being particularly suitable for the humanization of antibodies from non-human sources (use in Carter et al., Proc. Natl. Acad. Sci. USA 89 (1992) 4285-4289.).

In line with this there are several publications, in which the human Vκ1-VH3 consensus framework hu-4D5 has been used for the humanization of rodent and rabbit antibodies (Rader, J. Biol. Chem. 275 (2000) 13668-13676; WO 2005/016950; WO 2008/004834). Alternatively, a combination of VH and VL sequences belonging to the same families as those of hu-4D5, which sequences had originally been obtained from a recombinantly cloned immune repertoire, has been used to generate stable humanized single-chain (scFv) fragments from rabbit origin (U.S. Pat. No. 8,293, 235; Borras et al., J. Biol. Chem. 285 (2010) 9054-9066).

In order to further optimize such frameworks, it had been identified that chimeric human antibody light chain domains, comprising framework regions I to III from Vκ light chains and a framework region IV from Vλ light chains have advantageous properties, such as high stability and reduced aggregation propensity (WO 2014/206561).

For certain rabbit antibodies, however, the use of the Vκ1/VH3 combination was associated with significant loss in antigen binding affinity of the humanized variable domain, which required the engraftment of donor framework positions. Although the overall homology of Vκ1/VH3 combination to rabbit variable domains appears maximal, it cannot be excluded that other combinations would better support the engraftment of rabbit CDRs.

Thus, despite that fact that many attempts have already been made to address the issue of obtaining humanized antibody drug substances from non-human antibodies, there still remains a large unmet need to develop novel human antibody domains or combinations of antibody domains with advantageous properties, such as high stability, reduced aggregation propensity and improved affinity, wherein the human antibody frameworks contain as few mutations as possible, ideally none, when compared to naturally occurring sequences, in order to reduce the risk of creating immunogenic sequences as far as possible. Such stable human frameworks could also be used to stabilize fully human antibodies or fragments thereof for example by loop grafting or simply by exchanging the stability-contributing component between the parent antibody and the stable framework.

The solution for this problem that has been provided by the present invention, i.e. novel combinations of VH domains with chimeric human antibody light chain domains, comprising framework regions I to III from Vκ and a framework region IV from Vλ, with advantageous properties, such as high stability, reduced aggregation propensity and improved affinity, has so far not been achieved or suggested by the prior art.

SUMMARY OF THE INVENTION

The present invention relates to novel combinations of certain VH domains with certain chimeric human antibody light chain domains, comprising framework regions I to III from Vκ and a framework region IV from Vλ, with advantageous properties, such as high stability, reduced aggregation propensity, minimal immunogenic potential, and improved affinity.

Thus, in a first aspect, the present invention relates to an antibody or functional fragment thereof comprising:
(a) a variable light chain,
   wherein the variable light chain comprises, from N-terminus to C-terminus, the regions LFW1-LCDR1-LFW2-LCDR2-LFW3-LCDR3-LFW4, wherein each LFW designates a light chain framework region, and each LCDR designates a light chain complementarity-determining region, and wherein:
   (i) said LFW1, LFW2, and LFW3 regions together exhibit at least 80% sequence identity, preferably at least 95% sequence identity, to the corresponding framework regions taken from the Vκ1 sequence according to SEQ ID NO: 41; or to the corresponding framework regions taken from the Vκ3 sequence according to SEQ ID NO: 51;
   and
   (ii) said LFW4 is a Vλ-based sequence and is at least 90% identical to SEQ ID NO: 63, preferably said LFW4 is as set forth in SEQ ID NO: 63, SEQ ID NO: 79 or SEQ ID NO: 80, more preferably said LFW4 is as set forth in SEQ ID NO: 63;
and
(b) a variable heavy chain,
   wherein the variable heavy chain comprises, from N-terminus to C-terminus, the regions HFW1-HCDR1-HFW2-HCDR2-HFW3-HCDR3-HFW4, wherein each HFW designates a heavy chain framework region, and each HCDR designates a heavy chain complementarity-determining region, and
   wherein said HFW1, HFW2, and HFW3 regions together exhibit at least 82% sequence identity to the corresponding framework regions taken from the VH4 sequence according to SEQ ID NO: 21, or at least 75% sequence identity to the corresponding framework regions taken from the VH1A sequence according to SEQ ID NO: 1.

In an alternative aspect, the present invention relates to an antibody or functional fragment thereof comprising:
(a) a variable light chain,
   wherein the variable light chain comprises, from N-terminus to C-terminus, the regions LFW1-LCDR1-LFW2-LCDR2-LFW3-LCDR3-LFW4, wherein each LFW designates a light chain framework region, and each LCDR designates a light chain complementarity-determining region, and wherein:
   (iii) said LFW1, LFW2, and LFW3 regions together exhibit at least 80% sequence identity, preferably at least 95% sequence identity, to the corresponding framework regions taken from the Vκ1 sequence according to SEQ ID NO: 41; or to the corresponding framework regions taken from the Vκ3 sequence according to SEQ ID NO: 51;
and
(iv) said LFW4 is a Vλ-based sequence and is at least 90% identical to SEQ ID NO: 63, preferably said LFW4 is as set forth in SEQ ID NO: 63, SEQ ID NO: 79 or SEQ ID NO: 80, more preferably said LFW4 is as set forth in SEQ ID NO: 63;
and
(b) a variable heavy chain,
wherein the variable heavy chain comprises, from N-terminus to C-terminus, the regions HFW1-HCDR1-HFW2-HCDR2-HFW3-HCDR3-HFW4, wherein each HFW designates a heavy chain framework region, and each HCDR designates a heavy chain complementarity-determining region, and
wherein said HFW1, HFW2, HFW3, and HFW4 regions together exhibit at least 85% sequence identity, preferably at least 95% sequence identity, to the corresponding framework regions taken from the VH4 sequence according to SEQ ID NO: 21, or to the corresponding framework regions taken from the VH1A sequence according to SEQ ID NO: 1.

In a second aspect, the present invention relates to a pharmaceutical composition comprising the antibody or functional fragment thereof of the present invention, and optionally a pharmaceutically acceptable carrier and/or excipient.

In a third aspect, the present invention relates to a nucleic acid sequence or a collection of nucleic acid sequences encoding the antibody or functional fragment thereof of the present invention.

In a fourth aspect, the present invention relates to a vector or a collection of vectors comprising the nucleic acid sequence or the collection of nucleic acid sequences of the present invention.

In a fifth aspect, the present invention relates to a host cell, particularly an expression host cell, comprising the nucleic acid sequence or the collection of nucleic acid sequences of the present invention, or the vector or collection of vectors of the present invention.

In a sixth aspect, the present invention relates to a method for producing the antibody or functional fragment thereof of the present invention, comprising the step of expressing the nucleic acid sequence or the collection of nucleic acid sequences of the present invention, or the vector or collection of vectors of the present invention, or the host cell, particularly the expression host cell, of the present invention.

In a seventh aspect, the present invention relates to a method for humanizing a non-human antibody, particularly a rabbit or rodent antibody, comprising the step of:
(a) cloning, in one or more steps, nucleic acid sequences encoding variable heavy chain (VH) CDRs and variable light chain (VL) CDRs of said non-human antibody into one or more nucleic acid sequences encoding the antibody or functional fragment thereof according to the present invention, provided that at least the VH CDR3 and the VL CDR3 of said non-human antibody are cloned.

In an eighth aspect, the present invention relates to a method for optimizing a parental antibody of interest, comprising the step of:
(a) cloning, in one or more steps, nucleic acid sequences encoding VH CDRs and VL CDRs of said parental antibody into one or more nucleic acid sequences encoding the antibody or functional fragment thereof according to the present invention, provided that at least the VH CDR3 and the VL CDR3 of said parental antibody are cloned.

In a ninth aspect, the present invention relates to a method of generating a diverse collection of antibodies or functional fragments thereof, comprising the step of:
(a) cloning, in one or more steps, one or more diverse collections of nucleic acid sequences encoding one or more diverse collections of VH CDRs and/or VL CDRs into one or more nucleic acid sequences encoding the antibody or functional fragment thereof according to the present invention.

BRIEF DESCRIPTION OF THE DRAWINGS

FIG. 1 shows that Vκ1, Vκ2 and Vκ3 consensus variable light chains either λ-capped (upper half) or uncapped (i. e. comprising a Vκ framework IV; lower half, grey) were combined with VH1A, VH1B, VH2, VH3, VH4, VH5 and VH6 consensus variable heavy domains leading to 42 constructs investigated in this study.

DETAILED DESCRIPTION OF THE INVENTION

Figure 2:
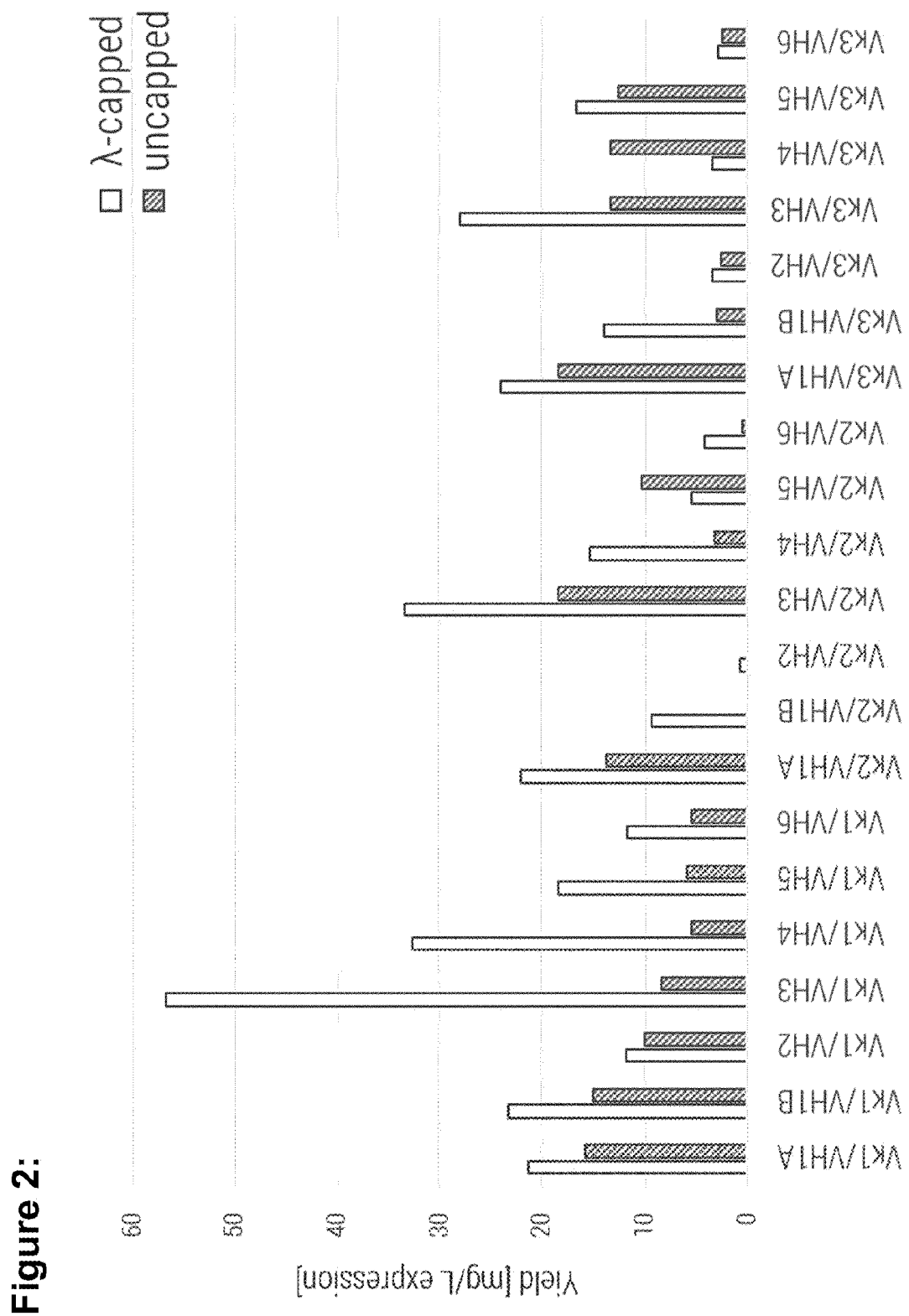
FIG. 2 shows the expression yield of capped (white bars) framework variants in comparison with their uncapped (grey bars) counterparts.

The present disclosure relates to antibodies and fragments thereof comprising novel combinations of certain VH domains with certain chimeric human antibody light chain domains, comprising framework regions I to III from Vκ and a framework region IV from Vλ, with advantageous properties, such as high stability, reduced aggregation propensity, minimal immunogenic potential, and improved affinity. It has been surprisingly found that human variable VL/VH consensus framework combinations comprising combinatorial pairs of humanized consensus (i) framework regions I to III from Vκ1 or Vκ3 light chain, and (ii) a framework region IV from Vλ light chain, and (iii) VH1A, VH1B or VH4 heavy chain domains exhibit at least similar or even superior biophysical properties compared to Vκ1/VH3 (capped or uncapped) while fully retaining the specificity and antigen-binding affinity. The inventors further demonstrated that introducing two mutations at specific framework positions (T24K and T84S) of VH4 not only improved biophysical properties, but also improved affinity. Moreover, the inventors demonstrated for the first time that, in addition to the selection of the optimal VH and VL framework combination, also the incorporation of a specific λ-cap (sk17, SEQ ID NO: 63) into VL consensus domain leads to further improvement of biophysical properties of the respective antibody or functional fragment thereof. It has been surprisingly found that sk17 containing antibody has not only improved storage and thermal stability, but also improved affinity.

Thus, in a first aspect, the present invention relates to an antibody or functional fragment thereof comprising:
(a) a variable light chain,
   wherein the variable light chain comprises, from N-terminus to C-terminus, the regions LFW1-LCDR1-LFW2-LCDR2-LFW3-LCDR3-LFW4, wherein each LFW designates a light chain framework region, and each LCDR designates a light chain complementarity-determining region, and wherein:
   (i) said LFW1, LFW2, and LFW3 regions together exhibit at least 80% sequence identity, preferably at least 95% sequence identity to the corresponding framework regions taken from the Vκ1 sequence according to SEQ ID NO: 41; or to the corresponding framework regions taken from the Vκ3 sequence according to SEQ ID NO: 51; and
   (ii) said LFW4 is a Vλ-based sequence which is at least 90% identical to SEQ ID NO: 63, preferably said LFW4 is as set forth in SEQ ID NO: 63, SEQ ID NO: 79 or SEQ ID NO: 80, more preferably said LFW4 is as set forth in SEQ ID NO: 63;
and
(b) a variable heavy chain,
   wherein the variable heavy chain comprises, from N-terminus to C-terminus, the regions HFW1-HCDR1-HFW2-HCDR2-HFW3-HCDR3-HFW4, wherein each HFW designates a heavy chain framework region, and each HCDR designates a heavy chain complementarity-determining region, and
   wherein said HFW1, HFW2, and HFW3 regions together exhibit at least 82% sequence identity to the corresponding framework regions taken from the VH4 sequence according to SEQ ID NO: 21, or at least 75% sequence identity to the corresponding framework regions taken from the VH1A sequence according to SEQ ID NO: 1.

According to the present disclosure, the framework regions taken from the Vκ1 sequence according to SEQ ID NO: 41 are LFW1', LFW2', LFW3' and LFW4' as set out in SEQ ID NOs: 42, 43, 44 and 45, respectively. The framework regions taken from the Vκ3 sequence according to SEQ ID NO: 51 are LFW1', LFW2', LFW3' and LFW4' as set out in SEQ ID NOs: 52, 53, 54 and 55, respectively. The framework regions taken from the VH4 sequence according to SEQ ID NO: 21 are HFW1', HFW2', HFW3' and HFW4' as set out in SEQ ID NOs: 22, 23, 24 and 25, respectively. The framework regions taken from the VH4 sequence according to SEQ ID NO: 26 are HFW1', HFW2', HFW3' and HFW4' as set out in SEQ ID NOs: 27, 28, 29 and 30, respectively. The framework regions taken from the VH1A sequence according to SEQ ID NO: 1 are HFW1', HFW2', HFW3' and HFW4' as set out in SEQ ID NOs: 2, 3, 4 and 5, respectively. The framework regions taken from the VH1B sequence according to SEQ ID NO: 6 are HFW1', HFW2', HFW3' and HFW4' as set out in SEQ ID NOs: 7, 8, 9 and 10, respectively.

In particular embodiments of such aspect, the HFW4 region has (i) a sequence comprised in a human heavy chain germline J segment, or (ii) a sequence comprised in a rearranged human VH sequence. In particular embodiments, the HFW4 sequence is WGQGTLVTVSS, or a sequence that exhibits at least 70%, at least 80%, or at least 90% sequence identity to WGQGTLVTVSS.

In an alternative aspect, the present invention relates to an antibody or functional fragment thereof comprising:
(a) a variable light chain,
   wherein the variable light chain comprises, from N-terminus to C-terminus, the regions LFW1-LCDR1-LFW2-LCDR2-LFW3-LCDR3-LFW4, wherein each LFW designates a light chain framework region, and each LCDR designates a light chain complementarity-determining region, and wherein:
   (v) said LFW1, LFW2, and LFW3 regions together exhibit at least 80% sequence identity, preferably at least 95% sequence identity, to the corresponding framework regions taken from the Vκ1 sequence according to SEQ ID NO: 41; or to the corresponding framework regions taken from the Vκ3 sequence according to SEQ ID NO: 51;
   and
   (vi) said LFW4 is a Vλ-based sequence and is at least 90% identical to SEQ ID NO: 63, preferably said LFW4 is as set forth in SEQ ID NO: 63, SEQ ID NO: 79 or SEQ ID NO: 80, more preferably said LFW4 is as set forth in SEQ ID NO: 63;
and
(b) a variable heavy chain,
   wherein the variable heavy chain comprises, from N-terminus to C-terminus, the regions HFW1-HCDR1-HFW2-HCDR2-HFW3-HCDR3-HFW4, wherein each HFW designates a heavy chain framework region, and each HCDR designates a heavy chain complementarity-determining region, and
   wherein said HFW1, HFW2, HFW3, and HFW4 regions together exhibit at least 85% sequence identity, preferably at least 95% sequence identity, to the corresponding framework regions taken from the VH4 sequence according to SEQ ID NO: 21, or to the corresponding framework regions taken from the VH1A sequence according to SEQ ID NO: 1.

In one embodiment, the present invention relates to an antibody or functional fragment thereof comprising:
(a) a variable light chain,
   wherein the variable light chain comprises, from N-terminus to C-terminus, the regions LFW1-LCDR1-LFW2-LCDR2-LFW3-LCDR3-LFW4 regions, wherein each LFW designates a light chain framework region, and each LCDR designates a light chain complementarity-determining region, and wherein:
   (i) said LFW1, LFW2, and LFW3 regions together exhibit at least 80% sequence identity, preferably at least 95% sequence identity, e.g., at least 97%, and, optionally, at least 86%, preferably at least 90%, more preferably at least 96%, sequence similarity to the corresponding framework regions taken from the Vκ1 sequence according to SEQ ID NO: 41; or to the corresponding framework regions taken from the Vκ3 sequence according to SEQ ID NO: 51; and (ii) said LFW4 is a Vλ-based sequence and is at least 90% identical to SEQ ID NO: 63, preferably said LFW4 is as set forth in SEQ ID NO: 63, SEQ ID NO: 79 or SEQ ID NO: 80, more preferably said LFW4 is as set forth in SEQ ID NO: 63; and (b) a variable heavy chain
wherein the variable heavy chain comprises, from N-terminus to C-terminus, the regions HFW1-HCDR1-HFW2-HCDR2-HFW3-HCDR3-HFW4, wherein each HFW designates a heavy chain framework region, and each HCDR designates a heavy chain complementarity-determining region, and
wherein said HFW1, HFW2, and HFW3 regions together exhibit
  (i) at least 75%, at least 80%, at least 85%, at least 90%, at least 95%, at least 97%, preferably at least 90%, more preferably at least 95%, sequence identity and, optionally, at least 85%, e.g. at least 90%, at least 95%, at least 96%, preferably at least 90%, more preferably at least 96%, sequence similarity to the corresponding framework regions taken from the VH1A sequence according to SEQ ID NO: 1; or
  (ii) at least 75%, at least 80%, at least 85%, at least 90%, at least 95%, at least 97%, preferably at least 90%, more preferably at least 95%, sequence identity and, optionally, at least 85%, e.g. at least 90%, at least 93%, at least 96%, preferably at least 93%, more preferably at least 96%, sequence similarity to the corresponding framework regions taken from the VH1B sequence according to SEQ ID NO: 6; or
  (iii) at least 82%, at least 85%, at least 90%, at least 95%, at least 97%, preferably at least 90%, more preferably at least 95%, sequence identity and, optionally, at least 90%, preferably at least 95%, sequence similarity to the corresponding framework regions taken from the VH4 sequence according to SEQ ID NO: 21.

In particular such embodiments, the HFW4 region has (i) a sequence comprised in a human heavy chain germline J segment, or (ii) a sequence comprised in a rearranged human VH sequence. In particular embodiments, the HFW4 sequence is WGQGTLVTVSS, or a sequence that exhibits at least 70%, at least 80%, or at least 90% sequence identity to WGQGTLVTVSS.

In an alternative embodiment, said HFW1, HFW2, HFW3, and HFW4 regions together exhibit
  (iv) at least 85%, at least 90%, at least 95%, at least 97%, preferably at least 95%, more preferably at least 97%, sequence identity and, optionally, at least 90%, e.g. at least 90%, at least 95%, at least 96%, preferably at least 95%, more preferably at least 96%, sequence similarity to the corresponding framework regions taken from the VH1A sequence according to SEQ ID NO: 1; or
  (v) at least 85%, at least 90%, at least 95%, at least 97%, preferably at least 90%, more preferably at least 95%, sequence identity and, optionally, at least 90%, preferably at least 93%, more preferably at least 96%, sequence similarity to the corresponding framework regions taken from the VH1B sequence according to SEQ ID NO: 6; or
  (vi) at least 85%, at least 90%, at least 95%, at least 97%, preferably at least 90%, more preferably at least 95%, sequence identity and, optionally, at least 90%, preferably at least 95%, sequence similarity to the corresponding framework regions taken from the VH4 sequence according to SEQ ID NO: 21.

In the context of the present invention, the term "antibody" is used as a synonym for "immunoglobulin" (Ig), which is defined as a protein belonging to the class IgG, IgM, IgE, IgA, IgY or IgD (or any subclass thereof), and includes all conventionally known antibodies. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FWs). Each VH and VL is composed of three CDRs and four FWs arranged from amino-terminus to carboxy-terminus in the following order: FW1-CDR1-FW2-CDR2-FW3-CDR3-FW4. The variable regions of the heavy and light chains contain a binding domain that interacts with an antigen.

The term "antibody fragment" refers to at least one portion of an intact antibody, or recombinant variants thereof, and the term "functional fragment" or "functional antibody fragment" refers an antibody fragment comprising at least an antigen binding domain, e.g., an antigenic determining variable region of an intact antibody, that is sufficient to confer recognition and specific binding of the functional antibody fragment to a target, such as an antigen. Examples of functional antibody fragments include, but are not limited to, Fab, Fab', F(ab')2, and Fv fragments, scFv antibody fragments, linear antibodies, single domain antibodies such as sdAb (either VL or VH), camelid VHH domains, and multi-specific molecules formed from antibody fragments such as a bivalent fragment comprising two or more, e.g., two, Fab fragments linked by a disulfide bridge at the hinge region, or two or more, e.g., two isolated CDR or other epitope binding fragments of an antibody linked. An antibody fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antibody fragments can also be grafted into scaffolds based on polypeptides such as a fibronectin type III (Fn3) (see U.S. Pat. No. 6,703,199, which describes fibronectin polypeptide minibodies). An "antigen-binding region" or "antigen-binding domain" of an antibody typically is found in one or more hypervariable region(s) of an antibody, i.e., the CDR1, CDR2, and/or CDR3 regions; however, the variable "framework" regions can also play an important role in antigen binding, such as by providing a scaffold for the CDRs. The constant regions of the antibodies may mediate the binding of the immunoglobulin to host tissues or factors, including various cells of the immune system (e.g., effector cells) and the first component (Clq) of the classical complement system. The term "antibody" includes for example, monoclonal antibodies, human antibodies, humanized antibodies, camelid antibodies, or chimeric antibodies. The antibodies can be of any isotype (e.g., IgG, IgE, IgM, IgD, IgA and IgY), class (e.g., IgG1, IgG2, IgG3, IgG4, IgA1 and IgA2) or subclass.

The "Complementarity Determining Regions" ("CDRs") are amino acid sequences with boundaries determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme) and ImMunoGenTics (IMGT) numbering (Lefranc, M.-P., The Immunologist, 7, 132-136 (1999); Lefranc, M.-P. et al., Dev. Comp. Immunol., 27, 55-77 (2003) ("IMGT" numbering scheme). For example, for classic formats, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 24-34 (LCDR1), 50-56 (LCDR2), and 89-97 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL. Under IMGT the CDR amino acid residues in the VH are numbered approximately 26-35 (HCDR1), 51-57 (HCDR2) and 93-102 (HCDR3), and the CDR amino acid residues in the VL are numbered approximately 27-32 (LCDR1), 50-52 (LCDR2), and 89-97 (LCDR3) (numbering according to "Kabat"). Under IMGT, the CDRs of an antibody can be determined using the program IMGT/DomainGap Align.

In the context of the present invention, the numbering system suggested by Honegger & Plückthun is used (Honegger & Plückthun, J. Mol. Biol. 309 (2001) 657-670), unless specifically mentioned otherwise. Furthermore, the following residues are defined as CDRs (according to AHo numbering scheme): LCDR1 (also referred to as CDR-L1): L24-L42; LCDR2 (also referred to as CDR-L2): L58-L72; LCDR3 (also referred to as CDR-L3): L107-L138; HCDR1 (also referred to as CDR-H1): H27-H42; HCDR2 (also referred to as CDR-H2): H57-H76; HCDR3 (also referred to as CDR-H3): H108-H138. For the sake of clarity, the numbering system according to Honegger & Plückthun takes the length diversity into account that is found in naturally occurring antibodies, both in the different VH and VL subfamilies and, in particular, in the CDRs, and provides for gaps in the sequences. Thus, in a given antibody variable domain usually not all positions 1 to 149 will be occupied by an amino acid residue. For the sake of clarity, the framework regions according to the numbering system according to Honegger & Plückthun are: in the case of the variable light chain, LFW1 (or VL framework region I): L1-L23; LFW2 (or VL framework region II): L43-L57; LFW3 (or VL framework region III): L73-L106; and LFW4 (or VL framework region IV): L139-L149; and, in the case of the variable heavy chain, HFW1 (or VH framework region I): L1-L26; HFW2 (or VH framework region II): L43-L56; HFW3 (or VH framework region III): L77-L107; and HFW4 (or VH framework region IV): L139-L149.

Preferably, the "antigen-binding region" comprises at least amino acid residues 4 to 149 of the variable light (VL) chain and 5 to 144 of the variable heavy (VH) chain (in each case numbering according to Honegger & Plückthun), more preferably amino acid residues 3 to 149 of VL and 4 to 146 of VH, and particularly preferred are the complete VL and VH chains (amino acid positions 1 to 149 of VL and 1 to 149 of VH). The framework regions and CDRs are indicated in Table 7. A preferred class of immunoglobulins for use in the present invention is IgG. "Functional fragments" of the invention include the domain of a F(ab')$_2$ fragment, a Fab fragment, Fv and scFv. The F(ab')$_2$ or Fab may be engineered to minimize or completely remove the intermolecular disulphide interactions that occur between the CH1 and CL domains. The antibodies or functional fragments thereof of the present invention may be part of bi- or multifunctional constructs, as further described in Sections [0087] to [0091].

In the context of the present invention the terms "VH" (variable heavy chain), "Vκ" and "Vλ" refer to families of antibody heavy and light chain sequences that are grouped according to sequence identity and homology. Methods for the determination of sequence homologies, for example by using a homology search matrix such as BLOSUM (Henikoff, S. & Henikoff, J. G., Proc. Natl. Acad. Sci. USA 89 (1992) 10915-10919), and methods for the grouping of sequences according to homologies are well known to one of ordinary skill in the art. For VH, Vκ and Vλ different subfamilies can be identified, as shown, for example, in Knappik et al., J. Mol. Biol. 296 (2000) 57-86, which groups VH in VH1A, VH1B and VH2 to VH6, Vκ in Vκ1 to Vκ4 and Vλ in Vλ1 to Vλ3. In vivo, antibody Vκ chains, Vλ chains, and VH chains are the result of the random rearrangement of germline κ chain V and J segments, germline λ chain V and J segments, and heavy chain V, D and J segments, respectively. To which subfamily a given antibody variable chain belongs is determined by the corresponding V segment, and in particular by the framework regions FW1 to FW3. Thus, any VH sequence that is characterized in the present application by a particular set of framework regions HFW1 to HFW3 only, may be combined with any HFW4 sequence, for example a HFW4 sequence taken from one of the heavy chain germline J segments, or a HFW4 sequence taken from a rearranged VH sequence. In particular embodiments, the HFW4 sequence is WGQGTLVTVSS.

Suitably, the antibody or functional fragment of the present invention is an isolated antibody or functional fragment thereof. The term "isolated antibody", as used herein, means a polypeptide or a protein thereof which, by virtue of its origin or manipulation: (i) is present in a host cell as the expression product of a portion of an expression vector, or (ii) is linked to a protein or other chemical moiety other than that to which it is linked in nature, or (iii) does not occur in nature. By "isolated" it is further meant a protein that is: (i) chemically synthesized; or (ii) expressed in a host cell and purified away from associated proteins, as by gel chromatography. The term "isolated antibody" also refers to antibody that is substantially free of other antibodies having different antigenic specificities (e.g., an isolated antibody that specifically binds to IL23R is substantially free of antibodies that specifically bind antigens other than IL23R). An isolated antibody that specifically binds IL23R may, however, have cross-reactivity to other antigens, such as IL23R molecules from other species. Moreover, an isolated antibody may be substantially free of other cellular material and/or chemicals.

"Affinity" refers to the strength of the sum of total noncovalent interactions between a single binding site or a molecule, e.g., an antibody or a functional fragment thereof, and its binding partner, e.g., an antigen. Unless indicated otherwise, as used herein, "binding affinity" refers to intrinsic binding affinity which reflects 1:1 interaction between members of a binding pair, e.g., interaction of a single antibody binding domain and its antigen. The affinity can generally be represented by the dissociation constant ($K_D$). Affinity can be measured by common methods known in the art, including those described herein.

The following terms are used to describe the sequence relationships between two or more polynucleotide or amino acid sequences: "sequence identity" or "percentage of sequence identity", and "sequence similarity" or "percentage of sequence similarity". The term "sequence identity" as used herein is determined by calculating the maximum number of amino acid residues that are identical between two polypeptide sequences, wherein gaps and/or insertions may be factored in order to allow for the largest degree of sequence overlap. For example, two 100mer polypeptides that are fully identical have a sequence identity of 100%. When they differ by a single mutation, or when one polypeptide contains a deletion of one amino acid, the sequence identity is 99% (99 out of 100 positions being identical). In other words, the "percentage of sequence identity" is calculated by comparing two optimally aligned sequences over the window of comparison, determining the number of positions at which the identical nucleic acid base (e.g., A, T, C, G, U or I) or amino acid residue occurs in both sequences to yield the number of matched positions, dividing the number of matched positions by the total number of positions in the comparison window (i.e., the window size), and multiplying the result by 100 to yield the percentage of sequence identity. The "sequence similarity" is the degree of resemblance between two sequences when they are compared. Where necessary or desired, optimal alignment of sequences for comparison can be conducted, for example, by the local homology algorithm of Smith and Waterman (Adv. Appl. Math. 2:482 (1981)), by the homology alignment algorithm of Needleman and Wunsch (J. Mol. Biol. 48:443-53 (1970)), by the search for similarity method of Pearson and Lipman (Proc. Natl. Acad. Sci. USA 85:2444-48 (1988)), by computerized implementations of these algorithms (e.g., GAP, BESTFIT, FASTA, and TFASTA in the Wisconsin Genetics Software Package, Genetics Computer Group, 575 Science Dr., Madison, Wis.), or by visual inspection. (See generally Ausubel et al. (eds.), Current Protocols in Molecular Biology, 4th ed., John Wiley and Sons, New York (1999)). Unless indicated otherwise herein, the degree of sequence similarity referred to herein is determined by utilization of Dayhoff PAM matrix (M. O. Dayhoff, R. Schwartz, B.C. Orcutt: A model of Evolutionary Change in Proteins, pages 345-352; in: Atlas of protein sequence and structure, National Biomedical Research Foundation, 1979).

In one embodiment, the antibody or functional fragment of the present invention comprises a variable heavy chain comprising HFW1, HFW2, HFW3, and HFW4 regions, wherein said regions together exhibit at least 85%, at least 90%, at least 95%, at least 97%, preferably at least 95%, more preferably at least 97% sequence identity, to the corresponding framework regions taken from the VH1A sequence according to SEQ ID NO: 1. Alternatively, said HFW1, HFW2, and HFW3 regions together exhibit at least 75%, at least 80%, at least 85%, at least 90%, at least 95%, at least 97%, preferably at least 90%, more preferably at least 95% sequence identity, to the corresponding framework regions taken from the VH1A sequence according to SEQ ID NO: 1.

In a further embodiment, the antibody or functional fragment of the present invention comprises a variable heavy chain comprising HFW1, HFW2, HFW3, and HFW4 regions, wherein said regions together exhibit at least 90% sequence similarity, e.g. at least 90%, at least 93%, at least 95%, at least 96% sequence similarity, preferably at least 93% sequence similarity, more preferably at least 96% sequence similarity to the corresponding framework regions taken from the VH1A sequence according to SEQ ID NO: 1. Alternatively, said HFW1, HFW2, and HFW3 regions together exhibit at least 85% sequence similarity, e.g. at least 90%, at least 95%, at least 96% sequence similarity, preferably at least 90% sequence similarity, more preferably at least 96% sequence similarity to the corresponding framework regions taken from the VH1A sequence according to SEQ ID NO: 1.

In one embodiment, the antibody or functional fragment of the present invention comprises a variable heavy chain comprising HFW1, HFW2, HFW3, and HFW4 regions, wherein said regions together exhibit at least 85%, at least 90%, at least 95%, at least 97%, preferably at least 90%, more preferably at least 95%, sequence identity to the corresponding framework regions taken from the VH1B sequence according to SEQ ID NO: 6. Alternatively, said HFW1, HFW2, and HFW3 regions together exhibit at least 90%, at least 93%, at least 95%, at least 97%, preferably at least 93%, more preferably at least 95%, sequence identity to the corresponding framework regions taken from the VH1B sequence according to SEQ ID NO: 6.

In a further embodiment, the antibody or functional fragment of the present invention comprises a variable heavy chain comprising HFW1, HFW2, HFW3, and HFW4 regions, wherein said regions together exhibit at least 90%, preferably at least 93%, more preferably at least 96%, sequence similarity to the corresponding framework regions taken from the VH1B sequence according to SEQ ID NO: 6. Alternatively, said HFW1, HFW2, and HFW3 regions together exhibit at least 85%, preferably at least 90%, more preferably at least 96%, sequence similarity to the corresponding framework regions taken from the VH1B sequence according to SEQ ID NO: 6.

In another embodiment, the antibody or functional fragment of the present invention comprises a variable heavy chain comprising HFW1, HFW2, HFW3, and HFW4 regions, wherein said regions together exhibit at least 85%, at least 90%, at least 95%, at least 97%, sequence identity, preferably at least 90%, sequence identity to the corresponding framework regions taken from the VH4 sequence according to SEQ ID NO: 21. Alternatively, said HFW1, HFW2, and HFW3 regions together exhibit at least 82%, at least 85%, at least 90%, at least 95% or at least 97% sequence identity, preferably at least 90%, sequence identity to the corresponding framework regions taken from the VH4 sequence according to SEQ ID NO: 21. In one embodiment, the antibody or functional fragment of the present invention comprises a variable heavy chain comprising HFW1, HFW2, HFW3, and HFW4 regions, wherein said regions together exhibit at least 85%, at least 90%, at least 95%, at least 97% sequence identity, preferably at least 90%, sequence identity to the framework regions taken from the VH4 sequence according to SEQ ID NO: 21, wherein said variable heavy chain comprises two mutations T24K and T84S (see SEQ ID NO: 26). Alternatively, said HFW1, HFW2, and HFW3 regions together exhibit at least 82%, at least 85%, at least 90%, at least 95%, at least 97% sequence identity, preferably at least 90%, sequence identity to the framework regions taken from the VH4 sequence according to SEQ ID NO: 21, wherein said variable heavy chain comprises two mutations T24K and T84S (see SEQ ID NO: 26). In another embodiment, the antibody or functional fragment of the present invention comprises a variable heavy chain comprising HFW1, HFW2, HFW3, and HFW4 regions, wherein said regions together exhibit at least 85%, at least 90%, at least 95%, at least 97% sequence identity, preferably at least 90%, sequence identity to the corresponding framework regions taken from the VH4 sequence according to SEQ ID NO: 21, wherein said variable heavy chain comprises Lys at AHo position 24, and Ser at AHo position 84 (numbering according to Honegger & Plückthun). Alternatively, said HFW1, HFW2, and HFW3 regions together exhibit at least 82%, at least 85%, at least 90%, at least 95%, at least 97% sequence identity, preferably at least 90%, sequence identity to the corresponding framework regions taken from the VH4 sequence according to SEQ ID NO: 21, wherein said variable heavy chain comprises Lys at AHo position 24, and Ser at AHo position 84 (numbering according to Honegger & Plückthun).

In a further embodiment, the antibody or functional fragment of the present invention comprises a variable heavy chain comprising HFW1, HFW2, HFW3, and HFW4 regions, wherein said regions together exhibit at least 85% sequence identity, at least 90% sequence identity, at least 95%, at least 97%, preferably at least 90% sequence identity, to the corresponding framework regions taken from the VH4 sequence according to SEQ ID NO: 26, preferably wherein said variable heavy chain comprises Lys at AHo position 24, and Ser at AHo position 84 (numbering according to Honegger & Plückthun). Alternatively, said HFW1, HFW2, and HFW3 regions together exhibit at least 82% sequence identity, at least 85% sequence identity, at least 90% sequence identity, at least 95%, at least 97%, preferably at least 90% sequence identity, to the corresponding framework regions taken from the VH4 sequence according to SEQ ID NO: 26, preferably wherein said variable heavy chain comprises Lys at AHo position 24, and Ser at AHo position 84 (numbering according to Honegger & Plückthun).

In one embodiment, the antibody or functional fragment of the present invention comprises a variable heavy chain comprising HFW1, HFW2, HFW3, and HFW4 regions, wherein said regions together exhibit at least 90%, e.g. at least 95%, at least 97%, preferably at least 90%, sequence similarity to the corresponding framework regions taken from the VH4 sequence according to SEQ ID NO: 21. Alternatively, said HFW1, HFW2, and HFW3 regions together exhibit at least 90%, e.g. at least 95%, at least 97%, preferably at least 90%, sequence similarity to the corresponding framework regions taken from the VH4 sequence according to SEQ ID NO: 21. In a further embodiment, the antibody or functional fragment of the present invention comprises a variable heavy chain comprising HFW1, HFW2, HFW3, and HFW4 regions, wherein said regions together exhibit at least 90%, e.g. at least 95%, at least 97%, preferably at least 90%, sequence similarity to the corresponding framework regions taken from the VH4 sequence according to SEQ ID NO: 21, wherein said variable heavy chain comprises two mutations T24K and T84S (see SEQ ID NO: 26). Alternatively, said HFW1, HFW2, and HFW3 regions together exhibit at least 90%, e.g. at least 95%, at least 97%, preferably at least 90%, sequence similarity to the corresponding framework regions taken from the VH4 sequence according to SEQ ID NO: 21, wherein said variable heavy chain comprises two mutations T24K and T84S (see SEQ ID NO: 26). In another embodiment, the antibody or functional fragment of the present invention comprises a variable heavy chain comprising HFW1, HFW2, HFW3, and HFW4 regions, wherein said regions together exhibit at least 90%, e.g. at least 95%, at least 97%, preferably at least 90%, sequence similarity to the corresponding framework regions taken from the VH4 sequence according to SEQ ID NO: 21, wherein said variable heavy chain comprises Lys at AHo position 24, and Ser at AHo position 84 (numbering according to Honegger & Plückthun). Alternatively, said HFW1, HFW2, and HFW3 regions together exhibit at least 90%, e.g. at least 95%, at least 97%, preferably at least 90%, sequence similarity to the corresponding framework regions taken from the VH4 sequence according to SEQ ID NO: 21, wherein said variable heavy chain comprises Lys at AHo position 24, and Ser at AHo position 84 (numbering according to Honegger & Plückthun).

In a further embodiment, the antibody or functional fragment of the present invention comprises a variable heavy chain comprising HFW1, HFW2, and HFW3, and HFW4 regions, wherein said regions together exhibit at least 90% sequence similarity, e.g. at least 93%, preferably at least 96% sequence similarity, to the corresponding framework regions taken from the VH4 sequence according to SEQ ID NO: 26, preferably wherein said variable heavy chain comprises Lys at AHo position 24, and Ser at AHo position 84 (numbering according to Honegger & Plückthun). Alternatively, said HFW1, HFW2, and HFW3 regions together exhibit at least 90% sequence similarity, e.g. at least 93%, preferably at least 96% sequence similarity, to the corresponding framework regions taken from the VH4 sequence according to SEQ ID NO: 26, preferably wherein said variable heavy chain comprises Lys at AHo position 24, and Ser at AHo position 84 (numbering according to Honegger & Plückthun).

In one embodiment, the antibody or functional fragment of the present invention comprises a variable light chain comprising LFW1, LFW2, and LFW3 regions, wherein said regions together exhibit at least 80% sequence identity, e.g. at least 85%, at least 90%, at least 93%, at least 95%, at least 97% sequence identity, preferably at least 93% sequence identity, to the corresponding framework regions taken from the Vκ1 sequence according to SEQ ID NO: 41.

In a further embodiment, the antibody or functional fragment of the present invention comprises a variable light chain comprising LFW1, LFW2, and LFW3 regions, wherein said regions together exhibit at least 86%, e.g. at least 90%, at least 95%, preferably at least 96%, sequence similarity, to the corresponding framework regions taken from the Vκ1 sequence according to SEQ ID NO: 41.

In another embodiment, the antibody or functional fragment of the present invention comprises a variable light chain comprising LFW1, LFW2, and LFW3 regions, wherein said regions together exhibit at least 80% sequence identity, e.g. at least 85%, at least 90%, at least 93%, at least 95%, at least 97% sequence identity, preferably at least 93% sequence identity, to the corresponding framework regions taken from the Vκ3 sequence according to SEQ ID NO: 51.

In a further embodiment, the antibody or functional fragment of the present invention comprises a variable light chain comprising LFW1, LFW2, and LFW3 regions, wherein said regions together exhibit at least 86%, preferably at least 90%, at least 95%, at least 96% sequence similarity, preferably at least 90%, more preferably at least 96% sequence similarity, to the corresponding framework regions taken from the Vκ3 sequence according to SEQ ID NO: 51.

In one embodiment, the antibody or functional fragment of the present invention comprises a variable light chain comprises LFW4, wherein said LFW4 region is a Vλ-based sequence and is at least 90% identical to SEQ ID NO: 63. Suitably, said LFW4 region is as set forth in SEQ ID NO: 63, SEQ ID NO: 79 or SEQ ID NO: 80. In a preferred embodiment, said LFW4 region is as set forth in SEQ ID NO: 63.

Suitably, when both the antibody heavy chain and the LFW4 region of the light chain comprise a Cys-mutation, it further improves the biophysical properties of the corresponding antibody due to formation of interchain disulfide bond. In particular embodiments, the antibody heavy chain comprises the Cys-mutation G51C (numbering according to Honegger & Plückthun). In particular embodiments, said LFW4 region is as set forth in SEQ ID NO: 79 or SEQ ID NO: 80. In one embodiment, the antibody of the invention or functional fragment thereof comprises:
- (a) a variable light chain comprising a LFW4 as set forth in SEQ ID NO: 79 or SEQ ID NO: 80; and
- (b) a variable heavy chain comprising regions HFW1, HFW2, HFW3 and HFW4, wherein said HFW1, HFW2, and HFW3, and HFW4 regions together exhibit (i) at least 85% sequence identity, more preferably at least 90% sequence identity to the corresponding framework regions taken from the VH4 sequence according to SEQ ID NO: 21 or SEQ ID NO: 26; or (ii) at least 85% sequence identity, preferably at least 95% sequence identity, more preferably at least 97% sequence identity to the corresponding framework regions taken from the VH1A sequence according to SEQ ID NO: 1; or (iii) at least 85% sequence identity, preferably at least 90% sequence identity, more preferably at least 95% sequence identity to the corresponding framework regions taken from the VH1B sequence according to SEQ ID NO: 6;
  and wherein said variable heavy chain comprises Cys at AHo position 51 (numbering according to Honegger & Plückthun).

In embodiments alternative to those shown in (b) above, said HFW1, HFW2, and HFW3 regions together exhibit at least 82%, e.g. at least 85%, at least 90%, at least 95%, at least 97% sequence identity, preferably at least 90%, sequence identity and, optionally, at least 90%, e.g. at least 93%, preferably at least 95%, sequence similarity to the corresponding framework regions of the VH sequences with SEQ ID NO: 21, SEQ ID NO: 26, SEQ ID NO: 1, and SEQ ID NO: 6, respectively.

In a suitable embodiment, the antibody or functional fragment of the present invention comprises a variable light chain comprising LFW1, LFW2, LFW3, and LFW4 regions, wherein the LFW1, LFW2, and LFW3 regions together exhibit at least 80% sequence identity, e.g., at least 85%, at least 90%, at least 95%, at least 97%, preferably at least 93%, more preferably at least 95% sequence identity, to the corresponding framework regions taken from the Vκ1/sk17 sequence according to SEQ ID NO: 57. In a suitable such embodiment, the antibody or functional fragment of the present invention comprises a variable light chain comprising LFW1, LFW2, LFW3, and LFW4 regions, wherein the LFW1, LFW2, and LFW3 regions together exhibit at least 86%, at least 90%, preferably at least 95%, sequence similarity to the corresponding framework regions taken from the Vκ1/sk17 sequence according to SEQ ID NO: 57.

In a suitable embodiment, the antibody or functional fragment of the present invention comprises a variable light chain comprising LFW1, LFW2, LFW3, and LFW4 regions, wherein the LFW1, LFW2, and LFW3 regions together at least 80% sequence identity, e.g., at least 81%, at least 85%, at least 90%, at least 95%, at least 97% sequence identity, preferably at least 93%, more preferably at least 95% sequence identity, to the corresponding framework regions taken from the Vκ3/sk17 sequence according to SEQ ID NO: 61. In a suitable such embodiment, the antibody or functional fragment of the present invention comprises a variable light chain comprising LFW1, LFW2, LFW3, and LFW4 regions, wherein the LFW1, LFW2, and LFW3 regions together exhibit at least 86%, at least 90%, preferably at least 95% sequence similarity to the corresponding framework regions taken from the Vκ3/sk17 sequence according to SEQ ID NO: 61.

In a suitable embodiment, the antibody or functional fragment of the present invention comprises a variable heavy chain comprising HFW1, HFW2, and HFW3, and HFW4 regions taken from the VH1A sequence according to SEQ ID NO: 1, from the VH1B sequence according to SEQ ID NO: 6, from the VH4 sequence according to SEQ ID NO: 21, or from the VH4$_{mut}$ sequence according to SEQ ID NO: 26. Suitably, the variable heavy chain of the antibody of the invention comprises:
- (a) HFW1 as set forth in SEQ ID NO: 2, HFW2 as set forth in SEQ ID NO: 3, HFW3 as set forth in SEQ ID NO: 4, and HFW4 as set forth in SEQ ID NO: 5; or
- (b) HFW1 as set forth in SEQ ID NO: 7, HFW2 as set forth in SEQ ID NO: 8, HFW3 as set forth in SEQ ID NO: 9, and HFW4 as set forth in SEQ ID NO: 10; or
- (c) HFW1 as set forth in SEQ ID NO: 22, HFW2 as set forth in SEQ ID NO: 23, HFW3 as set forth in SEQ ID NO: 24, and HFW4 as set forth in SEQ ID NO: 25; or
- (d) HFW1 as set forth in SEQ ID NO: 27, HFW2 as set forth in SEQ ID NO: 28, HFW3 as set forth in SEQ ID NO: 29, and HFW4 as set forth in SEQ ID NO: 30.

In a suitable embodiment, the antibody or functional fragment of the present invention comprises the variable light chain comprises LFW1, LFW2, and LFW3 regions taken from the Vκ1 sequence according to SEQ ID NO: 41, or from the Vκ3 sequence according to SEQ ID NO: 51. Suitably, the variable light chain of the antibody of the invention comprises:
- (a) LFW1 as set forth in SEQ ID NO: 42, LFW2 as set forth in SEQ ID NO: 43, and LFW3 as set forth in SEQ ID NO: 44; or
- (b) LFW1 as set forth in SEQ ID NO: 52, LFW2 as set forth in SEQ ID NO: 53, and LFW3 as set forth in SEQ ID NO: 54.

In particular embodiments, said antibody or functional fragment thereof has the framework sequences as set out below:
- (a) wherein said HFW1, HFW2, HFW3, and HFW4 regions together exhibit at least 85%, e.g. at least 90%, at least 95%, at least 97% sequence identity, preferably at least 90%, sequence identity and, optionally, at least 90%, e.g. at least 93%, at least 95%, preferably at least 95%, sequence similarity to the corresponding framework regions taken from the VH4 sequence according to SEQ ID NO: 21, and wherein said LFW1, LFW2, and LFW3 regions together exhibit at least 80% sequence identity, e.g. at least 85%, at least 90%, at least 93%, at least 95%, at least 97% sequence identity, preferably at least 93% sequence identity and, optionally, at least 86%, e.g. at least 90%, at least 95%, preferably at least 96% sequence similarity to the corresponding framework regions taken from the Vκ1 sequence according to SEQ ID NO: 41, and wherein said LFW4 is a Vλ-based sequence and is at least 90% identical to SEQ ID NO: 63, preferably said LFW4 is as set forth in SEQ ID NO: 63, SEQ ID NO: 79 or SEQ ID NO: 80, more preferably said LFW4 is as set forth in SEQ ID NO: 63;
  in particular
  (i) wherein the variable heavy chain comprises HFW1 as set forth in SEQ ID NO: 22, HFW2 as set forth in SEQ ID NO: 23, HFW3 as set forth in SEQ ID NO: 24, and HFW4 as set forth in SEQ ID NO: 25; and the variable light chain comprises LFW1 as set forth in SEQ ID NO:

42, LFW2 as set forth in SEQ ID NO: 43, LFW3 as set forth in SEQ ID NO: 44, and LFW4 as set forth in SEQ ID NO: 63;

or (ii) wherein the variable heavy chain comprises HFW1 as set forth in SEQ ID NO: 27, HFW2 as set forth in SEQ ID NO: 28, HFW3 as set forth in SEQ ID NO: 29, and HFW4 as set forth in SEQ ID NO: 30; and the variable light chain comprises LFW1 as set forth in SEQ ID NO: 42, LFW2 as set forth in SEQ ID NO: 43, LFW3 as set forth in SEQ ID NO: 44, and LFW4 as set forth in SEQ ID NO: 63; or (b) wherein said HFW1, HFW2, HFW3, and HFW4 regions together exhibit at least 85%, e.g. at least 90%, at least 95%, at least 97% sequence identity, preferably at least 90%, sequence identity and, optionally, at least 90%, e.g. at least 93%, at least 95%, preferably at least 95%, sequence similarity to the corresponding framework regions taken from the VH4 sequence according to SEQ ID NO: 21, and wherein said LFW1, LFW2, and LFW3 regions together exhibit a at least 80% sequence identity, e.g. at least 85%, at least 90%, at least 93%, at least 95%, at least 97% sequence identity, preferably at least 93% sequence identity and, optionally, at least 86%, preferably at least 90% sequence similarity, at least 95%, at least 96%, preferably at least 80%, more preferably at least 96% sequence similarity to the corresponding framework regions taken from the Vκ3 sequence according to SEQ ID NO: 51, and wherein said LFW4 is a Vλ-based sequence and is at least 90% identical to SEQ ID NO: 63, preferably said LFW4 is as set forth in SEQ ID NO: 63, SEQ ID NO: 79 or SEQ ID NO: 80, more preferably said LFW4 is as set forth in SEQ ID NO: 63; in particular:

(i) wherein the variable heavy chain comprises HFW1 as set forth in SEQ ID NO: 22, HFW2 as set forth in SEQ ID NO: 23, HFW3 as set forth in SEQ ID NO: 24, and HFW4 as set forth in SEQ ID NO: 25; and the variable light chain comprises LFW1 as set forth in SEQ ID NO: 52, LFW2 as set forth in SEQ ID NO: 53, LFW3 as set forth in SEQ ID NO: 54, and LFW4 as set forth in SEQ ID NO: 63;

or (ii) wherein the variable heavy chain comprises HFW1 as set forth in SEQ ID NO: 27, HFW2 as set forth in SEQ ID NO: 28, HFW3 as set forth in SEQ ID NO: 29, and HFW4 as set forth in SEQ ID NO: 30; and the variable light chain comprises LFW1 as set forth in SEQ ID NO: 52, LFW2 as set forth in SEQ ID NO: 53, LFW3 as set forth in SEQ ID NO: 54, and LFW4 as set forth in SEQ ID NO: 63; or (c) wherein said HFW1, HFW2, HFW3, and HFW4 regions together exhibit least 85%, e.g. at least 90%, at least 95% sequence identity, at least 97%, preferably at least 90%, sequence identity and, optionally, at least 90%, e.g. at least 95%, preferably at least 95%, sequence similarity to the corresponding framework regions taken from the VH4 sequence according to SEQ ID NO: 21, and wherein said variable heavy chain comprises Lys at AHo position 24, and Ser at AHo position 84, and wherein said LFW1, LFW2, and LFW3 regions together exhibit at least 80% sequence identity, e.g. at least 85%, at least 90%, at least 93%, at least 95%, at least 97% sequence identity, preferably at least 93% sequence identity and, optionally, at least 86%, e.g. at least 90%, at least 95%, preferably at least 96% sequence similarity to the corresponding framework regions taken from the Vκ1 sequence according to SEQ ID NO: 41, and wherein said LFW4 is a Vλ-based sequence and is at least 90% identical to SEQ ID NO: 63, preferably said LFW4 is as set forth in SEQ ID NO: 63, SEQ ID NO: 79 or SEQ ID NO: 80, more preferably said LFW4 is as set forth in SEQ ID NO: 63;

in particular:

wherein the variable heavy chain comprises HFW1 as set forth in SEQ ID NO: 27, HFW2 as set forth in SEQ ID NO: 28, HFW3 as set forth in SEQ ID NO: 29, and HFW4 as set forth in SEQ ID NO: 30; and the variable light chain comprises LFW1 as set forth in SEQ ID NO: 42, LFW2 as set forth in SEQ ID NO: 43, LFW3 as set forth in SEQ ID NO: 44, and LFW4 as set forth in SEQ ID NO: 63; or (d) wherein said HFW1, HFW2, HFW3, and HFW4 regions together exhibit least 85%, e.g. at least 90%, at least 95%, at least 97% sequence identity, preferably at least 84%, sequence identity and, optionally, at least 90%, e.g. at least 93%, at least 95%, preferably at least 93%, sequence similarity to the corresponding framework regions taken from the VH4 sequence according to SEQ ID NO: 21, and wherein said variable heavy chain comprises Lys at AHo position 24, and Ser at AHo position 84, and wherein said LFW1, LFW2, and LFW3 regions together exhibit at least 80% sequence identity, e.g. at least 85%, at least 90%, at least 93%, at least 95%, at least 97% sequence identity, preferably at least 93% sequence identity and, optionally, at least 86%, preferably at least 90% sequence similarity, at least 95%, at least 96%, preferably at least 90%, more preferably at least 96% sequence similarity to the corresponding framework regions taken from the Vκ3 sequence according to SEQ ID NO: 51, and wherein said LFW4 is a Vλ-based sequence and is at least 90% identical to SEQ ID NO: 63, preferably said LFW4 is as set forth in SEQ ID NO: 63, SEQ ID NO: 79 or SEQ ID NO: 80, more preferably said LFW4 is as set forth in SEQ ID NO: 63;

in particular:

wherein the variable heavy chain comprises HFW1 as set forth in SEQ ID NO: 27, HFW2 as set forth in SEQ ID NO: 28, HFW3 as set forth in SEQ ID NO: 29, and HFW4 as set forth in SEQ ID NO: 30; and the variable light chain comprises LFW1 as set forth in SEQ ID NO: 52, LFW2 as set forth in SEQ ID NO: 53, LFW3 as set forth in SEQ ID NO: 54, and LFW4 as set forth in SEQ ID NO: 63; or (e) wherein said HFW1, HFW2, HFW3, and HFW4 regions together exhibit at least 85% sequence identity, e.g. at least 90%, at least 93%, at least 95%, at least 97% sequence identity, preferably at least 95% sequence identity, more preferably at least 97% sequence identity and, optionally, at least 90% sequence similarity, e.g. at least 93%, at least 95%, at least 96% sequence similarity, preferably at least 95% sequence similarity, more preferably at least 96% sequence similarity to the corresponding framework regions taken from the VH1A sequence according to SEQ ID NO: 1, and wherein said LFW1, LFW2, and LFW3 regions together exhibit at least 80% sequence identity, e.g. at least 85%, at least 90%, at least 93%, at least 95%, at least 97% sequence identity, preferably at least 93% sequence identity and, optionally, at least 86%, e.g. at least 90%, at least 95%, preferably at least 96%, sequence similarity sequence similarity to the corresponding framework regions taken from the Vκ1 sequence according to SEQ ID NO: 41, and wherein said LFW4 is a Vλ-based sequence and is at least 90% identical to SEQ ID NO: 63, preferably said LFW4 is as set forth in SEQ ID NO: 63, SEQ ID NO: 79 or SEQ ID NO: 80, more preferably said LFW4 is as set forth in SEQ ID NO: 63;

in particular:
wherein the variable heavy chain comprises HFW1 as set forth in SEQ ID NO: 2, HFW2 as set forth in SEQ ID NO: 3, HFW3 as set forth in SEQ ID NO: 4, and HFW4 as set forth in SEQ ID NO: 5; and the variable light chain comprises LFW1 as set forth in SEQ ID NO: 42, LFW2 as set forth in SEQ ID NO: 43, LFW3 as set forth in SEQ ID NO: 44, and LFW4 as set forth in SEQ ID NO: 63;

or (f) wherein said HFW1, HFW2, HFW3, and HFW4 regions together exhibit at least 85% sequence identity, e.g. at least 90%, at least 93%, at least 95%, at least 97% sequence identity, preferably at least 95% sequence identity, more preferably at least 97% sequence identity and, optionally, at least 90% sequence similarity, e.g. at least 93%, at least 95%, at least 96% sequence similarity, preferably at least 95% sequence similarity, more preferably at least 96% sequence similarity to the corresponding framework regions taken from the VH1A sequence according to SEQ ID NO: 1, and wherein said LFW1, LFW2, and LFW3 regions together exhibit at least 80% sequence identity, e.g. at least 85%, at least 90%, at least 93%, at least 95%, at least 97% sequence identity, preferably at least 93% sequence identity and, optionally, at least 86%, preferably at least 90% sequence similarity, at least 95%, at least 96%, preferably at least 90%, more preferably at least 96% sequence similarity to the corresponding framework regions taken from the Vκ3 sequence according to SEQ ID NO: 51, and wherein said LFW4 is a Vλ-based sequence and is at least 90% identical to SEQ ID NO: 63, preferably said LFW4 is as set forth in SEQ ID NO: 63, SEQ ID NO: 79 or SEQ ID NO: 80, more preferably said LFW4 is as set forth in SEQ ID NO: 63;

in particular:
wherein the variable heavy chain comprises HFW1 as set forth in SEQ ID NO: 2, HFW2 as set forth in SEQ ID NO: 3, HFW3 as set forth in SEQ ID NO: 4, and HFW4 as set forth in SEQ ID NO: 5; and the variable light chain comprises LFW1 as set forth in SEQ ID NO: 52, LFW2 as set forth in SEQ ID NO: 53, LFW3 as set forth in SEQ ID NO: 54, and LFW4 as set forth in SEQ ID NO: 63;

or (g) wherein said HFW1, HFW2, HFW3, and HFW4 regions together exhibit at least 85%, e.g. at least 90%, at least 93%, at least 95% sequence identity, at least 97%, preferably at least 90%, more preferably at least 95%, sequence identity and, optionally, at least 90%, preferably at least 93% sequence similarity, more preferably at least 96% sequence similarity to the corresponding framework regions taken from the VH1B sequence according to SEQ ID NO: 6, and wherein said LFW1, LFW2, and LFW3 regions together exhibit at least 80% sequence identity, e.g. at least 85%, at least 90%, at least 93%, at least 95%, at least 97% sequence identity, preferably at least 93% sequence identity and, optionally, at least 86%, e.g. at least 90%, at least 95%, preferably at least 96%, sequence similarity to the corresponding framework regions taken from the Vκ1 sequence according to SEQ ID NO: 41, and wherein said LFW4 is a Vλ-based sequence and is at least 90% identical to SEQ ID NO: 63, preferably said LFW4 is as set forth in SEQ ID NO: 63, SEQ ID NO: 79 or SEQ ID NO: 80, more preferably said LFW4 is as set forth in SEQ ID NO: 63; in particular:
wherein the variable heavy chain comprises HFW1 as set forth in SEQ ID NO: 7, HFW2 as set forth in SEQ ID NO: 8, HFW3 as set forth in SEQ ID NO: 9, and HFW4 as set forth in SEQ ID NO: 10; and the variable light chain comprises LFW1 as set forth in SEQ ID NO: 42, LFW2 as set forth in SEQ ID NO: 43, LFW3 as set forth in SEQ ID NO: 44, and LFW4 as set forth in SEQ ID NO: 63;

or (h) wherein said HFW1, HFW2, HFW3, and HFW4 regions together exhibit at least 85%, e.g. at least 90%, at least 93%, at least 95%, at least 97% sequence identity, preferably at least 90%, more preferably at least 95%, sequence identity and, optionally, at least 90%, preferably at least 93% sequence similarity, more preferably at least 96% sequence similarity to the corresponding framework regions taken from the VH1B sequence according to SEQ ID NO: 6, and wherein said LFW1, LFW2, and LFW3 regions together exhibit at least 80% sequence identity, e.g. at least 85%, at least 90%, at least 93%, at least 95%, at least 97% sequence identity, preferably at least 93% sequence identity and, optionally, at least 86% sequence similarity, preferably at least 90%, more preferably at least 95%, and even more preferably at least 96% sequence similarity to the corresponding framework regions taken from the Vκ3 sequence according to SEQ ID NO: 51, and wherein said LFW4 is a Vλ-based sequence and is at least 90% identical to SEQ ID NO: 63, preferably said LFW4 is as set forth in SEQ ID NO: 63, SEQ ID NO: 79 or SEQ ID NO: 80, more preferably said LFW4 is as set forth in SEQ ID NO: 63;

in particular:
wherein the variable heavy chain comprises HFW1 as set forth in SEQ ID NO: 7, HFW2 as set forth in SEQ ID NO: 8, HFW3 as set forth in SEQ ID NO: 9, and HFW4 as set forth in SEQ ID NO: 10; and the variable light chain comprises LFW1 as set forth in SEQ ID NO: 52, LFW2 as set forth in SEQ ID NO: 53, LFW3 as set forth in SEQ ID NO: 54, and LFW4 as set forth in SEQ ID NO: 63.

In embodiments alternative to those shown in (a) to (h) above, said HFW1, HFW2, and HFW3 regions together exhibit at least 82%, e.g. at least 85%, at least 90%, at least 95%, at least 97%, sequence identity, preferably at least 90%, sequence identity and, optionally, at least 90%, e.g. at least 93%, preferably at least 95%, sequence similarity to the corresponding framework regions of the respective VH sequences.

Suitably, the antibody of the invention or functional fragment thereof comprises
(a) a variable light chain,
wherein the variable light chain comprises, from N-terminus to C-terminus, the regions LFW1-LCDR1-LFW2-LCDR2-LFW3-LCDR3-LFW4 regions, wherein each LFW designates a light chain framework region, and each LCDR designates a light chain complementarity-determining region,
(b) a variable heavy chain
wherein the variable heavy chain comprises, from N-terminus to C-terminus, the regions HFW1-

HCDR1-HFW2-HCDR2-HFW3-HCDR3-HFW4,
wherein each HFW designates a heavy chain framework region, and each HCDR designates a heavy chain complementarity-determining region,
and wherein:
(i) said LFW1, LFW2, LFW3, LFW4, HFW1, HFW2, HFW3, and HFW4 regions together exhibit at least 93% sequence identity, e.g., at least 95%, at least 97% sequence identity, and, optionally, at least 95% sequence similarity to the corresponding framework regions taken from the Vκ1/sk17 sequence according to SEQ ID NO: 57 and from the VH1A sequence according to SEQ ID NO: 1,
and wherein
said LFW1, LFW2, and LFW3 regions together exhibit at least 80% sequence identity to the corresponding framework regions taken from the Vκ1/sk17 sequence according to SEQ ID NO: 57; and
said LFW4 is a Vλ-based sequence and is at least 90% identical to SEQ ID NO: 63; and
said HFW1, HFW2, HFW3, and HFW4 regions together exhibit at least 85% sequence identity to the corresponding framework regions taken from the VH1A sequence according to SEQ ID NO: 1;
or
(ii) said LFW1, LFW2, LFW3, LFW4, HFW1, HFW2, HFW3, and HFW4 regions together exhibit at least 90% sequence identity, e.g., at least 95%, at least 97% sequence identity, and, optionally, at least 92% sequence similarity to the corresponding framework regions taken from the Vκ1/sk17 sequence according to SEQ ID NO: 57 and from the VH1B sequence according to SEQ ID NO:6,
and wherein
said LFW1, LFW2, and LFW3 regions together exhibit at least 80% sequence identity to the corresponding framework regions taken from the Vκ1/sk17 sequence according to SEQ ID NO: 57; and
said LFW4 is a Vλ-based sequence and is at least 90% identical to SEQ ID NO: 63; and
said HFW1, HFW2, HFW3, and HFW4 regions together exhibit at least 85% sequence identity to the corresponding framework regions taken from the VH1B sequence according to SEQ ID NO: 6;
or
(iii) said LFW1, LFW2, LFW3, LFW4, HFW1, HFW2, HFW3, and HFW4 regions together exhibit at least 75% sequence identity, e.g., at least 80%, at least 85%, at least 90%, at least 95%, at least 97% sequence identity, and, optionally, at least 80% sequence similarity, e.g., at least 85%, at least 90%, at least 95%, at least 97% sequence similarity, to the corresponding framework regions taken from the Vκ1/sk17 sequence according to SEQ ID NO: 57 and from the VH4 sequence according to SEQ ID NO: 21,
and wherein
said LFW1, LFW2, and LFW3 regions together exhibit at least 80% sequence identity to the corresponding framework regions taken from the Vκ1/sk17 sequence according to SEQ ID NO: 57; and
said LFW4 is a Vλ-based sequence and is at least 90% identical to SEQ ID NO: 63; and
said HFW1, HFW2, HFW3, and HFW4 regions together exhibit at least 85% sequence identity to
the corresponding framework regions taken from the VH4 sequence according to SEQ ID NO: 21;
or
(iv) said LFW1, LFW2, LFW3, LFW4, HFW1, HFW2, HFW3, and HFW4 regions together exhibit at least 85% sequence identity, e.g., at least 90%, at least 95%, at least 97% sequence identity, and, optionally, at least 80% sequence similarity, e.g., at least 85%, at least 90%, at least 95%, at least 97% sequence similarity, to the corresponding framework regions taken from the Vκ3/sk17 sequence according to SEQ ID NO: 61 and from the VH1A sequence according to SEQ ID NO: 1,
and wherein
said LFW1, LFW2, and LFW3 regions together exhibit at least 80% sequence identity to the corresponding framework regions taken from the Vκ3/sk17 sequence according to SEQ ID NO: 61; and
said LFW4 is a Vλ-based sequence and is at least 90% identical to SEQ ID NO: 63; and
said HFW1, HFW2, HFW3, and HFW4 regions together exhibit at least 85% sequence identity to the corresponding framework regions taken from the VH1A sequence according to SEQ ID NO: 1;
or
(v) said LFW1, LFW2, LFW3, LFW4, HFW1, HFW2, HFW3, and HFW4 regions together exhibit at least 90% sequence identity, e.g., at least 95%, at least 97% sequence identity, and, optionally, at least 90% sequence similarity, e.g., at least 95%, at least 97% sequence similarity, to the corresponding framework regions taken from the Vκ3/sk17 sequence according to SEQ ID NO: 61 and from the VH1B sequence according to SEQ ID NO:6,
and wherein
said LFW1, LFW2, and LFW3 regions together exhibit at least 80% sequence identity to the corresponding framework regions taken from the Vκ3/sk17 sequence according to SEQ ID NO: 61; and
said LFW4 is a Vλ-based sequence and is at least 90% identical to SEQ ID NO: 63; and
said HFW1, HFW2, HFW3, and HFW4 regions together exhibit at least 85% sequence identity to the corresponding framework regions taken from the VH1B sequence according to SEQ ID NO: 6;
or
(vi) said LFW1, LFW2, LFW3, LFW4, HFW1, HFW2, HFW3, and HFW4 regions together exhibit at least 70% sequence identity, e.g., at least 75%, at least 80%, at least 85%, at least 90%, at least 95%, at least 97% sequence identity, and, optionally, at least 75% sequence similarity, e.g., at least 80%, at least 85%, at least 90%, at least 95%, at least 97% sequence similarity, to the corresponding framework regions taken from the Vκ3/sk17 sequence according to SEQ ID NO: 61 and from the VH4 sequence according to SEQ ID NO: 21,
and wherein
said LFW1, LFW2, and LFW3 regions together exhibit at least 80% sequence identity to the corresponding framework regions taken from the Vκ3/sk17 sequence according to SEQ ID NO: 61; and
said LFW4 is a Vλ-based sequence and is at least 90% identical to SEQ ID NO: 63; and said HFW1, HFW2, HFW3, and HFW4 regions together exhibit at least 85% sequence identity to the corresponding framework regions taken from the VH4 sequence according to SEQ ID NO: 21.

In embodiments alternative to those shown in (i) to (vi) above, said HFW1, HFW2, and HFW3 regions together exhibit at least 82%, e.g. at least 85%, at least 90%, at least 95%, at least 97% sequence identity, preferably at least 90%, sequence identity and, optionally, at least 90%, e.g. at least 93%, preferably at least 95%, sequence similarity to the corresponding framework regions of the respective VH sequences.

In a preferred embodiment, the antibody of the invention or functional fragment thereof comprises a variable heavy chain comprising HFW1 as set forth in SEQ ID NO: 22, HFW2 as set forth in SEQ ID NO: 23, HFW3 as set forth in SEQ ID NO: 24, and HFW4 as set forth in SEQ ID NO: 25; and a variable light chain comprising LFW1 as set forth in SEQ ID NO: 42, LFW2 as set forth in SEQ ID NO: 43, LFW3 as set forth in SEQ ID NO: 44, and LFW4 as set forth in SEQ ID NO: 63. In a more preferred embodiment, the antibody of the invention or functional fragment thereof comprises a variable heavy chain comprising HFW1 as set forth in SEQ ID NO: 27, HFW2 as set forth in SEQ ID NO: 28, HFW3 as set forth in SEQ ID NO: 29, and HFW4 as set forth in SEQ ID NO: 30; and the variable light chain comprising LFW1 as set forth in SEQ ID NO: 42, LFW2 as set forth in SEQ ID NO: 43, LFW3 as set forth in SEQ ID NO: 44 and LFW4 as set forth in SEQ ID NO: 63.

In particular embodiment, the antibody of the invention or functional fragment thereof, in particular the antibody or the functional fragment thereof selected from the list of Vκ1 λ-capped/VH1A, Vκ1 λ-capped/VH1B, Vκ1 λ-capped/VH4, Vκ1 λ-capped/VH4$_{mut}$, Vκ3 λ-capped/VH1A, Vκ3 λ-capped/VH1B, Vκ3 λ-capped/VH4, and Vκ3 λ-capped/VH4$_{mut}$, has the following characteristics:

It has an average midpoint of thermal unfolding temperature (Tm) exceeding at least 60° C., at least 65° C., at least 70° C., at least 80° C., or at least 90° C., when expressed in the scFv (single chain variable fragment format) antibody format, as determined by differential scanning fluorimetry (DSF) as described earlier (Egan, et al., MAbs, 9(1) (2017), 68-84; Niesen, et al., Nature Protocols, 2(9) (2007) 2212-2221) in five phosphate-citrate buffers at pH values ranging from 3.5 to 7.5 and containing 0.15 M NaCl. The midpoint of transition for the thermal unfolding of the scFv constructs is determined by Differential Scanning Fluorimetry using the fluorescence dye SYPRO® orange. Samples in relevant excipient conditions are prepared at a final protein concentration of 50 μg ml$^{-1}$ by spiking in stock excipients that are prepared in relevant buffer. For a buffer scouting experiment samples are diluted in final scFv buffers with different pH values (pH 3.4, 4.4, 5.4, 6.4 and 7.2) containing a final concentration of 5× SYPRO® Orange in a total volume of 100 μl. Along with the unknown samples the scFv DSF reference is measured as internal control. Twenty-five microliters of prepared samples are added in triplicate to white-walled AB gene PCR plates. The assay is performed in a qPCR machine used as a thermal cycler, and the fluorescence emission is detected using the software's custom dye calibration routine. The PCR plate containing the test samples is subjected to a temperature ramp from 25° C. to 96° C. in increments of 1° C. with 30 s pauses after each temperature increment. The total assay time is about two hours. The Tm is calculated by the software GraphPad Prism using a mathematical second derivative method to calculate the inflection point of the curve. The reported Tm is an average of three measurements.

In a preferred embodiment, said antibody or functional fragment thereof has an average midpoint of thermal unfolding temperature (Tm) exceeding at least 65° C., preferably at least 69° C. The protein is analyzed over the course of 14 days of storage at 37° C. in 50 mM citrate-phosphate pH 6.4, 150 mM NaCl with respect to oligomerization by SE-HPLC. Prior to the study the samples are concentrated to 10 g l$^{-1}$ and d0 time points are determined. The monomer content is quantified by separation of the samples on a Shodex KW-402.5-4F column and evaluation of the resulting chromatograms. For the calculation of the relative percentage of protein monomer the area of the monomeric peak is divided by the total area of peaks that cannot be attributed to the sample matrix. In a preferred embodiment, said antibody or functional fragment thereof exhibits a loss of monomeric content of less than 15%, 12%, 10%, 7%, 5%, or 2% when stored for two weeks at a concentration of 10 g l$^{-1}$ at 37° C. in 50 mM Citrate-Phosphate pH 6.4, 150 mM NaCl, preferably less than 5%, more preferably less than 2%.

In particular embodiments, said complementarity-determining regions HCDR1, HCDR2, HCDR3, LCDR1, LCDR2 and LCDR3 are either together specific for a target of interest, or are placeholder regions that can be replaced by the corresponding complementarity-determining regions from a donor antibody with specificity for a target of interest.

In one embodiment of the present invention, said CDR domains HCDR1, HCDR2, HCDR3, LCDR1, LCDR2 and LCDR3 are independently selected from (i) CDR domains HCDR1, HCDR2, HCDR3, LCDR1, LCDR2 and LCDR3 from a parental non-human antibody with specificity for an antigen of interest, particularly from a parental rabbit antibody or from a parental rodent antibody, particularly a parental mouse or rat antibody; (ii) CDR domains HCDR1, HCDR2, HCDR3, LCDR1, LCDR2 and LCDR3 from a parental human or humanized antibody, particularly from an antibody approved for therapy or otherwise being commercialized; (iii) CDR domains HCDR1, HCDR2, HCDR3, LCDR1, LCDR2 and LCDR3 derived from the CDR domains according to (i) or (ii), particularly CDR domains obtained by optimizing one or more of the CDR domains according to (i) or (ii); and (iv) a CDR domain to be replaced by one or more CDR domains according to (i), (ii) and/or (iii). In the case of (iv), any sequence can be used as CDR sequence that is compatible with the intended use of the respective variable domain. For example, if the antibody variable domain comprising said CDR sequence has to be expressed prior to the intended replacement of said CDR sequence, a CDR from a well-expressed antibody variable domain may be chosen. In the case that no expression has to be performed, any sequence may be used that is compatible with the intended replacement steps. Due to the function as placeholder CDR, no actual antigen-binding has to be supported by said CDR sequences in such a situation.

In particular embodiments, the antibody or functional fragment thereof has binding specificity for a target of interest. As such the antibody or functional fragment of the present invention comprises complementarity-determining regions HCDR1, HCDR2, HCDR3, LCDR1, LCDR2 and LCDR3 which are together specific for a target of interest.

As used herein, said complementarity-determining regions HCDR1, HCDR2, HCDR3, LCDR1, LCDR2 and LCDR3 are together specific for target of interest when they together retain the ability to specifically bind to a given target of interest, e.g. antigen. The term "specifically bind" or "binding specificity" as used herein refers to the ability of an individual antibody comprising said complementarity-determining regions HCDR1, HCDR2, HCDR3, LCDR1, LCDR2 and LCDR3 to react with one antigenic determinant and not with a different antigenic determinant. Binding affinity of an antibody is the strength of the reaction between a single antigenic determinant and the antibody. In particular, the term "said complementarity-determining regions HCDR1, HCDR2, HCDR3, LCDR1, LCDR2 and LCDR3 are together specific for target of interest" refers to complementarity-determining regions raised and/or selected against a given target of interest and which together retain their ability to recognize said target of interest. The term "recognize" as used herein refers to an ability to find and interact (e.g., binds, blocks, inhibits, antagonizes, agonizes) with a corresponding target of interest, in particular conformational epitope of said target of interest.

As used herein, a binding molecule is "specific to/for", "specifically recognizes", or "specifically binds to" a target, such as for example human IL23R, when such binding molecule is able to discriminate between such target biomolecule and one or more reference molecule(s), since binding specificity is not an absolute, but a relative property. In its most general form (and when no defined reference is mentioned), "specific binding" is referring to the ability of the binding molecule to discriminate between the target biomolecule of interest and an unrelated biomolecule, as determined, for example, in accordance with a specificity assay methods known in the art. Such methods comprise, but are not limited to Western blots, ELISA, RIA, ECL, IRMA, SPR (Surface plasmon resonance) tests and peptide scans. For example, a standard ELISA assay can be carried out. The scoring may be carried out by standard colour development (e.g. secondary antibody with horseradish peroxide and tetramethyl benzidine with hydrogen peroxide). The reaction in certain wells is scored by the optical density, for example, at 450 nm. Typical background (=negative reaction) may be about 0.1 OD; typical positive reaction may be about 1 OD. This means the ratio between a positive and a negative score can be 10-fold or higher. In a further example, an SPR assay can be carried out, wherein at least 10-fold, preferably at least 100-fold difference between a background and signal indicates on specific binding. Typically, determination of binding specificity is performed by using not a single reference biomolecule, but a set of about three to five unrelated biomolecules, such as milk powder, BSA, transferrin or the like.

However, "specific binding" also may refer to the ability of a binding molecule to discriminate between the target biomolecule and one or more closely related biomolecule(s), which are used as reference points. Additionally, "specific binding" may relate to the ability of a binding molecule to discriminate between different parts of its target antigen, e.g. different domains, regions or epitopes of the target biomolecule, or between one or more key amino acid residues or stretches of amino acid residues of the target biomolecule.

In the context of the present invention, the term "epitope" refers to that part of a given target biomolecule that is required for specific binding between the target biomolecule and a binding molecule. An epitope may be continuous, i.e. formed by adjacent structural elements present in the target biomolecule, or discontinuous, i.e. formed by structural elements that are at different positions in the primary sequence of the target biomolecule, such as in the amino acid sequence of a protein as target, but in close proximity in the three-dimensional structure, which the target biomolecule adopts, such as in the bodily fluid.

In one embodiment of the present invention, the isolated antibody or functional fragment thereof is selected from: an IgG antibody, a Fab and an scFv fragment. Suitably, the antibody of the invention or functional fragment thereof is scFv antibody fragment. "Single-chain Fv" or "scFv" or "sFv" antibody fragments comprise the VH and VL domains of an antibody, wherein these domains are present in a single polypeptide chain. Generally, the Fv polypeptide further comprises a polypeptide linker between the VH and VL domains which enables the sFv to form the desired structure for target binding. "Single-chain Fv" or "scFv" antibody fragments comprise the VH and VL domains of antibody, wherein these domains are present in a single polypeptide chain. Generally, the scFv polypeptides further comprises a polypeptide linker between the VH and VL domains which enables the scFv to form the desired structure for antigen binding (see, for example, Plückthun, The pharmacology of Monoclonal Antibodies, vol. 113, Rosenburg and Moore eds., (Springer-Verlag, New York, 1994), pp. 269-315).

In particular embodiments, said functional fragment is an scFv format comprising the linker according to SEQ ID NO: 64 or SEQ ID NO: 65, preferably according to SEQ ID NO: 64.

In another particular embodiment of the present invention, the isolated antibody or functional fragment thereof is a multispecific construct, e.g., bispecific construct, or a multivalent constructs, e.g., bivalent construct, which is an antibody format selected from any suitable multispecific, e.g. bispecific, format known in the art, including, by way of non-limiting example, formats based on a single-chain diabody (scDb), a tandem scDb (Tandab), a linear dimeric scDb (LD-scDb), a circular dimeric scDb (CD-scDb), a bispecific T-cell engager (BiTE; tandem di-scFv), a tandem tri-scFv, a tribody (Fab-(scFv)2) or bibody (Fab-(scFv)1), triabody, scDb-scFv, bispecific Fab2, di-miniantibody, tetrabody, scFv-Fc-scFv fusion, di-diabody, DVD-Ig, COVD, IgG-scFab, scFab-dsscFv, Fv2-Fc, IgG-scFv fusions, such as bsAb (scFv linked to C-terminus of light chain), Bs1Ab (scFv linked to N-terminus of light chain), Bs2Ab (scFv linked to N-terminus of heavy chain), Bs3Ab (scFv linked to C-terminus of heavy chain), Ts1Ab (scFv linked to N-terminus of both heavy chain and light chain), Ts2Ab (dsscFv linked to C-terminus of heavy chain), and Knob-into-Hole antibodies (KiHs) (bispecific IgGs prepared by the KiH technology), a MATCH (described in WO 2016/0202457; Egan T., et al., mAbs 9 (2017) 68-84) and DuoBodies (bispecific IgGs prepared by the Duobody technology) (MAbs. 2017 February/March; 9(2):182-212. doi: 10.1080/19420862.2016.1268307). Particularly suitable for use herein is a single-chain diabody (scDb), in particular a bispecific monomeric scDb.

The term "diabodies" refers to antibody fragments with two antigen-binding sites, which fragments comprise a VH connected to VL in the same polypeptide chain (VH-VL). By using a linker that is too short to allow pairing between the two domains on the same chain, the domains are forced to pair with the complementary domains of another chain to create two antigen-binding sites. Diabodies may be bivalent or bispecific. Diabodies are described more fully in, for example, EP 404097, WO 1993/01161, Hudson et al., Nat. Med. 9:129-134 (2003), and Hollinger et al., Proc. Natl. Acad. Sci. USA 90: 6444-6448 (1993). Triabodies and tetrabodies are also described in Hudson et al., Nat. Med. 9:129-134 (2003).

The bispecific scDb, in particular the bispecific monomeric scDb, particularly comprises two variable heavy chain domains (VH) or fragments thereof and two variable light chain domains (VL) or fragments thereof connected by linkers L1, L2 and L3 in the order VHA-L1-VLB-L2-VHB-L3-VLA, VHA-L1-VHB-L2-VLB-L3-VLA, VLA-L1-VLB-L2-VHB-L3-VHA, VLA-L1-VHB-L2-VLB-L3-VHA, VHB-L1-VLA-L2-VHA-L3-VLB, VHB-L1-VHA-L2-VLA-L3-VLB, VLB-L1-VLA-L2-VHA-L3-VHB or VLB-L1-VHA-L2-VLA-L3-VHB, wherein the VLA and VHA domains jointly form the antigen binding site for the first antigen, and VLB and VHB jointly form the antigen binding site for the second antigen.

The linker L1 particularly is a peptide of 2-10 amino acids, more particularly 3-7 amino acids, and most particularly 5 amino acids, and linker L3 particularly is a peptide of 1-10 amino acids, more particularly 2-7 amino acids, and most particularly 5 amino acids. The middle linker L2 particularly is a peptide of 10-40 amino acids, more particularly 15-30 amino acids, and most particularly 20-25 amino acids.

In one embodiment of the present invention, the isolated antibody or functional fragment thereof is a multispecific and/or multivalent antibody in a MATCH format described in WO 2016/0202457; Egan T., et al., mAbs 9 (2017) 68-84.

The bispecific, bivalent, multispecific and/or multivalent constructs of the present invention can be produced using any convenient antibody manufacturing method known in the art (see, e.g., Fischer, N. & Leger, O., Pathobiology 74 (2007) 3-14 with regard to the production of bispecific constructs; Hornig, N. & Färber-Schwarz, A., Methods Mol. Biol. 907 (2012)713-727, and WO 99/57150 with regard to bispecific diabodies and tandem scFvs). Specific examples of suitable methods for the preparation of the bispecific construct of the present invention further include, inter alia, the Genmab (see Labrijn et al., Proc. Natl. Acad. Sci. USA 110 (2013) 5145-5150) and Merus (see de Kruif et al., Biotechnol. Bioeng. 106 (2010) 741-750) technologies. Methods for production of bispecific antibodies comprising a functional antibody Fc part are also known in the art (see, e.g., Zhu et al., Cancer Lett. 86 (1994) 127-134); and Suresh et al., Methods Enzymol. 121 (1986) 210-228).

These methods typically involve the generation of monoclonal antibodies, for example by means of fusing myeloma cells with the spleen cells from a mouse that has been immunized with the desired antigen using the hybridoma technology (see, e.g., Yokoyama et al., Curr. Protoc. Immunol. Chapter 2, Unit 2.5, 2006) or by means of recombinant antibody engineering (repertoire cloning or phage display/yeast display) (see, e.g., Chames & Baty, FEMS Microbiol. Letters 189 (2000) 1-8), and the combination of the antigen-binding domains or fragments or parts thereof of two different monoclonal antibodies to give a bispecific construct using known molecular cloning techniques.

In a second aspect, the present invention relates to a pharmaceutical composition comprising the antibody or functional fragment thereof of the present invention, and optionally a pharmaceutically acceptable carrier and/or excipient.

The phrase "pharmaceutically acceptable" refers to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio.

Pharmaceutical compositions in accordance with the present disclosure may further routinely contain pharmaceutically acceptable concentrations of salt, buffering agents, preservatives, supplementary immune potentiating agents such as adjuvants and cytokines and optionally other therapeutic agents. The composition may also include antioxidants and/or preservatives. As antioxidants may be mentioned thiol derivatives (e.g. thioglycerol, cysteine, acetylcysteine, cystine, dithioerythreitol, dithiothreitol, glutathione), tocopherols, butylated hydroxyanisole, butylated hydroxytoluene, sulfurous acid salts (e.g. sodium sulfate, sodium bisulfite, acetone sodium bisulfite, sodium metabisulfite, sodium sulfite, sodium formaldehyde sulfoxylate, sodium thiosulfate) and nordihydroguaiaretic acid. Suitable preservatives may for instance be phenol, chlorobutanol, benzylalcohol, methyl paraben, propyl paraben, benzalkonium chloride and cetylpyridinium chloride.

In particular embodiments provided herein, said antibodies or functional fragments thereof can be isolated, prepared, expressed, or created by recombinant means, such as antibodies expressed using a recombinant expression vector transfected into a host cell, antibodies isolated from a recombinant, combinatorial antibody library, or antibodies prepared, expressed, created or isolated by any other means that involves creation, e.g., via synthesis, genetic engineering of DNA sequences that encode human immunoglobulin sequences, or splicing of sequences that encode human immunoglobulins, e.g., human immunoglobulin gene sequences, to other such sequences.

Thus, in a third aspect, the present invention relates to a nucleic acid sequence or a collection of nucleic acid sequences encoding the antibody or functional fragment thereof of the present invention.

In a fourth aspect, the present invention relates to a vector or a collection of vectors comprising the nucleic acid sequence or a collection of nucleic acid sequences of the present invention. The term "vector" or "expression vector" means a polynucleotide, most commonly a DNA plasmid, comprising nucleotide sequences encoding the antibodies of the invention or a fragment thereof for recombinant expression in host cells, preferably in mammalian cells. A vector may, or may not, be able to replicate in a cell. Once a polynucleotide encoding variable heavy and/or variable light chain of an antibody, or fragment thereof described herein has been obtained, the vector for the production of the antibody molecule can be produced by recombinant DNA technology using techniques well-known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination.

An expression vector can be transferred to a host cell by conventional techniques and the resulting cells can then be cultured by conventional techniques to produce an antibody described herein or a fragment thereof. Thus, the present invention relates to a host cell, particularly an expression host cell, comprising the nucleic acid sequence or the collection of nucleic acid sequences of the present invention, or the vector or collection of vectors of the present invention. In certain embodiments, a host cell contains a vector comprising a polynucleotide encoding both the variable heavy chain and variable light chain of the antibody of the invention, or a fragment thereof. In specific embodiments, a host cell contains two different vectors, a first vector comprising a polynucleotide encoding a variable heavy chain of said antibody, or a fragment thereof, and a second vector comprising a polynucleotide encoding a variable light chain of said antibody, or a fragment thereof. In other embodiments, a first host cell comprises a first vector comprising a polynucleotide encoding a variable heavy chain of said antibody, or a fragment thereof, and a second host cell comprises a second vector comprising a polynucleotide encoding a variable light chain of said antibody, or a functional fragment thereof.

In a sixth aspect, the present invention relates to a method for producing the antibody or functional fragment thereof of the present invention, comprising the step of expressing the nucleic acid sequence or the collection of nucleic acid sequences of the present invention, or the vector or collection of vectors of the present invention, or the host cell, particularly the expression host cell, of the present invention.

In a seventh aspect, the present invention relates to a method for humanizing a non-human antibody, particularly a rabbit or rodent antibody, comprising the step of:
(a) cloning, in one or more steps, nucleic acid sequences encoding variable heavy chain (VH) CDRs and variable light chain (VL) CDRs of said non-human antibody into one or more nucleic acid sequences encoding the antibody or functional fragment thereof according to the present invention, provided that at least the VH CDR3 and the VL CDR3 of said non-human antibody are cloned.

Methods for the humanization of rabbit antibodies or rodent antibodies are well known to anyone of ordinary skill in the art (see, for example, Borras, loc. cit.; Rader et al, The FASEB Journal, express article 10.1096/fj.02-0281fje, published online Oct. 18, 2002; Yu et al (2010) A Humanized Anti-VEGF Rabbit Monoclonal Antibody Inhibits Angiogenesis and Blocks Tumor Growth in Xenograft Models. PLoS ONE 5(2): e9072. doi:10.1371/journal.pone.0009072). The immunization of the rabbits or rodents may be performed with the antigen of interest as such, such as a protein, or, in the case of peptide or protein antigens, by DNA immunization of a rabbit with a nucleic acid, e.g. a plasmid, encoding the peptides or proteins of interest.

In a particular embodiment, the method further comprises the cloning of the VH CDR2 and/or VL CDR1 regions. In a particular embodiment, the method comprises the cloning of both VH CDR2 and VL CDR1 regions.

In a particular embodiment, the method further comprises the cloning of the VH CDR1 and/or VL CDR2 regions. In a particular embodiment, the method comprises the cloning of both VH CDR1 and VL CDR2 regions.

In a particular embodiment, the method further comprises one or more of the steps of:
(aa) immunization of non-human animal, particularly a rabbit or rodent with an antigen of interest; and
(ab) isolating at least one antibody of interest.

In a particular embodiment, the method further comprises one or more of the steps of:
(ac) clonal isolation of affinity matured memory B-cells that interact with the antigen of interest, particularly by using fluorescence activated cell-sorting;
(ad) cultivation of single B cells in a co-cultivation system that does not require immortalization of single B cell clones;
(ae) screening of B cell culture supernatants in a cell-based ELISA to identify at least one antibody binding to the antigen of interest; and/or
(af) cloning of the VH CDRs of at least one antibody into a nucleic acid sequence encoding a human antibody VH domain.

In one embodiment, the framework regions of said non-human antibody together have the highest degree of homology to the corresponding framework regions of a combination of a human VH family selected from VH1A (SEQ ID NO: 1), VH1B (SEQ ID NO: 6), and VH4 (SEQ ID NO: 21), and a human VL family selected from Vκ1 (SEQ ID NO: 41) and Vκ3 (SEQ ID NO: 51). In another embodiment, the framework regions of said non-human antibody together have the highest degree of homology to (i) the framework regions of a combination of a human VH family selected from VH2 (SEQ ID NO: 11), VH3 (SEQ ID NO: 16), VH5 (SEQ ID NO: 31) and VH6 (SEQ ID NO: 36), and a human VL family selected from Vκ1 (SEQ ID NO: 41), Vκ2 (SEQ ID NO: 46), Vκ3 (SEQ ID NO: 51) and Vκ4 (SEQ ID NO: 81); or (ii) the framework regions of a combination of a human VH family selected from VH1A (SEQ ID NO: 1), VH1B (SEQ ID NO: 6), VH2 (SEQ ID NO: 11), VH3 (SEQ ID NO: 16), VH4 (SEQ ID NO: 21), VH5 (SEQ ID NO: 31) and VH6 (SEQ ID NO: 36), and a human VL family selected from Vκ2 (SEQ ID NO: 46) and Vκ4 (SEQ ID NO: 81).

In particular embodiments, the framework regions of said non-human antibody together have the highest degree of homology to the corresponding framework regions of a combination of a human VH family selected from VH2 (SEQ ID NO: 11), VH3 (SEQ ID NO: 16), VH5 (SEQ ID NO: 31) and VH6 (SEQ ID NO: 36), and a human VL family selected from Vκ2 (SEQ ID NO: 46) and Vκ4 (SEQ ID NO: 81).

In an eighth aspect, the present invention relates to a method for optimizing a parental antibody of interest, comprising the step of:
(a) cloning, in one or more steps, nucleic acid sequences encoding VH CDRs and VL CDRs of said parental antibody into one or more nucleic acid sequences encoding the antibody or functional fragment thereof according to the present invention, provided that at least the VH CDR3 and the VL CDR3 of said parental antibody are cloned.

In a particular embodiment, the method further comprises the cloning of the VH CDR2 and/or VL CDR1 regions. In a particular embodiment, the method comprises the cloning of both VH CDR2 and VL CDR1 regions.

In a particular embodiment, the method further comprises the cloning of the VH CDR1 and/or VL CDR2 regions. In a particular embodiment, the method comprises the cloning of both VH CDR1 and VL CDR2 regions.

In one embodiment, the framework regions of said parental antibody overall have the highest degree of homology to the corresponding framework regions of a combination of a human VH family selected from VH1A (SEQ ID NO: 1), VH1B (SEQ ID NO: 6), and VH4 (SEQ ID NO: 21), and a human VL family selected from Vκ1 (SEQ ID NO: 41) and Vκ3 (SEQ ID NO: 51). In another embodiment, the framework regions of said parental antibody overall have the highest degree of homology to (i) the framework regions of a combination of a human VH family selected from VH2 (SEQ ID NO: 11), VH3 (SEQ ID NO: 16), VH5 (SEQ ID NO: 31) and VH6 (SEQ ID NO: 36), and a human VL family selected from Vκ1 (SEQ ID NO: 41), Vκ2 (SEQ ID NO: 46), Vκ3 (SEQ ID NO: 51) and Vκ4 (SEQ ID NO: 81); or (ii) the framework regions of a combination of a human VH family selected from VH1A (SEQ ID NO: 1), VH1B (SEQ ID NO: 6), VH2 (SEQ ID NO: 11), VH3 (SEQ ID NO: 16), VH4 (SEQ ID NO: 21), VH5 (SEQ ID NO: 31) and VH6 (SEQ ID NO: 36), and a human VL family selected from Vκ2 (SEQ ID NO: 46) and Vκ4 (SEQ ID NO: 81).

In particular embodiments, the framework regions of said parental antibody overall have the highest degree of homology to the corresponding framework regions of a combination of a human VH family selected from VH2 (SEQ ID NO: 11), VH3 (SEQ ID NO: 16), VH5 (SEQ ID NO: 31) and VH6 (SEQ ID NO: 36), and a human VL family selected from Vκ2 (SEQ ID NO: 51) and Vκ4 (SEQ ID NO: 81).

In a ninth aspect, the present invention relates to a method of generating a diverse collection of antibodies or functional fragments thereof, comprising the step of:
(a) cloning, in one or more steps, one or more diverse collections of nucleic acid sequences encoding one or more diverse collections of VH CDRs and/or VL CDRs into one or more nucleic acid sequences encoding the antibody or functional fragment thereof according to the present invention.

In a particular embodiment, a diverse collection of nucleic acid sequences encoding a diverse collection of VH CDR3s is cloned.

In particular embodiments, a diverse collection of nucleic acid sequences encoding a diverse collection of VL CDR3s is cloned.

In a particular embodiment, a diverse collection of nucleic acid sequences encoding a diverse collection of VH CDR2s and/or a diverse collection of nucleic acid sequences encoding a diverse collection of VL CDR1s are cloned. In a particular embodiment, both a diverse collection of VH CDR2s and a diverse collection of VL CDR1 regions are cloned.

In a particular embodiment, a diverse collection of nucleic acid sequences encoding a diverse collection of VH CDR1s and/or a diverse collection of nucleic acid sequences encoding a diverse collection of VL CDR2s are cloned. In a particular embodiment, both a diverse collection of VH CDR1s and a diverse collection of VL CDR2s are cloned.

EXAMPLES

The following examples illustrate the invention without limiting its scope.

Example 1

This study was conducted with the aim to identify a human variable VL/VH consensus framework combination consisting of combinatorial pairs of humanized consensus VL and VH domains that exhibits similar or even superior biophysical properties compared to Vκ1/VH3 while fully retaining the specificity and antigen-binding affinity. Based on the assumption that residues that contribute to protein stability have been enriched during evolution in the pool of germline sequences (Steipe et al., J Mol Biol, 240 (1994) 188-92), consensus germline sequences were used. This mitigates the risk of immunogenic reactions induced by aggregation (Joubert et al., J Biol Chem, 287 (2012) 25266-79) and by non-human framework residues in the acceptor framework that may render a framework region non-human and increase occurrence of human T-cell epitopes. In addition to the Vκ/VH (Vκ1, Vκ2, Vκ3, VH1A, VH1B, VH2, VH3, VH4, VH5, VH6) permutation, Numab's stabilizing technology, the so-called λ-cap, was applied to all Vκ domains to evaluate its potentially stabilizing contribution to non-Vκ1/VH3 framework combinations as well as its potential impact on production yields and antigen binding affinity. The λ-cap technology entails replacing framework region IV of Vκ-family consensus variable light domains by a Vλ-family germline sequence (λ-cap).

Superiority of λ-capped over non-λ-capped Vκ1/VH3 consensus scFvs in terms of stability has been demonstrated earlier (WO 2014/206561).

To identify the most appropriate human acceptor antibody variable domain scaffold for the humanization and stabilization of rabbit antibody variable domains we set out to test combinations of the Vκ-family light chain consensus sequences for Vκ1, Vκ2, and Vκ3 with all human VH consensus sequences (VH1A, 1B, 2, 3, 4, 5, and 6) together with different human germline lambda-type light chain framework IV sequences (λ-cap, specifically SEQ ID NO: 62). For this, a rabbit CDR set (SEQ ID NO: 66 to SEQ ID NO: 71), specifically binding to human interleukin-23 receptor (IL23R), was engrafted on all consensus framework combinations shown in FIG. 1 (upper half), allowing for the direct comparison of humanized scFv fragments based on the properties of their distinct consensus acceptor frameworks only. Further, control molecules lacking the kappa-to-lambda substitution in framework region IV (uncapped), were produced for each VL/VH combination (FIG. 1, lower half) to contrast with their respective capped variant. The results were then corroborated with alternative rabbit CDR sets. To our surprise, certain non-Vκ1/VH3 combinations gained more in expression yield, unfolding temperature and/or monomer stability from the λ-cap than the Vκ1/VH3 scaffold. Some Vκ/VH3 combinations together with the λ-cap even clearly outperformed the λ-capped Vκ1/VH3 combination in terms of thermal unfolding and monomer stability, which is unexpected in the light of the prior art. Further, we identified a preferred lambda germline sequence for use as a lambda-cap to optimize stability and maintain antigen-binding affinity.

Results:

In a first step, the de novo synthesized VL and VH gene sequences were cloned into a bacterial expression vector by domain shuffling and successfully expressed in *Escherichia coli*. All constructs were expressed in scFv format with VL-VH domain orientation and a 20 amino acid glycine-serine $(G_4S)_4$-linker (SEQ ID NO: 64) between the domains. ScFv molecules were purified by using an adequate purification strategy (Protein L affinity chromatography followed by size exclusion chromatography) and the quality of all scFvs used for subsequent analyses was initially comparable, as the monomeric content of all constructs was above 95%. Overall, full consensus constructs fairly consistently exhibited inferior properties than their λ-capped counterparts when biophysical (aggregation and thermal stability) and functional (SPR) properties were compared. We found that scFv molecules comprising Vκ(1-3) containing the full replacement of framework region IV by a Vλ germline sequence (λ-cap) and a VH(1-6) consensus domain led to generally preferable stability profiles compared to the corresponding full consensus (uncapped) molecules. Specifically, λ-capped scFv variants were—across different germline families—mostly superior in terms of producibility, midpoint of thermal unfolding and stability of the monomeric state during storage at various temperatures.

In the following several examples will be discussed in more detail.

Example 2

Determination of Biophysical Data for scFv Constructs

Expression Yield:
Single-chain variable fragments were produced using generic conditions, as described in Egan et al., MAbs 9

(2017) 68-84. Expression was performed in E. coli where the antibody fragments accumulated in inclusion bodies which were then solubilized and refolded in a generic refolding buffer as described in (Egan et al., MAbs, 9 (2017) 68-84). The yield per litre of expression culture for all molecules is shown in FIG. 2. Most strikingly these results show the consistently improved producibility of lambda-capped scaffolds (white bars) compared to the respective uncapped counterparts (grey bars) with only two exceptions (Vκ2/VH5 and Vκ3/VH4).

The production of two molecules (Vκ2/VH1B and Vκ2/VH2) was only enabled by λ-capping of their light chain, as uncapped full consensus variants were not producible at all. Further, VH3 comprising framework combinations show highest yields within a group of molecules sharing the Vκ-chain of the same subfamily (Vκ1, Vκ2 Vκ3). Apart from the Vκ1/VH3 combination, Vκ1/VH4, Vκ2/VH4 and Vκ3/VH1B combinations profited most from the replacement of framework region IV by a Vλ germline as they experience the highest fold increase in yield upon λ-capping within their respective groups sharing the same light chain framework.

Thermal Stability

Figure 3:
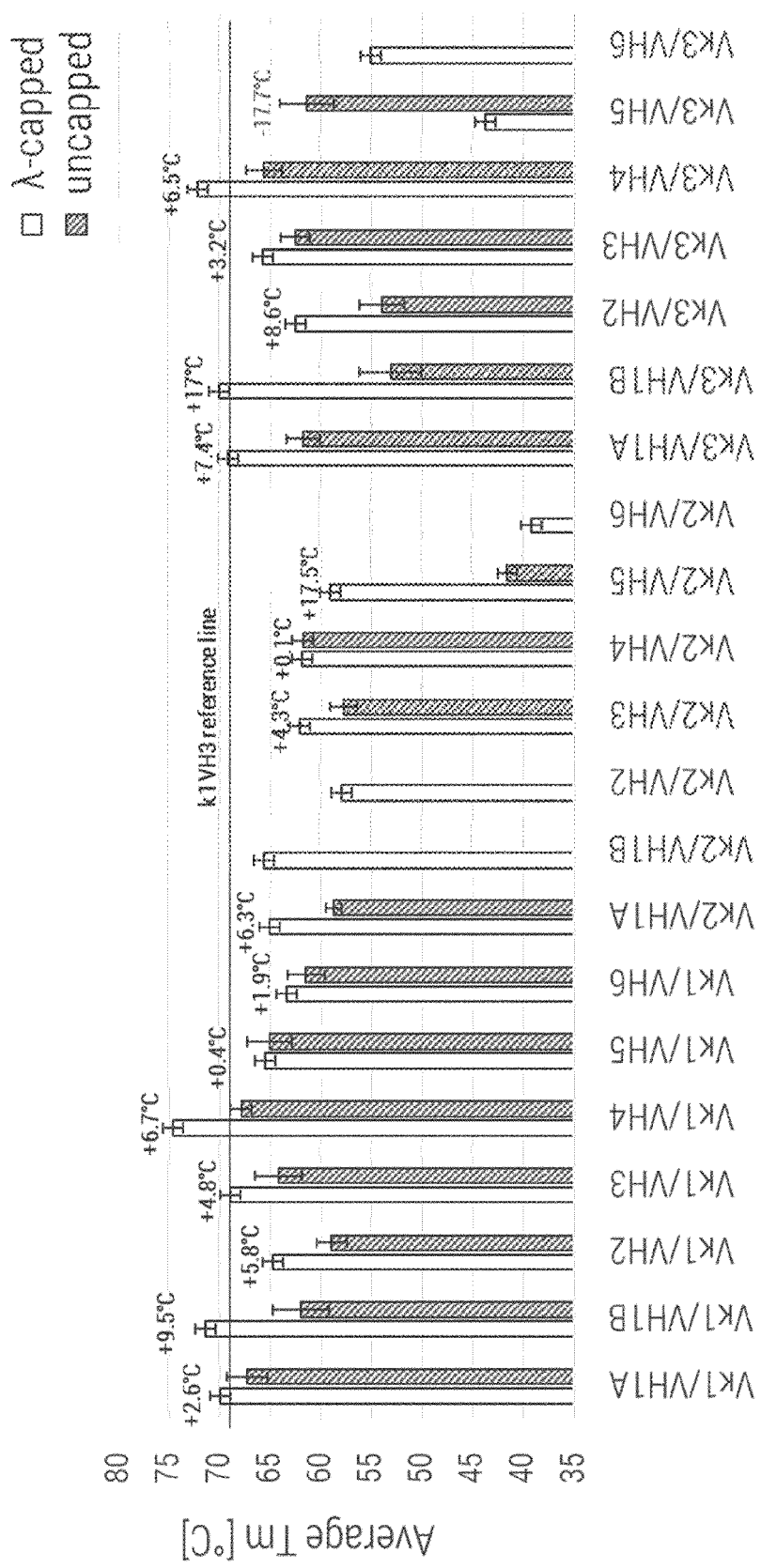
FIG. 3 shows the average thermal unfolding temperature (Tm) determined by differential scanning fluorimetry (DSF) of capped framework variants (white bars) and uncapped framework counterparts (grey bars) measured in five phosphate-citrate buffers at pH values ranging from 3.5 to 7.5 and containing 0.15 M NaCl.
Figure 4A:
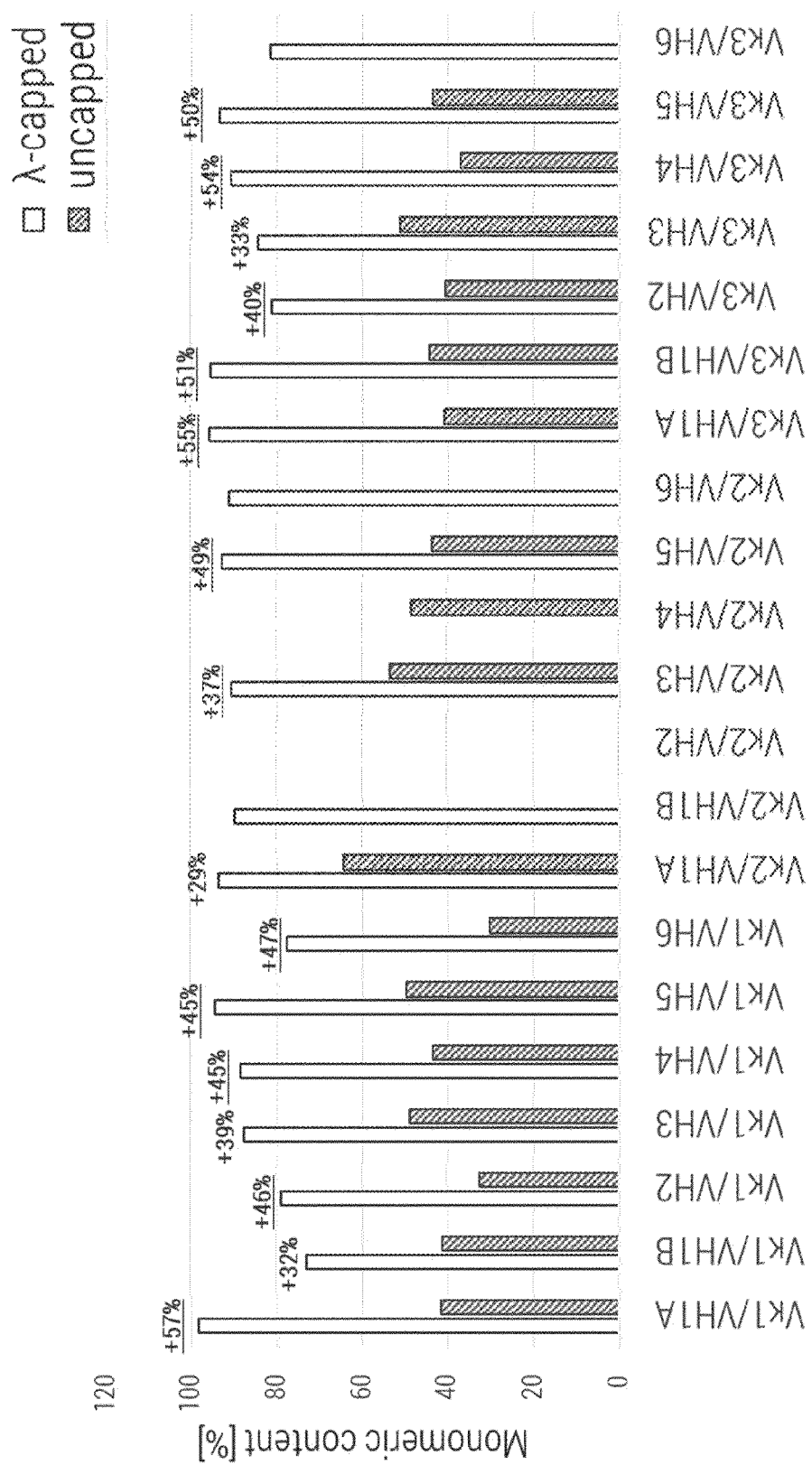
FIG. 4 shows the comparison of normalized (to initial monomer content) monomeric content determined by SE-HPLC after two weeks' storage at 37° C. and 10 mg/mL of capped (white bars) and uncapped variants (grey bars) (FIG. 4A). Capped variant Vκ1/VH3 reference sample exhibited 39% less reduction in monomer content compared to the uncapped variant. Underlined values indicate framework combinations exhibiting less monomer loss compared to their uncapped counterpart during the incubation than the reference Vκ1/VH3 germline combination. Monomeric content loss in % is displayed in FIG. 4B for capped framework variants (white bars) and uncapped framework counterparts (grey bars). Several frameworks exhibit less monomeric content loss than the reference as indicated by a reference line (Vκ1/VH3).
Figure 4B:
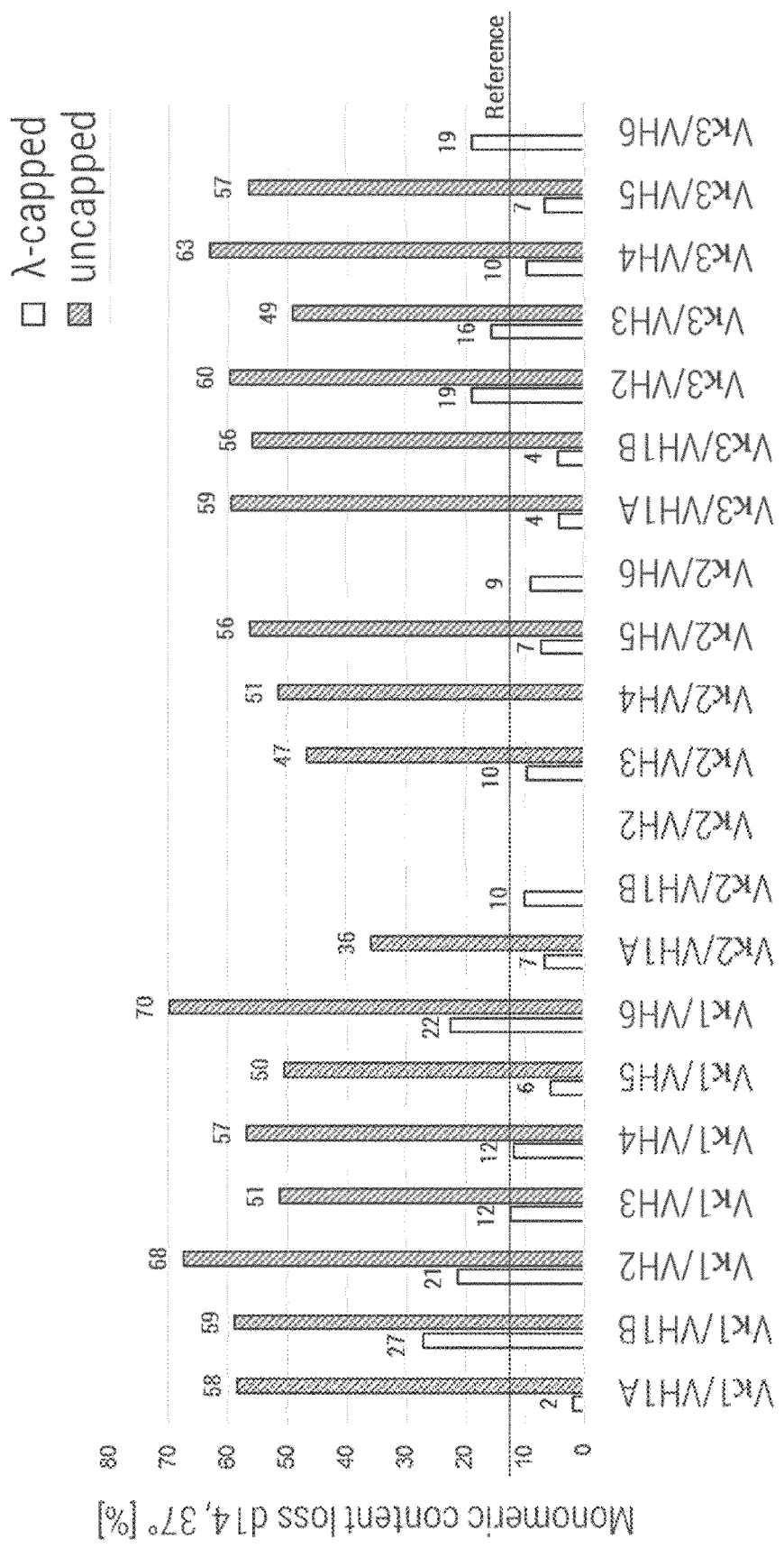

The midpoint of thermal unfolding (Tm) was determined for all molecules by differential scanning fluorimetry (DSF) as described earlier (Egan et al., MAbs, 9 (2017) 68-84; Niesen et al., Nature Protocols, 2(9) (2007) 2212-2221) in five phosphate-citrate buffers at pH's ranging from 3.5 to 7.5 and containing 0.15 M NaCl. FIG. 3 shows data for the average pH over the measured pH-range including standard deviations. Lambda-capped scFv variants (white bars) display consistently higher average melting temperatures than uncapped (grey bars) variants except for the Vκ3/VH5 combination where the uncapped variant shows a significantly higher average Tm than the capped variant. Surprisingly, the midpoint of thermal unfolding seems not to correlate with the expression yield of molecules as some low expressing framework combinations exhibit very high thermal stability, particularly together with the lambda-cap (e.g. Vκ3/VH4). All combinations of Vκ1 and Vκ3 light chains with VH1A, VH1B and VH4 variable heavy chains result in variable domains with higher unfolding temperatures than that of Vκ1/VH3. Vκ1/VH4 exhibits the highest melting temperature while Vκ2/VH5 and Vκ3/VH1B exhibit the highest relative increase in Tm upon capping.

Storage Stability

A two weeks storage stability study at a concentration of 10 mg/mL at 37° C. was performed with all producible molecules. Monomeric content after storage of the lambda-capped variants was compared to the uncapped variants. Throughout all combinations, light chain capping led to remarkable increases in monomeric content after two weeks' storage at 37° C., between 32% (Vκ1/VH1B) and 57% (Vκ3/VH1A) compared to the uncapped full consensus scFvs. The production of three framework combinations was enabled only by stabilizing the light chain with the λ-cap, as their uncapped counterparts could not be produced in sufficient amounts for this study (Vκ2/VH1B, Vκ2/VH6) or quantitatively precipitated before the study could be initiated (Vκ3/VH6). Vκ2/VH2 combinations could not be produced in sufficient amounts for this study.

Surprisingly, when benchmarked to the lambda-capped Vκ1/VH3 reference molecule, many VL-VH germline combinations display a more pronounced increase in monomeric content upon capping than the reference (circled values). And some combinations experience less monomeric content loss upon storage at 37° C. for two weeks and can therefore be considered as overall more stable than the reference combination. This is the case for the lambda-capped combinations Vκ1/VH1A, Vκ1/VH4, Vκ1/VH5, Vκ2/VH1A, Vκ2/VH1B, Vκ2/VH3, Vκ2/VH5, Vκ3/VH1A, Vκ3/VH1B, Vκ3/VH4, and Vκ3/VH5.

Affinity Measurement

For functional characterization of the humanized rabbit variable domains, the affinity of the respective scFv to IL23R was measured by surface plasmon resonance (SPR). Surprisingly, most molecules retained high antigen-binding affinity which was not expected as exclusively the CDRs, and no donor framework residues were grafted onto the human acceptor scaffolds.

Further, it can be concluded that light chain capping does not adversely impact target affinity as capped and uncapped variants exhibit either at least similar affinities or even a slight overall advantage for capped variants. Kinetics of antibody-target interaction are similar when comparing capped to uncapped variants and within respective molecules sharing the same light chain domain. Only off-rate values ($k_d$) of Vκ3 constructs show slightly higher variability, with Vκ3/VH1A and Vκ3/VH5 showing slightly faster off-rates than their Vκ1 or Vκ2 counterparts. Vκ1/VH3 exhibits a slightly slower off-rate than all other molecules which is also reflected in the overall best dissociation constant. However, some combinations compensate for the disadvantage in the off-rate by faster on-rates (e.g. Vκ1/VH4) resulting in essentially same overall affinity as VH3-comprising scFvs. Table 1 summarizes affinity to human IL23R of all capped and uncapped framework combinations investigated for this study.

TABLE 1

SPR affinity measurement of capped and uncapped framework variants.

| Framework | Capped Affinity to human IL23R (SPR data) | | | Uncapped Affinity to human IL23R (SPR data) | | |
|---|---|---|---|---|---|---|
| | ka [1/Ms] | kd [1/s] | $K_D$ [M] | ka [1/Ms] | kd [1/s] | $K_D$ [M] |
| $V_K1$VH1A | 3.71E+06 | 6.16E−04 | 1.66E−10 | 6.42E+06 | 1.28E−04 | 2E−11 |
| $V_K1$VH1B | 2.40E+06 | 4.78E−04 | 1.99E−10 | 2.45E+06 | 4.13E−04 | 1.68E−10 |
| $V_K1$VH2 | 1.76E+06 | 1.28E−04 | 7.31E−11 | 1.58E+06 | 3.33E−04 | 2.11E−10 |
| $V_K1$VH3 | 3.95E+06 | 5.43E−05 | 1.37E−11 | 1.52E+06 | 5.28E−05 | 3.47E−11 |
| $V_K1$VH4 | 4.20E+06 | 1.91E−04 | 4.55E−11 | 1.78E+06 | 1.76E−04 | 9.91E−11 |
| $V_K1$VH5 | 1.69E+06 | 6.71E−04 | 3.98E−10 | 2.25E+06 | 5.38E−04 | 2.39E−10 |
| $V_K1$VH6 | 1.42E+06 | 3.49E−04 | 2.45E−10 | 1.23E+06 | 3.09E−04 | 2.51E−10 |
| $V_K2$VH1A | 2.39E+06 | 1.84E−04 | 7.72E−11 | 1.26E+06 | 2.79E−04 | 2.22E−10 |
| $V_K2$VH1B | 2.29E+06 | 3.26E−04 | 1.43E−10 | n/a | n/a | n/a |
| $V_K2$VH2 | 1.38E+06 | 1.02E−04 | 7.41E−11 | n/a | n/a | n/a |
| $V_K2$VH3 | 1.95E+06 | 7.77E−05 | 3.97E−11 | 1.82E+06 | 4.30E−05 | 2.36E−11 |

TABLE 1-continued

SPR affinity measurement of capped and uncapped framework variants.

| Framework | Capped Affinity to human IL23R (SPR data) | | | Uncapped Affinity to human IL23R (SPR data) | | |
|---|---|---|---|---|---|---|
| | ka [1/Ms] | kd [1/s] | $K_D$ [M] | ka [1/Ms] | kd [1/s] | $K_D$ [M] |
| $V_K2$VH4 | 2.33E+06 | 1.12E−04 | 4.81E−11 | 1.26E+06 | 1.57E−04 | 1.25E−10 |
| $V_K2$VH5 | 1.50E+06 | 7.15E−04 | 4.76E−10 | 1.57E+06 | 4.75E−04 | 3.03E−10 |
| $V_K2$VH6 | 5.35E+05 | 4.75E−04 | 8.87E−10 | 8.87E+04 | 2.88E−04 | 3.24E−09 |
| $V_K3$VH1A | 2.00E+06 | 1.17E−03 | 5.85E−10 | 1.61E+06 | 4.79E−04 | 2.97E−10 |
| $V_K3$VH1B | 2.80E+06 | 5.06E−04 | 1.81E−10 | 1.59E+06 | 7.24E−04 | 4.55E−10 |
| $V_K3$VH2 | 1.66E+06 | 1.52E−04 | 9.16E−11 | 7.86E+05 | 3.63E−04 | 4.62E−10 |
| $V_K3$VH3 | 2.89E+06 | 6.38E−05 | 2.20E−11 | 1.65E+06 | 6.52E−05 | 3.95E−11 |
| $V_K3$VH4 | 2.35E+06 | 2.88E−04 | 1.23E−10 | 1.89E+06 | 2.63E−04 | 1.39E−10 |
| $V_K3$VH5 | 1.50E+06 | 1.30E−03 | 8.64E−10 | 1.72E+06 | 9.04E−04 | 5.25E−10 |
| $V_K3$VH6 | 1.43E+06 | 5.63E−04 | 3.94E−10 | n/a | n/a | n/a |

Table 2 summarizes all data acquired with human IL23R specific scFv fragments. Each framework variant was compared to its uncapped (full consensus) counterpart in four distinct categories (yield, average Tm, monomeric content loss and $K_D$) and increments were calculated. Values in bold indicate better performance of the respective framework combination relative to the Vκ1/VH3 reference.

Example 3

Confirmation Study with TNF-Specific Molecules

Based on the remarkable overall performance of Vκ1/VH4 and Vκ3/VH4 IL23R specific molecules, these framework combinations were selected as particularly useful for the straight-forward humanization, by simple engraftment of rabbit anti-human TNF CDR's (SEQ ID NO: 72 to SEQ ID NO: 77). The aim of this study was to confirm results obtained with IL23R specific CDR's (SEQ ID NO: 66 to SEQ ID NO: 71). As reference in a controlled confirmation study Vκ1/VH3 and Vκ3/VH3 framework combinations were used for the engraftment of the same anti-TNF CDR sets.

TABLE 2

Summary table for human IL23R specific VL-VH consensus combinations. Values in bold indicate better performance than reference ($V_K1$/VH3).

| Protein | Yield [mg/L expression] | δ yield [%] (capped − uncapped) | Average Tm [° C.] | δ Tm [° C.] (capped − uncapped) | Monomeric content loss [%] | δ monomeric content loss [%] (capped − uncapped) | KD (M) | Ratio (capped/ uncapped) | Selected for confirmation |
|---|---|---|---|---|---|---|---|---|---|
| $V_K1$/VH1A consensus λ-capped | 21 | 35 | 69.8 | 2.7 | 1.8 | −56.6 | 1.66E−10 | 8.3 | YES |
| $V_K1$/VH1A consensus | 16 | | 67.2 | | 58.5 | | 2E−11 | | |
| $V_K1$/VH1B consensus λ-capped | 23 | 55 | 71.4 | 9.5 | 27.0 | −31.8 | 1.99E−10 | 1.2 | YES |
| $V_K1$/VH1B consensus | 15 | | 61.9 | | 58.8 | | 1.68E−10 | | |
| $V_K1$/VH2 consensus λ-capped | 12 | 18 | 64.6 | 5.8 | 21.2 | −46.4 | 7.31E−11 | 0.3 | NO |
| $V_K1$/VH2 consensus | 10 | | 58.8 | | 67.5 | | 2.11E−10 | | |
| $V_K1$/VH3 consensus λ-capped | 57 | 580 | 68.8 | 4.8 | 12.3 | −38.9 | 1.37E−11 | 0.4 | Reference |
| $V_K1$/VH3 consensus | 8 | | 64.1 | | 51.2 | | 3.47E−11 | | |
| $V_K1$/VH4 consensus λ-capped | 33 | 503 | 74.5 | 6.7 | 11.7 | −45.0 | 4.55E−11 | 0.5 | YES |
| $V_K1$/VH4 consensus | 5 | | 67.8 | | 56.7 | | 9.91E−11 | | |
| $V_K1$/VH5 consensus λ-capped | 18 | 214 | 65.4 | 0.4 | 5.6 | −44.8 | 3.98E−10 | 1.7 | NO |
| $V_K1$/VH5 consensus | 6 | | 64.9 | | 50.4 | | 2.39E−10 | | |
| $V_K1$/VH6 consensus λ-capped | 12 | 115 | 63.3 | 1.9 | 22.3 | −47.5 | 2.45E−10 | 1.0 | NO |
| $V_K1$/VH6 consensus | 5 | | 61.4 | | 69.8 | | 2.51E−10 | | |
| $V_K2$/VH1A consensus λ-capped | 22 | 60 | 65.0 | 6.4 | 6.5 | −29.3 | 7.72E−11 | 0.3 | NO |
| $V_K2$/VH1A consensus | 14 | | 58.6 | | 35.8 | | 2.22E−10 | | |
| $V_K2$/VH1B consensus λ-capped | 9 | NA | 65.5 | NA | 10.1 | NA | 1.43E−10 | NA | NO |
| $V_K2$/VH1B consensus | 0 | | NA | | NA | | NA | | |
| $V_K2$/VH2 consensus λ-capped | 1 | NA | 57.9 | NA | NA | NA | 7.41E−11 | NA | NO |
| $V_K2$/VH2 consensus | 0 | | NA | | NA | | NA | | |
| $V_K2$/VH3 consensus λ-capped | 33 | 82 | 62.0 | 4.4 | 9.5 | −37.0 | 3.97E−11 | 1.7 | NO |
| $V_K2$/VH3 consensus | 18 | | 57.6 | | 46.6 | | 2.36E−11 | | |
| $V_K2$/VH4 consensus λ-capped | 15 | 384 | 61.7 | 0.1 | NA | NA | 4.81E−11 | 0.4 | NO |
| $V_K2$/VH4 consensus | 3 | | 61.7 | | 51.5 | | 1.25E−10 | | |
| $V_K2$/VH5 consensus λ-capped | 5 | −48 | 58.9 | 17.5 | 7.2 | −49.0 | 4.76E−10 | 1.6 | NO |
| $V_K2$/VH5 consensus | 10 | | 41.5 | | 56.2 | | 3.03E−10 | | |
| $V_K2$/VH6 consensus λ-capped | 4 | 733 | 39.0 | NA | 9.0 | NA | 8.87E−10 | 0.3 | NO |
| $V_K2$/VH6 consensus | 1 | | NA | | NA | | 3.24E−09 | | |
| $V_K3$/VH1A consensus λ-capped | 24 | 31 | 69.1 | 7.4 | 4.3 | −55.1 | 5.85E−10 | 2.0 | YES |
| $V_K3$/VH1A consensus | 18 | | 61.6 | | 59.3 | | 2.97E−10 | | |

TABLE 2-continued

Summary table for human IL23R specific VL-VH consensus combinations. Values in bold indicate better performance than reference (Vκ1/VH3).

| Protein | Yield [mg/L expression] | δ yield [%] (capped − uncapped) | Average Tm [° C.] | δ Tm [° C.] (capped − uncapped) | Monomeric content loss [%] | δ monomeric content loss [%] (capped − uncapped) | KD (M) | Ratio (capped/ uncapped) | Selected for confirmation |
|---|---|---|---|---|---|---|---|---|---|
| Vκ3/VH1B consensus λ-capped | 14 | 380 | 70.0 | 17.0 | 4.4 | −51.4 | 1.81E−10 | 0.4 | YES |
| Vκ3/VH1B consensus | 3 | | 53.0 | | 55.9 | | 4.55E−10 | | |
| Vκ3/VH2 consensus λ-capped | 3 | 33 | 62.4 | 8.6 | 18.8 | −40.8 | 9.16E−11 | 0.2 | NO |
| Vκ3/VH2 consensus | 3 | | 53.8 | | 59.6 | | 4.62E−10 | | |
| Vκ3/VH3 consensus λ-capped | 28 | 110 | 65.7 | 3.3 | 15.6 | −33.5 | 2.20E−11 | 0.6 | NO |
| Vκ3/VH3 consensus | 13 | | 62.4 | | 49.1 | | 3.95E−11 | | |
| Vκ3/VH4 consensus λ-capped | 3 | −75 | 72.1 | 6.6 | 9.5 | −53.5 | 1.23E−10 | 0.9 | YES |
| Vκ3/VH4 consensus | 13 | | 65.5 | | 63.0 | | 1.39E−10 | | |
| Vκ3/VH5 consensus λ-capped | 17 | 33 | 43.6 | −17.7 | 6.6 | −49.9 | 8.64E−10 | 1.6 | NO |
| Vκ3/VH5 consensus | 125 | | 61.3 | | 56.5 | | 5.25E−10 | | |
| Vκ3/VH6 consensus λ-capped | 3 | 17 | 55.0 | NA | 18.7 | NA | 3.94E−10 | NA | NO |
| Vκ3/VH6 consensus | 2.4 | | NA | | NA | | NA | | |

Results of selected (human IL23R CDR engrafted) framework combinations, namely Vκ1/VH3, Vκ1/VH4, Vκ3/VH3 and Vκ3/VH4 were confirmed by engraftment of human TNF-specific CDRs onto these frameworks. In addition, mutant variant of Vκ1/VH4 framework based molecules, containing amino acids diverging from consensus sequence at specific framework positions (2/81 in VH4), were included in this study.

Confirming the trend observed above with IL23R-specific CDRs that affinity is not affected by CDR-grafting onto VH4 framework combinations, for TNF-specific CDRs the capped Vκ1/VH4 consensus molecule showed even higher affinity than the capped Vκ1/VH3 consensus molecule. Moreover, affinity of Vκ1/VH4 to human TNF could be further improved by introducing two mutations at specific framework positions (T24K and T84S; SEQ ID NO: 78).

Thus, in particular embodiments, the present invention relates to an antibody or functional fragment thereof comprising the VH4$_{mut}$ sequence according to SEQ ID NO: 26.

Importantly (see Table 3), both Vκ1/VH4 molecules—even the non-mutated consensus FW—exhibit higher affinity to human TNF than the Vκ1/VH3 variant. Therefore, this framework appears to be particularly suitable for the straight-forward humanization of rabbit antibodies by the engraftment of CDR sets, and superior over the current state of the art (Vκ1/VH3).

When comparing production yields of TNF specific molecules confirms previously obtained data for IL23R specific molecules as again molecules containing VH3 domain exhibit better producibility than corresponding VH4 containing molecules (Table 4). However, as the generic process for production of scFvs—in particular the refolding process—originally was developed for Vκ1/VH3 framework based molecules, this is likely to bias producibility results in favour of VH3 comprising VL/VH framework combinations. It appears likely that production yields for VH4 comprising framework combinations could be further optimized using an adapted production process.

Figure 5:
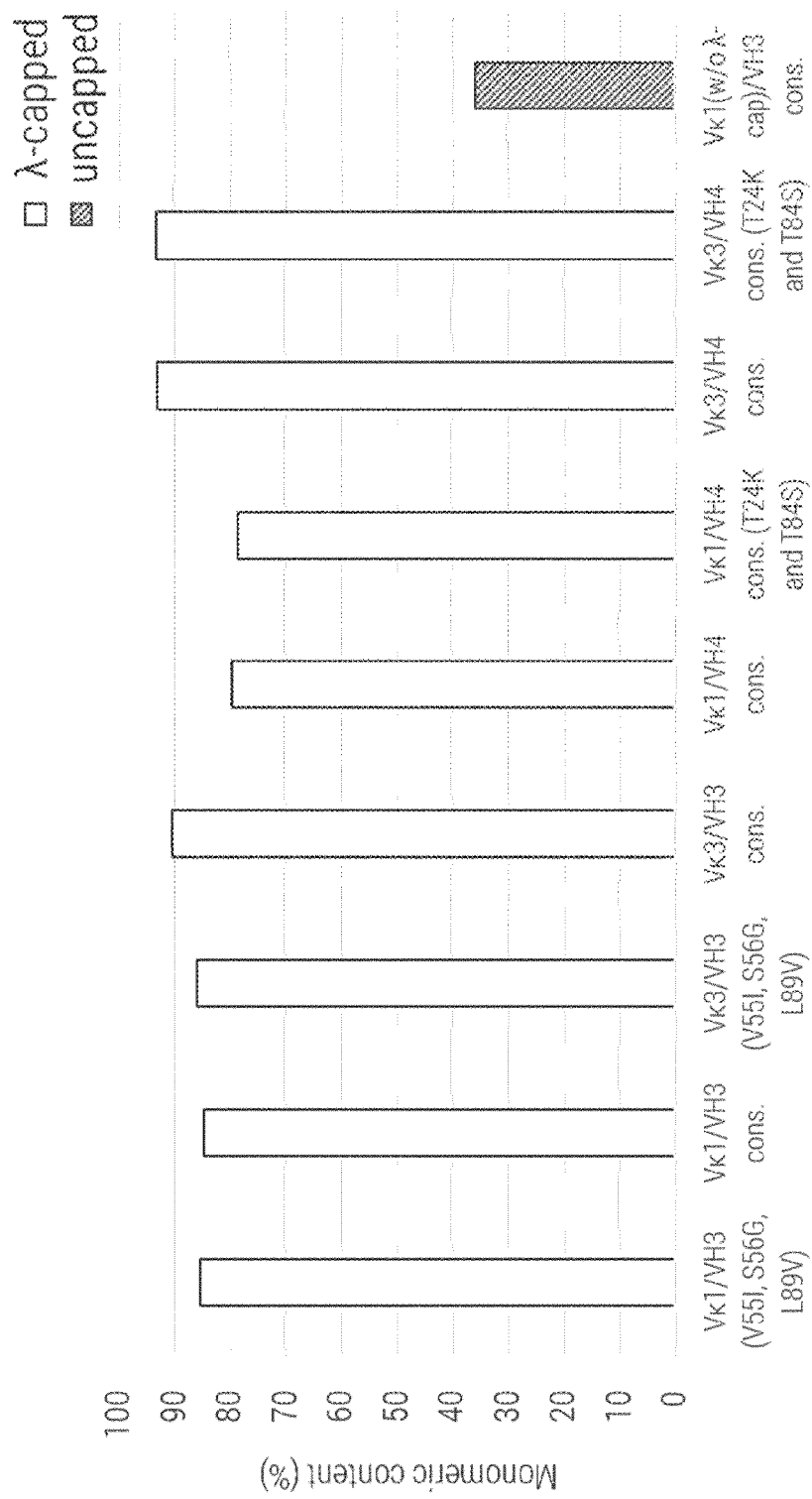
FIG. 5 shows absolute % monomeric content of TNF-specific control molecules upon storage at 10 mg/mL for 2 weeks at 37° C. for capped framework variants (white bars) and uncapped framework counterparts (grey bars).

Storage stability studies with the TNF specific molecules confirm previously observed stabilizing effects of the λ-cap as the monomeric content after two weeks storage at stress conditions was again clearly superior for all capped molecules, when compared to the monomeric content of the control molecule (Vκ1/VH3 consensus) used in this study. Overall, stability of VH4 comprising molecules was comparable to VH3 comprising molecules, with the Vκ3/VH4 framework combination being the most stable (see FIG. 5).

TABLE 3

Affinity of Vκ1(3)/VH3(4)-comprising molecules to human TNF.

| | Affinity to human TNF: | | |
|---|---|---|---|
| Protein | k$_a$ (1/Ms) | k$_d$ (1/s) | K$_D$ (M) |
| Vκ1/VH3 consensus λ-capped | 4.19E+05 | 9.41E−05 | 2.25E−10 |
| Vκ3/VH3 consensus λ-capped* | 2.90E+05 | 5.29E−04 | 1.82E−09 |
| Vκ1/VH4 consensus λ-capped | 6.31E+05 | 3.36E−05 | 5.33E−11 |
| Vκ1/VH4 consensus (T24K, T84S) λ-capped | 7.64E+05 | 3.28E−05 | 4.30E−11 |
| Vκ3/VH4 consensus λ-capped | 4.40E+05 | 5.25E−05 | 1.19E−10 |
| Vκ3/VH4 consensus (T24K, T84S) λ-capped | 3.90E+05 | 3.09E−05 | 7.93E−11 |
| Vκ1/VH3 consensus uncapped | 3.95E+05 | 1.05E−04 | 2.65E−10 |

*interference with SPR measurement

TABLE 4

Production yield of TNF-specific control molecules.

| Protein | Monomer content [%] | Yield [mg/L expression] |
|---|---|---|
| Vκ1/VH3 consensus λ-capped | >98 | 79 |
| Vκ3/VH3 consensus λ-capped* | >99 | 79 |
| Vκ1/VH4 consensus λ-capped | 100 | 10 |
| Vκ1/VH4 consensus (T24K, T84S) λ-capped | >99 | 28 |
| Vκ3/VH4 consensus λ-capped | >99 | 2 |
| Vκ3/VH4 consensus (T24K, T84S) λ-capped | >99 | 6 |
| Vκ1/VH3 consensus uncapped | >97 | 12 |

Example 4

Sk12 vs sk17 λ-cap

As shown above, in addition to the selection of the optimal VL and VH framework combination, also the incorporation of the λ-cap into VL consensus domains leads to a considerable improvement of biophysical properties of the respective scFv molecule. It appears likely, that also the various germline sequences for FW region 4 in a lambda type light chain would result in different properties when used as a λ-cap. When comparing different lambda-type FW 4 regions we identified the sequence sk17 (SEQ ID NO: 63) as particularly stable (Table 5) in the context of a Vκ1/VH3 framework combination containing a different set of TNF specific CDRs than the one used in the studies above and in WO 2014/206561. The two molecules differ only in the sequence of their λ-caps, which were termed sk12 (SEQ ID NO: 62) and sk17 (SEQ ID NO: 63). Sk17 λ-cap containing molecule outperforms sk12 λ-cap containing molecule in terms of storage stability and thermal stability.

Further evidence of superiority of the sk17 over sk12 is shown in Table 6. The same IL17-specific rabbit CDR loops were engrafted onto four different Vκ1 bearing framework combinations. Constructs 1-3 comprise the same Vκ1 with a sk17 λ-cap and different variable heavy chains (VH1A, VH4 or VH1B, correspondingly), while construct 4 comprises a Vκ1 light chain with a sk12 λ-cap and a VH3 heavy chain. All sk17 bearing molecules were superior in terms of target binding affinity than the molecule bearing the current state of the art Vκ1(sk12)/VH3 framework combination (construct 4). Further, Vκ1/VH4 (construct 2) bearing molecule exhibits superior thermal stability as the midpoint of thermal unfolding, measured by DSF measurement, is considerably increased. Therefore, sk17 seems to be particularly useful for the stabilization by lambda-capping.

TABLE 5

Comparative study of two scFv molecules disclosed in WO 2014/206561. Sk17 germline λ-cap (SEQ ID NO: 63) outperforms sk12 germline (SEQ ID NO: 62) in terms of midpoint of unfolding and monomeric content loss upon storage at a concentration of 10 mg/mL at 37° C.

| Construct | Construct ID | Tm | Monomer content loss |
|---|---|---|---|
| EP43-Sk12sh4 | scFv5 | 70.9 | −11.40% |
| EP43-Sk17sh4 | scFv9 | 71.2 | −10.10% |

TABLE 6

Superiority of sk17 λ-cap (SEQ ID NO: 63) bearing molecules over sk12 λ-cap (SEQ ID NO: 62) bearing molecules shown with IL17 specific scFv fragments.

| Construct ID | Description | Tm [° C.] | $K_D$ [M] |
|---|---|---|---|
| 1 | Vκ1(sk17)/VH1A | 66.5 | 8.7E−11 |
| 2 | Vκ1(sk17)/VH4 | 77.2 | 8.3E−11 |
| 3 | Vκ1(sk17)/VH1B | 72.3 | 8.2E−11 |
| 4 | Vκ1(sk12)/VH3 | 74.3 | 2.5E−10 |
| 5 | Vκ1(sk17)/VH3 | 74.7 | |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

To the extent possible under the respective patent law, all patents, applications, publications, test methods, literature, and other materials cited herein are hereby incorporated by reference.

TABLE 7

List of protein sequences

| SEQ ID NO: | Type | Sequence |
|---|---|---|
| 1 | VH1A | QVQLVQSGAEVKKPGSSVKVSCKAS*GIDFNSNYYMC*WVRQAPGQGLEWMG*CIYVGSHVNTYYANWAKG*RVTITADESTSTAYMELSSLRSEDTAVYYCA*TSGSSVLYFKF*WGQGTLVTVSS |
| 2 | HFW1 VH1A | QVQLVQSGAEVKKPGSSVKVSCKAS |
| 3 | HFW2 VH1A | WVRQAPGQGLEWMG |
| 4 | HFW3 VH1A | RVTITADESTSTAYMELSSLRSEDTAVYYCA |
| 5 | HFW4 VH1A | WGQGTLVTVSS |
| 6 | VH1B | QVQLVQSGAEVKKPGASVKVSCKAS*GIDFNSNYYMC*WVRQAPGQGLEWMG*CIYVGSHVNTYYANWAKG*RVTMTRDTSISTAYMELSSLRSEDTAVYYCA*TSGSSVLYFKF*WGQGTLVTVSS |
| 7 | HFW1 VH1B | QVQLVQSGAEVKKPGASVKVSCKAS |
| 8 | HFW2 VH1B | WVRQAPGQGLEWMG |
| 9 | HFW3 VH1B | RVTMTRDTSISTAYMELSSLRSEDTAVYYCA |
| 10 | HFW4 VH1B | WGQGTLVTVSS |
| 11 | VH2 | QVQLKESGPALVKPTQTLTLTCTFS*GIDFNSNYYMC*WIRQPPGKALEWLA*CIYVGSHVNTYYANWAKG*RLTISKDTSKNQVVLTMTNMDPVDTATYYCA*TSGSSVLYFKF*WGQGTLVTVSS |

TABLE 7-continued

List of protein sequences

| SEQ ID NO: | Type | Sequence |
|---|---|---|
| 12 | HFW1 VH2 | QVQLKESGPALVKPTQTLTLTCTFS |
| 13 | HFW2 VH2 | WIRQPPGKALEWLA |
| 14 | HFW3 VH2 | RLTISKDTSKNQVVLTMTNMDPVDTATYYCA |
| 15 | HFW4 VH2 | WGQGTLVTVSS |
| 16 | VH3 | EVQLVESGGGLVQPGGSLRLSCAAS*GIDFNSNYYMC*WVRQAPGKGLEWVS*CIYVGSHVNTYYANWAKG*RFTISRDNSKNTLYLQMNSLRAEDTAVYYCA*TSGSSVLYFKF*WGQGTLVTVSS |
| 17 | HFW1 VH3 | EVQLVESGGGLVQPGGSLRLSCAAS |
| 18 | HFW2 VH3 | WVRQAPGKGLEWVS |
| 19 | HFW3 VH3 | RFTISRDNSKNTLYLQMNSLRAEDTAVYYCA |
| 20 | HFW4 VH3 | WGQGTLVTVSS |
| 21 | VH4 | QVQLQESGPGLVKPSETLSLTCTVS*GIDFNSNYYMC*WIRQPPGKGLEWIG*CIYVGSHVNTYYANWAKG*RVTISVDTSKNQFSLKLSSVTAADTAVYYCA*TSGSSVLYFKF*WGQGTLVTVSS |
| 22 | HFW1 VH4 | QVQLQESGPGLVKPSETLSLTCTVS |
| 23 | HFW2 VH4 | WIRQPPGKGLEWIG |
| 24 | HFW3 VH4 | RVTISVDTSKNQFSLKLSSVTAADTAVYYCA |
| 25 | HFW4 VH4 | WGQGTLVTVSS |
| 26 | VH4$_{mut}$ | QVQLQESGPGLVKPSETLSLTCKVS*GIDFNSNYYMC*WIRQPPGKGLEWIG*CIYVGSHVNTYYANWAKG*RVTISVDSSKNQFSLKLSSVTAADTAVYYCA*TSGSSVLYFKF*WGQGTLVTVSS |
| 27 | HFW1 VH4$_{mut}$ | QVQLQESGPGLVKPSETLSLTCKVS |
| 28 | HFW2 VH4$_{mut}$ | WIRQPPGKGLEWIG |
| 29 | HFW3 VH4$_{mut}$ | RVTISVDSSKNQFSLKLSSVTAADTAVYYCA |
| 30 | HFW4 VH4$_{mut}$ | WGQGTLVTVSS |
| 31 | VH5 | EVQLVQSGAEVKKPGESLKISCKGS*GIDFNSNYYMC*WVRQMPGKGLEWMG*CIYVGSHVNTYYANWAKG*QVTISADKSISTAYLQWSSLKASDTAMYYCA*TSGSSVLYFKF*WGQGTLVTVSS |
| 32 | HFW1 VH5 | EVQLVQSGAEVKKPGESLKISCKGS |
| 33 | HFW2 VH5 | CIYVGSHVNTYYANWAKG |
| 34 | HFW3 VH5 | QVTISADKSISTAYLQWSSLKASDTAMYYCA |
| 35 | HFW4 VH5 | WGQGTLVTVSS |
| 36 | VH6 | QVQLQQSGPGLVKPSQTLSLTCAIS*GIDFNSNYYMC*WIRQSPGRGLEWLG*CIYVGSHVNTYYANWAKG*RITINPDTSKNQFSLQLNSVTPEDTAVYYCA*TSGSSVLYFKF*WGQGTLVTVSS |
| 37 | HFW1 VH6 | QVQLQQSGPGLVKPSQTLSLTCAIS |
| 38 | HFW2 VH6 | WIRQSPGRGLEWLG |
| 39 | HFW3 VH6 | RITINPDTSKNQFSLQLNSVTPEDTAVYYCA |
| 40 | HFW4 VH6 | WGQGTLVTVSS |

TABLE 7-continued

List of protein sequences

| SEQ ID NO: | Type | Sequence |
|---|---|---|
| 41 | Vκ1 uncapped | DIQMTQSPSSLSASVGDRVTITC*QASENIYSFLA*WYQQKPGKAPKLLIY*SASKLAA*GVPSRFSGSGSGTDFTLTISSLQPEDFATYYC*QQTNRYSNPDIYNV*FGQGTKVEIKR |
| 42 | LFW1 Vκ1 | DIQMTQSPSSLSASVGDRVTITC |
| 43 | LFW2 Vκ1 | WYQQKPGKAPKLLIY |
| 44 | LFW3 Vκ1 | GVPSRFSGSGSGTDFTLTISSLQPEDFATYYC |
| 45 | LFW4 Vκ1 | FGQGTKVEIKR |
| 46 | Vκ2 uncapped | DIVMTQSPLSLPVTPGEPASISC*QASENIYSFLA*WYLQKPGQSPQLLIY*SASKLAA*GVPDRFSGSGSGTDFTLKISRVEAEDVGVYYC*QQTNRYSNPDIYNV*FGQGTKVEIKR |
| 47 | LFW1 Vκ2 | DIVMTQSPLSLPVTPGEPASISC |
| 48 | LFW2 Vκ2 | WYLQKPGQSPQLLIY |
| 49 | LFW3 Vκ2 | GVPDRFSGSGSGTDFTLKISRVEAEDVGVYYC |
| 50 | LFW4 Vκ2 | FGQGTKVEIKR |
| 51 | Vκ3 uncapped | DIVLTQSPATLSLSPGERATLSC*QASENIYSFLA*WYQQKPGQAPRLLIY*SASKLAA*GVPARFSGSGSGTDFTLTISSLEPEDFAVYYC*QQTNRYSNPDIYNV*FGQGTKVEIKR |
| 52 | LFW1 Vκ3 | DIVLTQSPATLSLSPGERATLSC |
| 53 | LFW2 Vκ3 | WYQQKPGQAPRLLIY |
| 54 | LFW3 Vκ3 | GVPARFSGSGSGTDFTLTISSLEPEDFAVYYC |
| 55 | LFW4 Vκ3 | FGQGTKVEIKR |
| 56 | Vκ1 sk12-capped | DIQMTQSPSSLSASVGDRVTITC*QASENIYSFLA*WYQQKPGKAPKLLIY*SASKLAA*GVPSRFSGSGSGTDFTLTISSLQPEDFATYYC*QQTNRYSNPDIYNV*FGGGTKLTVLG |
| 57 | Vκ1 sk17-capped | DIQMTQSPSSLSASVGDRVTITC*QASENIYSFLA*WYQQKPGKAPKLLIY*SASKLAA*GVPSRFSGSGSGTDFTLTISSLQPEDFATYYC*QQTNRYSNPDIYNV*FGTGTKVTVLG |
| 58 | Vκ2 sk12-capped | DIVMTQSPLSLPVTPGEPASISC*QASENIYSFLA*WYLQKPGQSPQLLIY*SASKLAA*GVPDRFSGSGSGTDFTLKISRVEAEDVGVYYC*QQTNRYSNPDIYNV*FGGGTKLTVLG |
| 59 | Vκ2 sk17-capped | DIVMTQSPLSLPVTPGEPASISC*QASENIYSFLA*WYLQKPGQSPQLLIY*SASKLAA*GVPDRFSGSGSGTDFTLKISRVEAEDVGVYYC*QQTNRYSNPDIYNV*FGTGTKVTVLG |
| 60 | Vκ3 sk12-capped | DIVLTQSPATLSLSPGERATLSC*QASENIYSFLA*WYQQKPGQAPRLLIY*SASKLAA*GVPARFSGSGSGTDFTLTISSLEPEDFAVYYC*QQTNRYSNPDIYNV*FGGGTKLTVLG |
| 61 | Vκ3 sk17-capped | DIVLTQSPATLSLSPGERATLSC*QASENIYSFLA*WYQQKPGQAPRLLIY*SASKLAA*GVPARFSGSGSGTDFTLTISSLEPEDFAVYYC*QQTNRYSNPDIYNV*FGTGTKVTVLG |
| 62 | sk12 | FGGGTKLTVLG |
| 63 | sk17 | FGTGTKVTVLG |
| 64 | Linker | GGGGSGGGSGGGGSGGGGS |
| 65 | Linker | GGGGSGGGGSGGGGS |
| 66 | LCDR1 IL23R | QASENIYSFLA |
| 67 | LCDR2 IL23R | SASKLAA |

TABLE 7-continued

List of protein sequences

| SEQ ID NO: | Type | Sequence |
|---|---|---|
| 68 | LCDR3 IL23R | QQTNRYSNPDIYNV |
| 69 | HCDR1 IL23R | GIDFNSNYYMC |
| 70 | HCDR2 IL23R | CIYVGSHVNTYYANWAKG |
| 71 | HCDR3 IL23R | TSGSSVLYFKF |
| 72 | LCDR1 TNF | QASQSISDWLA |
| 73 | LCDR2 TNF | GASRLAS |
| 74 | LCDR3 TNF | QQGWSDSYVDNL |
| 75 | HCDR1 TNF | GFSLSSGAMS |
| 76 | HCDR2 TNF | VIISSGATYYASWAKG |
| 77 | HCDR3 TNF | RGGPDDSNSMGTFDP |
| 78 | VH4$_{mut}$ TNF | QVQLQESGPGLVKPSETLSLTCKVS*GFSLSSGAMS*WIR QPPGKGLEWIG*VIISSGATYYASWAKG*RVTISVDSSKNQ FSLKLSSVTAADTAVYYCA*RGGPDDSNSMGTFDP*WGQ GTLVTVSS |
| 79 | Sk12-Cys | FGCGTKLTVLG |
| 80 | Sk17-Cys | FGCGTKVTVLG |
| 81 | Vκ4 | DIVMTQSPDSLAVSLGERATINC*QASENIYSFLA*WYQQK PGQPPKLLIY*SASKLAA*GVPDRFSGSGSGTDFTLTISSL QAEDVAVYYC*QTNRYSNPDIYNV*FGQGTKVEIKR |

(in SEQ ID NOs: 1 to 81, the CDRs are indicated in bold and italic letters)

TABLE 8

| SEQ ID NO | Chain | Target | Description | FW_1 | CDR_L1 | FW_2 | CDR_L2 |
|---|---|---|---|---|---|---|---|
| 56 | Light | IL23R | VK1_consensus_capped | DIQMTQSPSSLSASVGDRVTITC | QASENIYSFLA | WYQQKPGKAPKLLIY | SASKLAA |
| 58 | | IL23R | VK2_consensus_capped | DIVMTQSPLSLPVTPGEPASISC | QASENIYSFLA | WYLQKPGQSPQLLIY | SASKLAA |
| 60 | | IL23R | VK3_consensus_capped | DIVLTQSPATLSLSPGERATLSC | QASENIYSFLA | WYQQKPGQAPRLLIY | SASKLAA |
| 41 | | IL23R | VK1_consensus_uncapped | DIQMTQSPSSLSASVGDRVTITC | QASENIYSFLA | WYQQKPGKAPKLLIY | SASKLAA |
| 46 | | IL23R | VK2_consensus_uncapped | DIVMTQSPLSLPVTPGEPASISC | QASENIYSFLA | WYLQKPGQSPQLLIY | SASKLAA |
| 51 | | IL23R | VK3_consensus_uncapped | DIVLTQSPATLSLSPGERATLSC | QASENIYSFLA | WYQQKPGQAPRLLIY | SASKLAA |
| 82 | | TNF | VK1_consensus_capped | DIQMTQSPSSLSASVGDRVTITC | QASQSISDWLA | WYQQKPGKAPKLLIY | GASRLAS |
| 85 | | TNF | VK3_consensus_capped | DIVLTQSPATLSLSPGERATLSC | QASQSISDWLA | WYQQKPGQAPRLLIY | GASRLAS |

| SEQ ID NO | Chain | Target | Description | FW_1 | CDR_H1 | FW_2 | CDR_H2 |
|---|---|---|---|---|---|---|---|
| 1 | Heavy | IL23R | VH1A_consensus | QVQLVQSGAEVKKPGSSVKVSCKAS | GIDFNSNYYMC | WVRQAPGQGLEWMG | CIYVGSHVNTYYANWAKG |
| 6 | | IL23R | VH1B_consensus | QVQLVQSGAEVKKPGASVKVSCKAS | GIDFNSNYYMC | WVRQAPGQGLEWMG | CIYVGSHVNTYYANWAKG |
| 11 | | IL23R | VH2_consensus | QVQLKESGPALVKPTQTLTLTCTFS | GIDFNSNYYMC | WIRQPPGKALEWLA | CIYVGSHVNTYYANWAKG |
| 16 | | IL23R | VH3_consensus | EVQLVESGGGLVQPGGSLRLSCAAS | GIDFNSNYYMC | WVRQAPGKGLEWVS | CIYVGSHVNTYYANWAKG |
| 21 | | IL23R | VH4_consensus | QVQLQESGPGLVKPSETLSLTCTVS | GIDFNSNYYMC | WIRQPPGKGLEWIG | CIYVGSHVNTYYANWAKG |
| 26 | | IL23R | VH4_consensus (T24K, T84S) | QVQLQESGPGLVKPSETLSLTCKVS | GIDFNSNYYMC | WIRQPPGKGLEWIG | CIYVGSHVNTYYANWAKG |
| 31 | | IL23R | VH5_consensus | EVQLVQSGAEVKKPGESLKISCKGS | GIDFNSNYYMC | WVRQMPGKGLEWMG | CIYVGSHVNTYYANWAKG |
| 36 | | IL23R | VH6_consensus | QVQLQQSGPGLVKPSQTLSLTCAIS | GIDFNSNYYMC | WIRQSPGRGLEWLG | CIYVGSHVNTYYANWAKG |
| 83 | | TNF | VH3_consensus | EVQLVESGGGLVQPGGSLRLSCAAS | GFSLSSSGAMS | WVRQAPGKGLEWVS | VIISSGATYYASWAKG |
| 84 | | TNF | VH4_consensus | QVQLQESGPGLVKPSETLSLTCTVS | GFSLSSSGAMS | WIRQPPGKGLEWIG | VIISSGATYYASWAKG |
| 78 | | TNF | VH4_consensus (T24K, T84S) | QVQLQESGPGLVKPSETLSLTCKVS | GFSLSSSGAMS | WIRQPPGKGLEWIG | VIISSGATYYASWAKG |
| 62 | | NA | sk12 λ-cap sequence | NA | NA | NA | NA |
| 79 | | NA | sk12-Cys λ-cap sequence | NA | NA | NA | NA |
| 63 | | NA | sk17 λ-cap sequence | NA | NA | NA | NA |
| 60 | | NA | sk17-Cys λ-cap sequence | NA | NA | NA | NA |

TABLE 8-continued

| | Chain | FW_3 | CDR_L3 | FW_4 |
|---|---|---|---|---|
| 56 | Light | GVPSRFSGSGSGTDFTLTISSLQPEDFATYYC | QQTNRYSNPDIYNV | FGGGTKLTVLG |
| 58 | | GVPDRFSGSGSGTDFTLKISRVEAEDVGVYYC | QQTNRYSNPDIYNV | FGGGTKLTVLG |
| 60 | | GVPARFSGSGSGTDFTLTISSLPEDVGVYYC | QQTNRYSNPDIYNV | FGGGTKLTVLG |
| 41 | | GVPSRFSGSGSGTDFTLTISSLQPEDFATYYC | QQTNRYSNPDIYNV | FGQGTKVEIKR |
| 46 | | GVPDRFSGSGSGTDFTLKISRVEAEDVGVYYC | QQTNRYSNPDIYNV | FGQGTKVEIKR |
| 51 | | GVPARFSGSGSGTDFTLTISSLEPEDFAVYYC | QQTNRYSNPDIYNV | FGQGTKLTVLG |
| 82 | | GVPSRFSGSGSGTDFTLTISSLQPEDFATYYC | QQGWSDSYVDNL | FGGGTKLTVLG |
| 85 | | GVPARFSGSGSGTDFTLTISSLEPEDFAVYYC | QQGWSDSYVDNL | FGGGTKLTVLG |

| | Chain | FW_3 | CDR_H3 | FW_4 |
|---|---|---|---|---|
| 1 | Heavy | RVTITADESTSTAYMELSSLRSEDTAVYYCA | TSGSSVLYFKF | WGQGTLVTVSS |
| 6 | | RVTMTRDTSISTAYMELSSLRSEDTAVYYCA | TSGSSVLYFKF | WGQGTLVTVSS |
| 11 | | RLTISKDTSKNQVVLTMTNMDPVDTATYYCA | TSGSSVLYFKF | WGQGTLVTVSS |
| 16 | | RFTISRDNSKNTLYLQMNSLRAEDTAVYYCA | TSGSSVLYFKF | WGQGTLVTVSS |
| 21 | | RVTISVDTSKNQFSLKLSSVTAADTAVYYCA | TSGSSVLYFKF | WGQGTLVTVSS |
| 26 | | RVTISVDTSKNQFSLKLSSVTAADTAVYYCA | TSGSSVLYFKF | WGQGTLVTVSS |
| 31 | | QVTISADKSISTAYLQWSSLKASDTAMYYCA | TSGSSVLYFKF | WGQGTLVTVSS |
| 36 | | RITINPDTSKNQFSLQLNSVTPEDTAVYYCA | TSGSSVLYFKF | WGQGTLVTVSS |
| 83 | | RFTISRDNSKNTLYLQMNSLRAEDTAVYYCA | RGGPDDSNSMGTFDP | WGQGTLVTVSS |
| 84 | | RVTISVDTSKNQFSLKLSSVTAADTAVYYCA | RGGPDDSNSMGTFDP | WGQGTLVTVSS |
| 78 | | RVTISVDSSKNQFSLKLSSVTAADTAVYYCA | RGGPDDSNSMGTFDP | WGQGTLVTVSS |
| 62 | | NA | NA | FGGGTKLTVLG |
| 79 | | NA | NA | FGCGTKLTVLG |
| 63 | | NA | NA | FGTGTKVTVLG |
| 60 | | NA | NA | FGCGTKVTVLG |

The invention claimed is:

1. An antibody or functional fragment thereof comprising:
   (a) a variable light chain,
      wherein the variable light chain comprises, from N-terminus to C-terminus, the regions LFW1-LCDR1-LFW2-LCDR2-LFW3-LCDR3-LFW4, wherein each LFW designates a light chain framework region, and each LCDR designates a light chain complementarity-determining region, and wherein:
      (i) said LFW1, LFW2, and LFW3 regions together exhibit at least 95% sequence identity to the corresponding framework regions of the Vκ1 sequence according to SEQ ID NO: 41; or to the corresponding framework regions of the Vκ3 sequence according to SEQ ID NO: 51; and
      (ii) said LFW4 is a Vλ-based sequence which is at least 90% identical to SEQ ID NO: 63; and
   (b) a variable heavy chain, wherein the variable heavy chain comprises, from N-terminus to C-terminus, the regions HFW1-HCDR1-HFW2-HCDR2-HFW3-HCDR3-HFW4, wherein each HFW designates a heavy chain framework region, and each HCDR designates a heavy chain complementarity-determining region, and wherein said HFW1, HFW2, HFW3, and HFW4 regions together exhibit at least 93% sequence identity to the corresponding framework regions of the VH4 sequence according to SEQ ID NO: 21, or to the corresponding framework regions of the VH1A sequence according to SEQ ID NO: 1.

2. The antibody or functional fragment thereof according to claim 1, wherein the variable heavy chain comprises HFW1, HFW2, HFW3, and HFW4 regions of the VH1A sequence according to SEQ ID NO: 1, or of the VH1B sequence according to SEQ ID NO: 6, or of the VH4 sequence according to SEQ ID NO: 21, or of the VH4$_{mut}$ sequence according to SEQ ID NO: 26.

3. The antibody or functional fragment thereof according to claim 1, wherein the variable light chain comprises LFW1, LFW2, and LFW3 regions of the Vκ1 sequence according to SEQ ID NO: 41, or of the Vκ3 sequence according to SEQ ID NO: 51.

4. The antibody or functional fragment thereof according to claim 1, wherein said HFW1, HFW2, HFW3, and HFW4 regions together exhibit at least 95% sequence identity to the corresponding framework regions of the VH4 sequence according to SEQ ID NO: 21, and wherein said LFW1, LFW2, and LFW3 regions together exhibit at least 95% sequence identity to the corresponding framework regions of the Vκ1 sequence according to SEQ ID NO: 41.

5. The antibody or functional fragment thereof according to claim 1, wherein said HFW1, HFW2, HFW3, and HFW4 regions together exhibit at least 95% sequence identity to the corresponding framework regions of the VH4 sequence according to SEQ ID NO: 21, and wherein said LFW1, LFW2, and LFW3 regions together exhibit at least 95% sequence identity to the corresponding framework regions of the Vκ3 sequence according to SEQ ID NO: 51.

6. The antibody or functional fragment thereof according to claim 1, wherein said HFW1, HFW2, HFW3, and HFW4 regions together exhibit at least 93% sequence identity to the corresponding framework regions of the VH1A sequence according to SEQ ID NO: 1, and wherein said LFW1, LFW2, and LFW3 regions together exhibit at least 95% sequence identity to the corresponding framework regions of the Vκ1 sequence according to SEQ ID NO: 41.

7. The antibody or functional fragment thereof according to claim 1, wherein said HFW1, HFW2, HFW3, and HFW4 regions together exhibit at least 93% sequence identity to the corresponding framework regions of the VH1A sequence according to SEQ ID NO: 1, and wherein said LFW1, LFW2, and LFW3 regions together exhibit at least 95% sequence identity to the corresponding framework regions of the Vκ3 sequence according to SEQ ID NO: 51.

8. The antibody or functional fragment thereof of claim 1, wherein said CDR domains HCDR1, HCDR2, HCDR3, LCDR1, LCDR2 and LCDR3 are selected from (i) CDR domains HCDR1, HCDR2, HCDR3, LCDR1, LCDR2 and LCDR3 from a parental non-human antibody with specificity for an antigen of interest; (ii) CDR domains HCDR1, HCDR2, HCDR3, LCDR1, LCDR2 and LCDR3 from a parental human or humanized antibody comprising a Vκ domain; (iii) CDR domains HCDR1, HCDR2, HCDR3, LCDR1, LCDR2 and LCDR3 derived from the CDR domains according to (i) or (ii); and (iv) a CDR domain to be replaced by one or more CDR domains according to (i), (ii) and/or (iii).

9. A pharmaceutical composition comprising the antibody or functional fragment thereof of claim 1, and optionally a pharmaceutically acceptable carrier and/or excipient.

10. The antibody or functional fragment thereof according to claim 1, wherein said LFW4 has the sequence as set forth in SEQ ID NO: 63.

11. The antibody or functional fragment thereof according to claim 2, wherein the variable heavy chain comprises:
    (a) HFW1 as set forth in SEQ ID NO: 2, HFW2 as set forth in SEQ ID NO: 3, HFW3 as set forth in SEQ ID NO: 4, and HFW4 as set forth in SEQ ID NO: 5;
    or
    (b) HFW1 as set forth in SEQ ID NO: 7, HFW2 as set forth in SEQ ID NO: 8, HFW3 as set forth in SEQ ID NO: 9, and HFW4 as set forth in SEQ ID NO: 10;
    or
    (c) HFW1 as set forth in SEQ ID NO: 22, HFW2 as set forth in SEQ ID NO: 23, HFW3 as set forth in SEQ ID NO: 24, and HFW4 as set forth in SEQ ID NO: 25;
    or
    (d) HFW1 as set forth in SEQ ID NO: 27, HFW2 as set forth in SEQ ID NO: 28, HFW3 as set forth in SEQ ID NO: 29, and HFW4 as set forth in SEQ ID NO: 30.

12. The antibody or functional fragment thereof according to claim 3, wherein the variable light chain comprises:
    (a) LFW1 as set forth in SEQ ID NO: 42, LFW2 as set forth in SEQ ID NO: 43, and LFW3 as set forth in SEQ ID NO: 44;
    or
    (b) LFW1 as set forth in SEQ ID NO: 52, LFW2 as set forth in SEQ ID NO: 53, and LFW3 as set forth in SEQ ID NO: 54.

13. The antibody or functional fragment thereof according to claim 4,
    wherein the variable heavy chain comprises HFW1 as set forth in SEQ ID NO: 22, HFW2 as set forth in SEQ ID NO: 23, HFW3 as set forth in SEQ ID NO: 24, and HFW4 as set forth in SEQ ID NO: 25; and the variable light chain comprises LFW1 as set forth in SEQ ID NO: 42, LFW2 as set forth in SEQ ID NO: 43, and LFW3 as set forth in SEQ ID NO: 44, or
    wherein the variable heavy chain comprises HFW1 as set forth in SEQ ID NO: 27, HFW2 as set forth in SEQ ID NO: 28, HFW3 as set forth in SEQ ID NO: 29, and HFW4 as set forth in SEQ ID NO: 30; and the variable light chain comprises LFW1 as set forth in SEQ ID NO: 42, LFW2 as set forth in SEQ ID NO: 43, and LFW3 as set forth in SEQ ID NO: 44.

14. The antibody or functional fragment thereof according to claim 5,
    wherein the variable heavy chain comprises HFW1 as set forth in SEQ ID NO: 22, HFW2 as set forth in SEQ ID NO: 23, HFW3 as set forth in SEQ ID NO: 24, and HFW4 as set forth in SEQ ID NO: 25; and the variable light chain comprises LFW1 as set forth in SEQ ID NO: 52, LFW2 as set forth in SEQ ID NO: 53, and LFW3 as set forth in SEQ ID NO: 54, or
    wherein the variable heavy chain comprises HFW1 as set forth in SEQ ID NO: 27, HFW2 as set forth in SEQ ID NO: 28, HFW3 as set forth in SEQ ID NO: 29, and HFW4 as set forth in SEQ ID NO: 30; and the variable light chain comprises LFW1 as set forth in SEQ ID NO: 52, LFW2 as set forth in SEQ ID NO: 53, and LFW3 as set forth in SEQ ID NO: 54.

15. The antibody or functional fragment thereof according to claim 6,
  wherein the variable heavy chain comprises HFW1 as set forth in SEQ ID NO: 2, HFW2 as set forth in SEQ ID NO: 3, HFW3 as set forth in SEQ ID NO: 4, and HFW4 as set forth in SEQ ID NO: 5; and the variable light chain comprises LFW1 as set forth in SEQ ID NO: 42, LFW2 as set forth in SEQ ID NO: 43, and LFW3 as set forth in SEQ ID NO: 44, or
  wherein the variable heavy chain comprises HFW1 as set forth in SEQ ID NO: 7, HFW2 as set forth in SEQ ID NO: 8, HFW3 as set forth in SEQ ID NO: 9, and HFW4 as set forth in SEQ ID NO: 10; and the variable light chain comprises LFW1 as set forth in SEQ ID NO: 42, LFW2 as set forth in SEQ ID NO: 43, and LFW3 as set forth in SEQ ID NO: 44.

16. The antibody or functional fragment thereof according to claim 7,
  wherein the variable heavy chain comprises HFW1 as set forth in SEQ ID NO: 2, HFW2 as set forth in SEQ ID NO: 3, HFW3 as set forth in SEQ ID NO: 4, and HFW4 as set forth in SEQ ID NO: 5; and the variable light chain comprises LFW1 as set forth in SEQ ID NO: 52, LFW2 as set forth in SEQ ID NO: 53, and LFW3 as set forth in SEQ ID NO: 54, or
  wherein the variable heavy chain comprises HFW1 as set forth in SEQ ID NO; 7, HFW2 as set forth in SEQ ID NO: 8, HFW3 as set forth in SEQ ID NO: 9, and HFW4 as set forth in SEQ ID NO; 10; and the variable light chain comprises LFW1 as set forth in SEQ ID NO: 52, LFW2 as set forth in SEQ ID NO: 53, and LFW3 as set forth in SEQ ID NO: 54.

17. The antibody or functional fragment thereof according to claim 8, wherein said CDR domains HCDR1, HCDR2, HCDR3, LCDR1, LCDR2 and LCDR3 are selected from (i) CDR domains HCDR1, HCDR2, HCDR3, LCDR1, LCDR2 and LCDR3 from a parental rabbit antibody or from a parental mouse or rat antibody; (ii) CDR domains HCDR1, HCDR2, HCDR3, LCDR1, LCDR2 and LCDR3 from a parental human or humanized antibody comprising a Vκ domain from an antibody approved for therapy or otherwise being commercialized; or (iii) CDR domains obtained by optimizing one or more of the CDR domains according to (i) or (ii) of claim 8.

18. A method for humanizing a non-human antibody comprising the step of:
  (a) translating the sequence of the antibody or functional fragment thereof according to claim 1 into one or more nucleic acid sequences encoding said antibody or functional fragment thereof;
  (b) cloning, in one or more steps, nucleic acid sequences encoding variable heavy chain (VH) CDRs and variable light chain (VL) CDRs of said non-human antibody into said one or more nucleic acid sequences, provided that at least the VH CDR3 and the VL CDR3 of said non-human antibody are cloned, optionally further comprising the cloning of the VH CDR2 and/or VL CDR1, optionally further comprising the cloning of the VH CDR1 and/or the VL CDR2,
  optionally further comprising one or more of the steps of:
  (aa) immunization of non-human animal with an antigen of interest; and
  (ab) isolating at least one antibody of interest optionally further comprising one or more of the steps of:
  (ac) clonal isolation of affinity-matured memory B-cells that interact with the antigen of interest;
  (ad) cultivation of single B cells in a co-cultivation system that does not require immortalization of single B cell clones;
  (ae) screening of B cell culture supernatants in a cell-based ELISA to identify at least one antibody binding to the antigen of interest; and/or
  (af) cloning of the VH CDRs of at least one antibody into a nucleic acid sequence encoding a human antibody VH domain.

19. The method according to claim 18, wherein said non-human antibody is a rabbit or rodent antibody, and wherein said optional step (aa) comprises immunization of a rabbit or rodent.

20. The method according to claim 18, wherein said step (b) comprises the cloning of both the VH CDR2 and the VL CDR1 and/or optionally further comprises the cloning of both the VH CDR1 and the VL CDR2.

21. The method according to claim 18, wherein in said step (ac) said affinity-matured memory B-cells are isolated by using fluorescence activated cell-sorting.

22. The method according to claim 18,
  wherein the framework regions of said non-human antibody together have the highest degree of homology to the corresponding framework regions of a combination of a human VH family selected from VH1A (SEQ ID NO: 1), VH1B (SEQ ID NO: 6), VH4 (SEQ ID NO: 21) and VH4$_{mut}$ (SEQ ID NO: 26), and a human VL family selected from Vκ1 (SEQ ID NO: 41) and Vκ3 (SEQ ID NO: 51), or
  wherein the framework regions of said non-human antibody together have the highest degree of homology to
    (i) the framework regions of a combination of a human VH family selected from VH2 (SEQ ID NO: 11), VH3 (SEQ ID NO: 16), VH5 (SEQ ID NO: 31) and VH6 (SEQ ID NO: 36), and a human VL family selected from Vκ1 (SEQ ID NO: 41), Vκ2 (SEQ ID NO: 46), Vκ3 (SEQ ID NO: 51) and Vκ4 (SEQ ID NO: 81); or
    (ii) the framework regions of a combination of a human VH family selected from VH1A (SEQ ID NO: 1), VH1B (SEQ ID NO: 6), VH2 (SEQ ID NO: 11), VH3 (SEQ ID NO: 16), VH4 (SEQ ID NO: 21), VH4$_{mut}$ (SEQ ID NO: 26), VH5 (SEQ ID NO: 31) and VH6 (SEQ ID NO: 36), and a human VL family selected from Vκ2 (SEQ ID NO: 46) and Vκ4 (SEQ ID NO: 81), or
  wherein the framework regions of said non-human antibody together have the highest degree of homology to the corresponding framework regions of a combination of a human VH family selected from VH2 (SEQ ID NO: 11), VH3 (SEQ ID NO: 16), VH5 (SEQ ID NO: 31) and VH6 (SEQ ID NO: 36), and a human VL family selected from Vκ2 (SEQ ID NO: 46) and Vκ4 (SEQ ID NO: 79).

23. A method for optimizing a parental antibody of interest, comprising the step of:
  (a) translating the sequence of the antibody or functional fragment thereof according to claim 1 into one or more nucleic acid sequences encoding said antibody or functional fragment thereof;
  (b) cloning, in one or more steps, nucleic acid sequences encoding VH CDRs and VL CDRs of said parental antibody into said one or more nucleic acid sequences, provided that at least the VH CDR3 and the VL CDR3 of said parental antibody are cloned, optionally further comprising the cloning of the VH CDR2 and/or the VL CDR1, optionally further comprising the cloning of the VH CDR1 and/or the VL CDR2.

24. The method according to claim 23,
wherein the framework regions of said parental antibody overall have the highest degree of homology to the corresponding framework regions of a combination of a human VH family selected from VH1A (SEQ ID NO: 1), VH1B (SEQ ID NO: 6), VH4 (SEQ ID NO: 21) and VH4$1_{mut}$ (SEQ ID NO: 26), and a human VL family selected from Vκ1 (SEQ ID NO: 41) and Vκ3 (SEQ ID NO: 51), or
wherein the framework regions of said parental antibody overall have the highest degree of homology to
   (i) the framework regions of a combination of a human VH family selected from VH2 (SEQ ID NO: 11), VH3 (SEQ ID NO: 16), VH5 (SEQ ID NO: 31) and VH6 (SEQ ID NO: 36), and a human VL family selected from Vκ1 (SEQ ID NO: 41 Vκ2 (SEQ ID NO: 46), Vκ3 (SEQ ID NO: 51) and Vκ4 (SEQ ID NO: 81); or
   (ii) the framework regions of a combination of a human VH family selected from VH1A (SEQ ID NO: 1), VH1B (SEQ ID NO: 6), VH2 (SEQ ID NO: 11), VH3 (SEQ ID NO: 16), VH4 (SEQ ID NO: 21), VH$4_{mut}$ (SEQ ID NO: 26), VH5 (SEQ ID NO: 31) and VH6 (SEQ ID NO: 36), and a human VL family selected from Vκ2 (SEQ ID NO: 46) and Vκ4 (SEQ ID NO: 81), or
wherein the framework regions of said parental antibody overall have the highest degree of homology to the corresponding framework regions of a combination of a human VH family selected from VH2 (SEQ ID NO: 11), VH3 (SEQ ID NO: 16), VH5 (SEQ ID NO: 31) and VH6 (SEQ ID NO: 36), and a human VL family selected from Vκ2 (SEQ ID NO: 46) and Vκ4 (SEQ ID NO: 79).

25. The method according to claim 23, wherein said step (b) comprises the cloning of both the VH CDR2 and the VL CDR1 and/or optionally further comprises the cloning of both the VH CDR1 and the VL CDR2.

26. A method of generating a diverse collection of antibodies or functional fragments thereof, comprising the step of
   (a) translating the sequence of the antibody or functional fragment thereof according to claim 1 into one or more nucleic acid sequences encoding said antibody or functional fragment thereof;
   (b) cloning, in one or more steps, one or more diverse collections of nucleic acid sequences encoding one or more diverse collections of VH CDRs and/or VL CDRs into said one or more nucleic acid sequences encoding the antibody or functional fragment thereof according to claim 1, optionally wherein a diverse collection of nucleic acid sequences encoding a diverse collection of VH CDR3s is cloned, optionally wherein a diverse collection of nucleic acid sequences encoding a diverse collection of VL CDR3s is cloned.

27. The method according to claim 26,
wherein a diverse collection of nucleic acid sequences encoding a diverse collection of VH CDR2s and/or a diverse collection of nucleic acid sequences encoding a diverse collection of VL CDR1s are cloned, and/or
wherein a diverse collection of nucleic acid sequences encoding a diverse collection of VH CDR1s and/or a diverse collection of nucleic acid sequences encoding a diverse collection of VL CDR2s are cloned.

28. The method according to claim 27, wherein both a diverse collection of VH CDR2s and a diverse collection of VL CDR1s; and/or both a diverse collection of VH CDR1s and a diverse collection of VL CDR2s are cloned.

* * * * *

SEQUENCE LISTING

<160> NUMBER OF SEQ ID NOS: 85

<210> SEQ ID NO 1
<211> LENGTH: 121
<212> TYPE: PRT
<213> ORGANISM: artificial sequence
<220> FEATURE:
<223> OTHER INFORMATION: artificial antibody variable domain

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Ile Asp Phe Asn Ser Asn
            20                  25                  30

Tyr Tyr Met Cys Trp Val Arg Gln Ala Pro Gly Gln Gly Leu Glu Trp
        35                  40                  45

Met Gly Cys Ile Tyr Val Gly Ser His Val Asn Thr Tyr Tyr Ala Asn
    50                  55                  60

Trp Ala Lys Gly Arg Val Thr Ile Thr Ala Asp Glu Ser Thr Ser Thr
65                  70                  75                  80

Ala Tyr Met Glu Leu Ser Ser Leu Arg Ser Glu Asp Thr Ala Val Tyr
                85                  90                  95

Tyr Cys Ala Thr Ser Gly Ser Ser Val Leu Tyr Phe Lys Phe Trp Gly
            100                 105                 110

Gln Gly Thr Leu Val Thr Val Ser Ser
        115                 120

<210> SEQ ID NO 2
<211> LENGTH: 25
<212> TYPE: PRT
<213> ORGANISM: artificial sequence
<220> FEATURE:
<223> OTHER INFORMATION: artificial antibody framework region

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 3
<211> LENGTH: 14
<212> TYPE: PRT
<213> ORGANISM: artificial sequence
<220> FEATURE:
<223> OTHER INFORMATION: artificial antibody framework region

<400> SEQUENCE: 3

Trp Val Arg Gln Ala Pro Gly Gln Gly Leu Glu Trp Met Gly
1               5                   10

<210> SEQ ID NO 4
<211> LENGTH: 31
<212> TYPE: PRT
<213> ORGANISM: artificial sequence
<220> FEATURE:
<223> OTHER INFORMATION: artificial antibody framework region

<400> SEQUENCE: 4

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala

-continued

```
                20                  25                  30
```

<210> SEQ ID NO 5
<211> LENGTH: 11
<212> TYPE: PRT
<213> ORGANISM: artificial sequence
<220> FEATURE:
<223> OTHER INFORMATION: artificial antibody framework region

<400> SEQUENCE: 5

```
Trp Gly Gln Gly Thr Leu Val Thr Val Ser Ser
1               5                   10
```

<210> SEQ ID NO 6
<211> LENGTH: 121
<212> TYPE: PRT
<213> ORGANISM: artificial sequence
<220> FEATURE:
<223> OTHER INFORMATION: artificial antibody variable domain

<400> SEQUENCE: 6

```
Gln Val Gln Leu Val Gln Ser Gly Ala Glu Val Lys Lys Pro Gly Ala
1               5                   10                  15

Ser Val Lys Val Ser Cys Lys Ala Ser Gly Ile Asp Phe Asn Ser Asn
            20                  25                  30

Tyr Tyr Met Cys Trp Val Arg Gln Ala Pro Gly Gln Gly Leu Glu Trp
        35                  40                  45

Met Gly Cys Ile Tyr Val Gly Ser His Val Asn Thr Tyr Tyr Ala Asn
    50                  55                  60

Trp Ala Lys Gly Arg Val Thr Met Thr Arg Asp Thr Ser Ile Ser Thr
65                  70                  75                  80

Ala Tyr Met Glu Leu Ser Ser Leu Arg Ser Glu Asp Thr Ala Val Tyr
                85                  90                  95

Tyr Cys Ala Thr Ser Gly Ser Ser Val Leu Tyr Phe Lys Phe Trp Gly
            100                 105                 110

Gln Gly Thr Leu Val Thr Val Ser Ser
        115                 120
```

<210> SEQ ID NO 7
<211> LENGTH: 25
<212> TYPE: PRT
<213> ORGANISM: artificial sequence
<220> FEATURE:
<223> OTHER INFORMATION: artificial antibody framework region

<400> SEQUENCE: 7

```
Gln Val Gln Leu Val Gln Ser Gly Ala Glu Val Lys Lys Pro Gly Ala
1               5                   10                  15

Ser Val Lys Val Ser Cys Lys Ala Ser
            20                  25
```

<210> SEQ ID NO 8
<211> LENGTH: 14
<212> TYPE: PRT
<213> ORGANISM: artificial sequence
<220> FEATURE:
<223> OTHER INFORMATION: artificial antibody framework region

<400> SEQUENCE: 8

```
Trp Val Arg Gln Ala Pro Gly Gln Gly Leu Glu Trp Met Gly
1               5                   10
```

-continued

```
<210> SEQ ID NO 9
<211> LENGTH: 31
<212> TYPE: PRT
<213> ORGANISM: artificial sequence
<220> FEATURE:
<223> OTHER INFORMATION: artificial antibody framework region

<400> SEQUENCE: 9

Arg Val Thr Met Thr Arg Asp Thr Ser Ile Ser Thr Ala Tyr Met Glu
1               5                   10                  15

Leu Ser Ser Leu Arg Ser Glu Asp Thr Ala Val Tyr Tyr Cys Ala
            20                  25                  30

<210> SEQ ID NO 10
<211> LENGTH: 11
<212> TYPE: PRT
<213> ORGANISM: artificial sequence
<220> FEATURE:
<223> OTHER INFORMATION: artificial antibody framework region

<400> SEQUENCE: 10

Trp Gly Gln Gly Thr Leu Val Thr Val Ser Ser
1               5                   10

<210> SEQ ID NO 11
<211> LENGTH: 121
<212> TYPE: PRT
<213> ORGANISM: artificial sequence
<220> FEATURE:
<223> OTHER INFORMATION: artificial antibody variable domain

<400> SEQUENCE: 11

Gln Val Gln Leu Lys Glu Ser Gly Pro Ala Leu Val Lys Pro Thr Gln
1               5                   10                  15

Thr Leu Thr Leu Thr Cys Thr Phe Ser Gly Ile Asp Phe Asn Ser Asn
            20                  25                  30

Tyr Tyr Met Cys Trp Ile Arg Gln Pro Pro Gly Lys Ala Leu Glu Trp
        35                  40                  45

Leu Ala Cys Ile Tyr Val Gly Ser His Val Asn Thr Tyr Tyr Ala Asn
    50                  55                  60

Trp Ala Lys Gly Arg Leu Thr Ile Ser Lys Asp Thr Ser Lys Asn Gln
65                  70                  75                  80

Val Val Leu Thr Met Thr Asn Met Asp Pro Val Asp Thr Ala Thr Tyr
                85                  90                  95

Tyr Cys Ala Thr Ser Gly Ser Ser Val Leu Tyr Phe Lys Phe Trp Gly
            100                 105                 110

Gln Gly Thr Leu Val Thr Val Ser Ser
        115                 120

<210> SEQ ID NO 12
<211> LENGTH: 25
<212> TYPE: PRT
<213> ORGANISM: artificial sequence
<220> FEATURE:
<223> OTHER INFORMATION: artificial antibody framework region

<400> SEQUENCE: 12

Gln Val Gln Leu Lys Glu Ser Gly Pro Ala Leu Val Lys Pro Thr Gln
1               5                   10                  15

Thr Leu Thr Leu Thr Cys Thr Phe Ser
            20                  25
```

```
<210> SEQ ID NO 13
<211> LENGTH: 14
<212> TYPE: PRT
<213> ORGANISM: artificial sequence
<220> FEATURE:
<223> OTHER INFORMATION: artificial antibody framework region

<400> SEQUENCE: 13

Trp Ile Arg Gln Pro Pro Gly Lys Ala Leu Glu Trp Leu Ala
1               5                   10

<210> SEQ ID NO 14
<211> LENGTH: 31
<212> TYPE: PRT
<213> ORGANISM: artificial sequence
<220> FEATURE:
<223> OTHER INFORMATION: artificial antibody framework region

<400> SEQUENCE: 14

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala
            20                  25                  30

<210> SEQ ID NO 15
<211> LENGTH: 11
<212> TYPE: PRT
<213> ORGANISM: artificial sequence
<220> FEATURE:
<223> OTHER INFORMATION: artificial antibody framework region

<400> SEQUENCE: 15

Trp Gly Gln Gly Thr Leu Val Thr Val Ser Ser
1               5                   10

<210> SEQ ID NO 16
<211> LENGTH: 121
<212> TYPE: PRT
<213> ORGANISM: artificial sequence
<220> FEATURE:
<223> OTHER INFORMATION: artificial antibody variable domain

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Asn Ser Asn
            20                  25                  30

Tyr Tyr Met Cys Trp Val Arg Gln Ala Pro Gly Lys Gly Leu Glu Trp
        35                  40                  45

Val Ser Cys Ile Tyr Val Gly Ser His Val Asn Thr Tyr Tyr Ala Asn
    50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Thr Ser Gly Ser Ser Val Leu Tyr Phe Lys Phe Trp Gly
            100                 105                 110

Gln Gly Thr Leu Val Thr Val Ser Ser
        115                 120

<210> SEQ ID NO 17
<211> LENGTH: 25
<212> TYPE: PRT
```

```
<213> ORGANISM: artificial sequence
<220> FEATURE:
<223> OTHER INFORMATION: artificial antibody framework region

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 18
<211> LENGTH: 14
<212> TYPE: PRT
<213> ORGANISM: artificial sequence
<220> FEATURE:
<223> OTHER INFORMATION: artificial antibody framework region

<400> SEQUENCE: 18

Trp Val Arg Gln Ala Pro Gly Lys Gly Leu Glu Trp Val Ser
1               5                   10

<210> SEQ ID NO 19
<211> LENGTH: 31
<212> TYPE: PRT
<213> ORGANISM: artificial sequence
<220> FEATURE:
<223> OTHER INFORMATION: artificial antibody framework region

<400> SEQUENCE: 19

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala
            20                  25                  30

<210> SEQ ID NO 20
<211> LENGTH: 11
<212> TYPE: PRT
<213> ORGANISM: artificial sequence
<220> FEATURE:
<223> OTHER INFORMATION: artificial antibody framework region

<400> SEQUENCE: 20

Trp Gly Gln Gly Thr Leu Val Thr Val Ser Ser
1               5                   10

<210> SEQ ID NO 21
<211> LENGTH: 121
<212> TYPE: PRT
<213> ORGANISM: artificial sequence
<220> FEATURE:
<223> OTHER INFORMATION: artificial antibody variable domain

<400> SEQUENCE: 21

Gln Val Gln Leu Gln Glu Ser Gly Pro Gly Leu Val Lys Pro Ser Glu
1               5                   10                  15

Thr Leu Ser Leu Thr Cys Thr Val Ser Gly Ile Asp Phe Asn Ser Asn
            20                  25                  30

Tyr Tyr Met Cys Trp Ile Arg Gln Pro Pro Gly Lys Gly Leu Glu Trp
        35                  40                  45

Ile Gly Cys Ile Tyr Val Gly Ser His Val Asn Thr Tyr Tyr Ala Asn
    50                  55                  60

Trp Ala Lys Gly Arg Val Thr Ile Ser Val Asp Thr Ser Lys Asn Gln
65                  70                  75                  80
```

```
Phe Ser Leu Lys Leu Ser Ser Val Thr Ala Ala Asp Thr Ala Val Tyr
                85                  90                  95
Tyr Cys Ala Thr Ser Gly Ser Ser Val Leu Tyr Phe Lys Phe Trp Gly
            100                 105                 110
Gln Gly Thr Leu Val Thr Val Ser Ser
        115                 120

<210> SEQ ID NO 22
<211> LENGTH: 25
<212> TYPE: PRT
<213> ORGANISM: artificial sequence
<220> FEATURE:
<223> OTHER INFORMATION: artificial antibody framework region

<400> SEQUENCE: 22

Gln Val Gln Leu Gln Glu Ser Gly Pro Gly Leu Val Lys Pro Ser Glu
1               5                   10                  15
Thr Leu Ser Leu Thr Cys Thr Val Ser
            20                  25

<210> SEQ ID NO 23
<211> LENGTH: 14
<212> TYPE: PRT
<213> ORGANISM: artificial sequence
<220> FEATURE:
<223> OTHER INFORMATION: artificial antibody framework region

<400> SEQUENCE: 23

Trp Ile Arg Gln Pro Pro Gly Lys Gly Leu Glu Trp Ile Gly
1               5                   10

<210> SEQ ID NO 24
<211> LENGTH: 31
<212> TYPE: PRT
<213> ORGANISM: artificial sequence
<220> FEATURE:
<223> OTHER INFORMATION: artificial antibody framework region

<400> SEQUENCE: 24

Arg Val Thr Ile Ser Val Asp Thr Ser Lys Asn Gln Phe Ser Leu Lys
1               5                   10                  15
Leu Ser Ser Val Thr Ala Ala Asp Thr Ala Val Tyr Tyr Cys Ala
            20                  25                  30

<210> SEQ ID NO 25
<211> LENGTH: 11
<212> TYPE: PRT
<213> ORGANISM: artificial sequence
<220> FEATURE:
<223> OTHER INFORMATION: artificial antibody framework region

<400> SEQUENCE: 25

Trp Gly Gln Gly Thr Leu Val Thr Val Ser Ser
1               5                   10

<210> SEQ ID NO 26
<211> LENGTH: 121
<212> TYPE: PRT
<213> ORGANISM: artificial sequence
<220> FEATURE:
<223> OTHER INFORMATION: artificial antibody variable domain

<400> SEQUENCE: 26

Gln Val Gln Leu Gln Glu Ser Gly Pro Gly Leu Val Lys Pro Ser Glu
1               5                   10                  15
```

```
Thr Leu Ser Leu Thr Cys Lys Val Ser Gly Ile Asp Phe Asn Ser Asn
            20                  25                  30

Tyr Tyr Met Cys Trp Ile Arg Gln Pro Pro Gly Lys Gly Leu Glu Trp
        35                  40                  45

Ile Gly Cys Ile Tyr Val Gly Ser His Val Asn Thr Tyr Tyr Ala Asn
 50                  55                  60

Trp Ala Lys Gly Arg Val Thr Ile Ser Val Asp Ser Ser Lys Asn Gln
 65                  70                  75                  80

Phe Ser Leu Lys Leu Ser Ser Val Thr Ala Ala Asp Thr Ala Val Tyr
                85                  90                  95

Tyr Cys Ala Thr Ser Gly Ser Ser Val Leu Tyr Phe Lys Phe Trp Gly
            100                 105                 110

Gln Gly Thr Leu Val Thr Val Ser Ser
        115                 120
```

<210> SEQ ID NO 27
<211> LENGTH: 25
<212> TYPE: PRT
<213> ORGANISM: artificial sequence
<220> FEATURE:
<223> OTHER INFORMATION: artificial antibody framework region

<400> SEQUENCE: 27

```
Gln Val Gln Leu Gln Glu Ser Gly Pro Gly Leu Val Lys Pro Ser Glu
 1               5                  10                  15

Thr Leu Ser Leu Thr Cys Lys Val Ser
            20                  25
```

<210> SEQ ID NO 28
<211> LENGTH: 14
<212> TYPE: PRT
<213> ORGANISM: artificial sequence
<220> FEATURE:
<223> OTHER INFORMATION: artificial antibody framework region

<400> SEQUENCE: 28

```
Trp Ile Arg Gln Pro Pro Gly Lys Gly Leu Glu Trp Ile Gly
 1               5                  10
```

<210> SEQ ID NO 29
<211> LENGTH: 31
<212> TYPE: PRT
<213> ORGANISM: artificial sequence
<220> FEATURE:
<223> OTHER INFORMATION: artificial antibody framework region

<400> SEQUENCE: 29

```
Arg Val Thr Ile Ser Val Asp Ser Ser Lys Asn Gln Phe Ser Leu Lys
 1               5                  10                  15

Leu Ser Ser Val Thr Ala Ala Asp Thr Ala Val Tyr Tyr Cys Ala
            20                  25                  30
```

<210> SEQ ID NO 30
<211> LENGTH: 11
<212> TYPE: PRT
<213> ORGANISM: artificial sequence
<220> FEATURE:
<223> OTHER INFORMATION: artificial antibody framework region

<400> SEQUENCE: 30

```
Trp Gly Gln Gly Thr Leu Val Thr Val Ser Ser
 1               5                  10
```

<210> SEQ ID NO 31
<211> LENGTH: 121
<212> TYPE: PRT
<213> ORGANISM: artificial sequence
<220> FEATURE:
<223> OTHER INFORMATION: artificial antibody variable domain

<400> SEQUENCE: 31

Glu Val Gln Leu Val Gln Ser Gly Ala Glu Val Lys Lys Pro Gly Glu
1               5                   10                  15

Ser Leu Lys Ile Ser Cys Lys Gly Ser Gly Ile Asp Phe Asn Ser Asn
            20                  25                  30

Tyr Tyr Met Cys Trp Val Arg Gln Met Pro Gly Lys Gly Leu Glu Trp
        35                  40                  45

Met Gly Cys Ile Tyr Val Gly Ser His Val Asn Thr Tyr Tyr Ala Asn
    50                  55                  60

Trp Ala Lys Gly Gln Val Thr Ile Ser Ala Asp Lys Ser Ile Ser Thr
65                  70                  75                  80

Ala Tyr Leu Gln Trp Ser Ser Leu Lys Ala Ser Asp Thr Ala Met Tyr
                85                  90                  95

Tyr Cys Ala Thr Ser Gly Ser Ser Val Leu Tyr Phe Lys Phe Trp Gly
            100                 105                 110

Gln Gly Thr Leu Val Thr Val Ser Ser
        115                 120

<210> SEQ ID NO 32
<211> LENGTH: 25
<212> TYPE: PRT
<213> ORGANISM: artificial sequence
<220> FEATURE:
<223> OTHER INFORMATION: artificial antibody framework region

<400> SEQUENCE: 32

Glu Val Gln Leu Val Gln Ser Gly Ala Glu Val Lys Lys Pro Gly Glu
1               5                   10                  15

Ser Leu Lys Ile Ser Cys Lys Gly Ser
            20                  25

<210> SEQ ID NO 33
<211> LENGTH: 18
<212> TYPE: PRT
<213> ORGANISM: artificial sequence
<220> FEATURE:
<223> OTHER INFORMATION: artificial antibody framework region

<400> SEQUENCE: 33

Cys Ile Tyr Val Gly Ser His Val Asn Thr Tyr Tyr Ala Asn Trp Ala
1               5                   10                  15

Lys Gly

<210> SEQ ID NO 34
<211> LENGTH: 31
<212> TYPE: PRT
<213> ORGANISM: artificial sequence
<220> FEATURE:
<223> OTHER INFORMATION: artificial antibody framework region

<400> SEQUENCE: 34

Gln Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala
            20                  25                  30

<210> SEQ ID NO 35
<211> LENGTH: 11
<212> TYPE: PRT
<213> ORGANISM: artificial sequence
<220> FEATURE:
<223> OTHER INFORMATION: artificial antibody framework region

<400> SEQUENCE: 35

Trp Gly Gln Gly Thr Leu Val Thr Val Ser Ser
1               5                   10

<210> SEQ ID NO 36
<211> LENGTH: 121
<212> TYPE: PRT
<213> ORGANISM: artificial sequence
<220> FEATURE:
<223> OTHER INFORMATION: artificial antibody variable domain

<400> SEQUENCE: 36

Gln Val Gln Leu Gln Gln Ser Gly Pro Gly Leu Val Lys Pro Ser Gln
1               5                   10                  15

Thr Leu Ser Leu Thr Cys Ala Ile Ser Gly Ile Asp Phe Asn Ser Asn
            20                  25                  30

Tyr Tyr Met Cys Trp Ile Arg Gln Ser Pro Gly Arg Gly Leu Glu Trp
        35                  40                  45

Leu Gly Cys Ile Tyr Val Gly Ser His Val Asn Thr Tyr Tyr Ala Asn
    50                  55                  60

Trp Ala Lys Gly Arg Ile Thr Ile Asn Pro Asp Thr Ser Lys Asn Gln
65                  70                  75                  80

Phe Ser Leu Gln Leu Asn Ser Val Thr Pro Glu Asp Thr Ala Val Tyr
                85                  90                  95

Tyr Cys Ala Thr Ser Gly Ser Ser Val Leu Tyr Phe Lys Phe Trp Gly
            100                 105                 110

Gln Gly Thr Leu Val Thr Val Ser Ser
        115                 120

<210> SEQ ID NO 37
<211> LENGTH: 25
<212> TYPE: PRT
<213> ORGANISM: artificial sequence
<220> FEATURE:
<223> OTHER INFORMATION: artificial antibody framework region

<400> SEQUENCE: 37

Gln Val Gln Leu Gln Gln Ser Gly Pro Gly Leu Val Lys Pro Ser Gln
1               5                   10                  15

Thr Leu Ser Leu Thr Cys Ala Ile Ser
            20                  25

<210> SEQ ID NO 38
<211> LENGTH: 14
<212> TYPE: PRT
<213> ORGANISM: artificial sequence
<220> FEATURE:
<223> OTHER INFORMATION: artificial antibody framework region

<400> SEQUENCE: 38

Trp Ile Arg Gln Ser Pro Gly Arg Gly Leu Glu Trp Leu Gly
1               5                   10

```
<210> SEQ ID NO 39
<211> LENGTH: 31
<212> TYPE: PRT
<213> ORGANISM: artificial sequence
<220> FEATURE:
<223> OTHER INFORMATION: artificial antibody framework region

<400> SEQUENCE: 39

Arg Ile Thr Ile Asn Pro Asp Thr Ser Lys Asn Gln Phe Ser Leu Gln
1               5                   10                  15

Leu Asn Ser Val Thr Pro Glu Asp Thr Ala Val Tyr Tyr Cys Ala
            20                  25                  30

<210> SEQ ID NO 40
<211> LENGTH: 11
<212> TYPE: PRT
<213> ORGANISM: artificial sequence
<220> FEATURE:
<223> OTHER INFORMATION: artificial antibody framework region

<400> SEQUENCE: 40

Trp Gly Gln Gly Thr Leu Val Thr Val Ser Ser
1               5                   10

<210> SEQ ID NO 41
<211> LENGTH: 113
<212> TYPE: PRT
<213> ORGANISM: artificial sequence
<220> FEATURE:
<223> OTHER INFORMATION: artificial antibody variable domain

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Gln Gly Thr Lys Val Glu Ile Lys
            100                 105                 110

Arg

<210> SEQ ID NO 42
<211> LENGTH: 23
<212> TYPE: PRT
<213> ORGANISM: artificial sequence
<220> FEATURE:
<223> OTHER INFORMATION: artificial antibody framework region

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys
            20
```

```
<210> SEQ ID NO 43
<211> LENGTH: 15
<212> TYPE: PRT
<213> ORGANISM: artificial sequence
<220> FEATURE:
<223> OTHER INFORMATION: artificial antibody framework region

<400> SEQUENCE: 43

Trp Tyr Gln Gln Lys Pro Gly Lys Ala Pro Lys Leu Leu Ile Tyr
1               5                   10                  15

<210> SEQ ID NO 44
<211> LENGTH: 32
<212> TYPE: PRT
<213> ORGANISM: artificial sequence
<220> FEATURE:
<223> OTHER INFORMATION: artificial antibody framework region

<400> SEQUENCE: 44

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 45
<211> LENGTH: 11
<212> TYPE: PRT
<213> ORGANISM: artificial sequence
<220> FEATURE:
<223> OTHER INFORMATION: artificial antibody framework region

<400> SEQUENCE: 45

Phe Gly Gln Gly Thr Lys Val Glu Ile Lys Arg
1               5                   10

<210> SEQ ID NO 46
<211> LENGTH: 113
<212> TYPE: PRT
<213> ORGANISM: artificial sequence
<220> FEATURE:
<223> OTHER INFORMATION: artificial antibody variable domain

<400> SEQUENCE: 46

Asp Ile Val Met Thr Gln Ser Pro Leu Ser Leu Pro Val Thr Pro Gly
1               5                   10                  15

Glu Pro Ala Ser Ile Ser Cys Gln Ala Ser Glu Asn Ile Tyr Ser Phe
            20                  25                  30

Leu Ala Trp Tyr Leu Gln Lys Pro Gly Gln Ser Pro Gln Leu Leu Ile
        35                  40                  45

Tyr Ser Ala Ser Lys Leu Ala Ala Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Gln Thr Asn Arg Tyr Ser Asn
                85                  90                  95

Pro Asp Ile Tyr Asn Val Phe Gly Gln Gly Thr Lys Val Glu Ile Lys
            100                 105                 110

Arg

<210> SEQ ID NO 47
<211> LENGTH: 23
<212> TYPE: PRT
<213> ORGANISM: artificial sequence
```

<220> FEATURE:
<223> OTHER INFORMATION: artificial antibody framework region

<400> SEQUENCE: 47

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 48
<211> LENGTH: 15
<212> TYPE: PRT
<213> ORGANISM: artificial sequence
<220> FEATURE:
<223> OTHER INFORMATION: artificial antibody framework region

<400> SEQUENCE: 48

Trp Tyr Leu Gln Lys Pro Gly Gln Ser Pro Gln Leu Leu Ile Tyr
1               5                   10                  15

<210> SEQ ID NO 49
<211> LENGTH: 32
<212> TYPE: PRT
<213> ORGANISM: artificial sequence
<220> FEATURE:
<223> OTHER INFORMATION: artificial antibody framework region

<400> SEQUENCE: 49

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 50
<211> LENGTH: 11
<212> TYPE: PRT
<213> ORGANISM: artificial sequence
<220> FEATURE:
<223> OTHER INFORMATION: artificial antibody framework region

<400> SEQUENCE: 50

Phe Gly Gln Gly Thr Lys Val Glu Ile Lys Arg
1               5                   10

<210> SEQ ID NO 51
<211> LENGTH: 113
<212> TYPE: PRT
<213> ORGANISM: artificial sequence
<220> FEATURE:
<223> OTHER INFORMATION: artificial antibody variable domain

<400> SEQUENCE: 51

Asp Ile Val Leu Thr Gln Ser Pro Ala Thr Leu Ser Leu Ser Pro Gly
1               5                   10                  15

Glu Arg Ala Thr Leu Ser Cys Gln Ala Ser Gln Asn Ile Tyr Ser Phe
            20                  25                  30

Leu Ala Trp Tyr Gln Gln Lys Pro Gly Gln Ala Pro Arg Leu Leu Ile
        35                  40                  45

Tyr Ser Ala Ser Lys Leu Ala Ala Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Thr Asn Arg Tyr Ser Asn

```
                  85                  90                  95

Pro Asp Ile Tyr Asn Val Phe Gly Gln Gly Thr Lys Val Glu Ile Lys
                 100                 105                 110

Arg

<210> SEQ ID NO 52
<211> LENGTH: 23
<212> TYPE: PRT
<213> ORGANISM: artificial sequence
<220> FEATURE:
<223> OTHER INFORMATION: artificial antibody framework region

<400> SEQUENCE: 52

Asp Ile Val Leu Thr Gln Ser Pro Ala Thr Leu Ser Leu Ser Pro Gly
1               5                  10                  15

Glu Arg Ala Thr Leu Ser Cys
            20

<210> SEQ ID NO 53
<211> LENGTH: 15
<212> TYPE: PRT
<213> ORGANISM: artificial sequence
<220> FEATURE:
<223> OTHER INFORMATION: artificial antibody framework region

<400> SEQUENCE: 53

Trp Tyr Gln Gln Lys Pro Gly Gln Ala Pro Arg Leu Leu Ile Tyr
1               5                  10                  15

<210> SEQ ID NO 54
<211> LENGTH: 32
<212> TYPE: PRT
<213> ORGANISM: artificial sequence
<220> FEATURE:
<223> OTHER INFORMATION: artificial antibody framework region

<400> SEQUENCE: 54

Gly Val Pro Ala Arg Phe Ser Gly Ser Gly Ser Gly Thr Asp Phe Thr
1               5                  10                  15

Leu Thr Ile Ser Ser Leu Glu Pro Glu Asp Phe Ala Val Tyr Tyr Cys
            20                  25                  30

<210> SEQ ID NO 55
<211> LENGTH: 11
<212> TYPE: PRT
<213> ORGANISM: artificial sequence
<220> FEATURE:
<223> OTHER INFORMATION: artificial antibody framework region

<400> SEQUENCE: 55

Phe Gly Gln Gly Thr Lys Val Glu Ile Lys Arg
1               5                  10

<210> SEQ ID NO 56
<211> LENGTH: 113
<212> TYPE: PRT
<213> ORGANISM: artificial sequence
<220> FEATURE:
<223> OTHER INFORMATION: artificial antibody variable domain

<400> SEQUENCE: 56

Asp Ile Gln Met Thr Gln Ser Pro Ser Ser Leu Ser Ala Ser Val Gly
1               5                  10                  15

Asp Arg Val Thr Ile Thr Cys Gln Ala Ser Glu Asn Ile Tyr Ser Phe
```

```
                     20                  25                  30

Leu Ala Trp Tyr Gln Gln Lys Pro Gly Lys Ala Pro Lys Leu Leu Ile
            35                  40                  45

Tyr Ser Ala Ser Lys Leu Ala Ala Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Gly Gly Thr Lys Leu Thr Val Leu
            100                 105                 110

Gly

<210> SEQ ID NO 57
<211> LENGTH: 113
<212> TYPE: PRT
<213> ORGANISM: artificial sequence
<220> FEATURE:
<223> OTHER INFORMATION: artificial antibody variable domain

<400> SEQUENCE: 57

Asp Ile Gln Met Thr Gln Ser Pro Ser Ser Leu Ser Ala Ser Val Gly
 1               5                  10                  15

Asp Arg Val Thr Ile Thr Cys Gln Ala Ser Glu Asn Ile Tyr Ser Phe
                20                  25                  30

Leu Ala Trp Tyr Gln Gln Lys Pro Gly Lys Ala Pro Lys Leu Leu Ile
            35                  40                  45

Tyr Ser Ala Ser Lys Leu Ala Ala Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Thr Gly Thr Lys Val Thr Val Leu
            100                 105                 110

Gly

<210> SEQ ID NO 58
<211> LENGTH: 113
<212> TYPE: PRT
<213> ORGANISM: artificial sequence
<220> FEATURE:
<223> OTHER INFORMATION: artificial antibody variable domain

<400> SEQUENCE: 58

Asp Ile Val Met Thr Gln Ser Pro Leu Ser Leu Pro Val Thr Pro Gly
 1               5                  10                  15

Glu Pro Ala Ser Ile Ser Cys Gln Ala Ser Glu Asn Ile Tyr Ser Phe
                20                  25                  30

Leu Ala Trp Tyr Leu Gln Lys Pro Gly Gln Ser Pro Gln Leu Leu Ile
            35                  40                  45

Tyr Ser Ala Ser Lys Leu Ala Ala Gly Val Pro Asp Arg Phe Ser Gly
        50                  55                  60

Ser Gly Ser Gly Thr Asp Phe Thr Leu Lys Ile Ser Arg Val Glu Ala
 65                  70                  75                  80

Glu Asp Val Gly Val Tyr Tyr Cys Gln Gln Thr Asn Arg Tyr Ser Asn
                85                  90                  95
```

```
Pro Asp Ile Tyr Asn Val Phe Gly Gly Gly Thr Lys Leu Thr Val Leu
            100                 105                 110

Gly

<210> SEQ ID NO 59
<211> LENGTH: 113
<212> TYPE: PRT
<213> ORGANISM: artificial sequence
<220> FEATURE:
<223> OTHER INFORMATION: artificial antibody variable domain

<400> SEQUENCE: 59

Asp Ile Val Met Thr Gln Ser Pro Leu Ser Leu Pro Val Thr Pro Gly
1               5                   10                  15

Glu Pro Ala Ser Ile Ser Cys Gln Ala Ser Glu Asn Ile Tyr Ser Phe
            20                  25                  30

Leu Ala Trp Tyr Leu Gln Lys Pro Gly Gln Ser Pro Gln Leu Leu Ile
        35                  40                  45

Tyr Ser Ala Ser Lys Leu Ala Ala Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Gln Thr Asn Arg Tyr Ser Asn
                85                  90                  95

Pro Asp Ile Tyr Asn Val Phe Gly Thr Gly Thr Lys Val Thr Val Leu
            100                 105                 110

Gly

<210> SEQ ID NO 60
<211> LENGTH: 113
<212> TYPE: PRT
<213> ORGANISM: artificial sequence
<220> FEATURE:
<223> OTHER INFORMATION: artificial antibody variable domain

<400> SEQUENCE: 60

Asp Ile Val Leu Thr Gln Ser Pro Ala Thr Leu Ser Leu Ser Pro Gly
1               5                   10                  15

Glu Arg Ala Thr Leu Ser Cys Gln Ala Ser Glu Asn Ile Tyr Ser Phe
            20                  25                  30

Leu Ala Trp Tyr Gln Gln Lys Pro Gly Gln Ala Pro Arg Leu Leu Ile
        35                  40                  45

Tyr Ser Ala Ser Lys Leu Ala Ala Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Thr Asn Arg Tyr Ser Asn
                85                  90                  95

Pro Asp Ile Tyr Asn Val Phe Gly Gly Gly Thr Lys Leu Thr Val Leu
            100                 105                 110

Gly

<210> SEQ ID NO 61
<211> LENGTH: 113
<212> TYPE: PRT
<213> ORGANISM: artificial sequence
<220> FEATURE:
<223> OTHER INFORMATION: artificial antibody variable domain
```

<400> SEQUENCE: 61

Asp Ile Val Leu Thr Gln Ser Pro Ala Thr Leu Ser Leu Ser Pro Gly
1               5                   10                  15

Glu Arg Ala Thr Leu Ser Cys Gln Ala Ser Glu Asn Ile Tyr Ser Phe
            20                  25                  30

Leu Ala Trp Tyr Gln Gln Lys Pro Gly Gln Ala Pro Arg Leu Leu Ile
        35                  40                  45

Tyr Ser Ala Ser Lys Leu Ala Ala Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Thr Asn Arg Tyr Ser Asn
                85                  90                  95

Pro Asp Ile Tyr Asn Val Phe Gly Thr Gly Thr Lys Val Thr Val Leu
            100                 105                 110

Gly

<210> SEQ ID NO 62
<211> LENGTH: 11
<212> TYPE: PRT
<213> ORGANISM: artificial sequence
<220> FEATURE:
<223> OTHER INFORMATION: artificial antibody framework region

<400> SEQUENCE: 62

Phe Gly Gly Gly Thr Lys Leu Thr Val Leu Gly
1               5                   10

<210> SEQ ID NO 63
<211> LENGTH: 11
<212> TYPE: PRT
<213> ORGANISM: artificial sequence
<220> FEATURE:
<223> OTHER INFORMATION: artificial antibody framework region

<400> SEQUENCE: 63

Phe Gly Thr Gly Thr Lys Val Thr Val Leu Gly
1               5                   10

<210> SEQ ID NO 64
<211> LENGTH: 20
<212> TYPE: PRT
<213> ORGANISM: artificial sequence
<220> FEATURE:
<223> OTHER INFORMATION: artificial linker sequence

<400> SEQUENCE: 64

Gly Gly Gly Gly Ser Gly Gly Gly Ser Gly Gly Gly Ser Gly
1               5                   10                  15

Gly Gly Gly Ser
            20

<210> SEQ ID NO 65
<211> LENGTH: 15
<212> TYPE: PRT
<213> ORGANISM: artificial sequence
<220> FEATURE:
<223> OTHER INFORMATION: artificial linker sequence

<400> SEQUENCE: 65

Gly Gly Gly Gly Ser Gly Gly Gly Gly Ser Gly Gly Gly Gly Ser

<210> SEQ ID NO 66
<211> LENGTH: 11
<212> TYPE: PRT
<213> ORGANISM: artificial sequence
<220> FEATURE:
<223> OTHER INFORMATION: artificial antibody CDR sequence

<400> SEQUENCE: 66

Gln Ala Ser Glu Asn Ile Tyr Ser Phe Leu Ala
1               5                   10

<210> SEQ ID NO 67
<211> LENGTH: 7
<212> TYPE: PRT
<213> ORGANISM: artificial sequence
<220> FEATURE:
<223> OTHER INFORMATION: artificial antibody CDR sequence

<400> SEQUENCE: 67

Ser Ala Ser Lys Leu Ala Ala
1               5

<210> SEQ ID NO 68
<211> LENGTH: 14
<212> TYPE: PRT
<213> ORGANISM: artificial sequence
<220> FEATURE:
<223> OTHER INFORMATION: artificial antibody CDR sequence

<400> SEQUENCE: 68

Gln Gln Thr Asn Arg Tyr Ser Asn Pro Asp Ile Tyr Asn Val
1               5                   10

<210> SEQ ID NO 69
<211> LENGTH: 11
<212> TYPE: PRT
<213> ORGANISM: artificial sequence
<220> FEATURE:
<223> OTHER INFORMATION: artificial antibody CDR sequence

<400> SEQUENCE: 69

Gly Ile Asp Phe Asn Ser Asn Tyr Tyr Met Cys
1               5                   10

<210> SEQ ID NO 70
<211> LENGTH: 18
<212> TYPE: PRT
<213> ORGANISM: artificial sequence
<220> FEATURE:
<223> OTHER INFORMATION: artificial antibody CDR sequence

<400> SEQUENCE: 70

Cys Ile Tyr Val Gly Ser His Val Asn Thr Tyr Tyr Ala Asn Trp Ala
1               5                   10                  15

Lys Gly

<210> SEQ ID NO 71
<211> LENGTH: 11
<212> TYPE: PRT
<213> ORGANISM: artificial sequence
<220> FEATURE:
<223> OTHER INFORMATION: artificial antibody CDR sequence

<400> SEQUENCE: 71

Thr Ser Gly Ser Ser Val Leu Tyr Phe Lys Phe
1               5                   10

<210> SEQ ID NO 72
<211> LENGTH: 11
<212> TYPE: PRT
<213> ORGANISM: artificial sequence
<220> FEATURE:
<223> OTHER INFORMATION: artificial antibody CDR sequence

<400> SEQUENCE: 72

Gln Ala Ser Gln Ser Ile Ser Asp Trp Leu Ala
1               5                   10

<210> SEQ ID NO 73
<211> LENGTH: 7
<212> TYPE: PRT
<213> ORGANISM: artificial sequence
<220> FEATURE:
<223> OTHER INFORMATION: artificial antibody CDR sequence

<400> SEQUENCE: 73

Gly Ala Ser Arg Leu Ala Ser
1               5

<210> SEQ ID NO 74
<211> LENGTH: 12
<212> TYPE: PRT
<213> ORGANISM: artificial sequence
<220> FEATURE:
<223> OTHER INFORMATION: artificial antibody CDR sequence

<400> SEQUENCE: 74

Gln Gln Gly Trp Ser Asp Ser Tyr Val Asp Asn Leu
1               5                   10

<210> SEQ ID NO 75
<211> LENGTH: 10
<212> TYPE: PRT
<213> ORGANISM: artificial sequence
<220> FEATURE:
<223> OTHER INFORMATION: artificial antibody CDR sequence

<400> SEQUENCE: 75

Gly Phe Ser Leu Ser Ser Gly Ala Met Ser
1               5                   10

<210> SEQ ID NO 76
<211> LENGTH: 16
<212> TYPE: PRT
<213> ORGANISM: artificial sequence
<220> FEATURE:
<223> OTHER INFORMATION: artificial antibody CDR sequence

<400> SEQUENCE: 76

Val Ile Ile Ser Ser Gly Ala Thr Tyr Tyr Ala Ser Trp Ala Lys Gly
1               5                   10                  15

<210> SEQ ID NO 77
<211> LENGTH: 15
<212> TYPE: PRT
<213> ORGANISM: artificial sequence
<220> FEATURE:
<223> OTHER INFORMATION: artificial antibody CDR sequence

<400> SEQUENCE: 77

Arg Gly Gly Pro Asp Asp Ser Asn Ser Met Gly Thr Phe Asp Pro

<210> SEQ ID NO 78
<211> LENGTH: 122
<212> TYPE: PRT
<213> ORGANISM: artificial sequence
<220> FEATURE:
<223> OTHER INFORMATION: artificial antibody variable domain

<400> SEQUENCE: 78

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Leu Ser Ser Gly
            20                  25                  30

Ala Met Ser Trp Ile Arg Gln Pro Pro Gly Lys Gly Leu Glu Trp Ile
        35                  40                  45

Gly Val Ile Ile Ser Ser Gly Ala Thr Tyr Tyr Ala Ser Trp Ala Lys
    50                  55                  60

Gly Arg Val Thr Ile Ser Val Asp Ser Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Pro Asp Asp Ser Asn Ser Met Gly Thr Phe Asp Pro Trp
            100                 105                 110

Gly Gln Gly Thr Leu Val Thr Val Ser Ser
        115                 120

<210> SEQ ID NO 79
<211> LENGTH: 11
<212> TYPE: PRT
<213> ORGANISM: artificial sequence
<220> FEATURE:
<223> OTHER INFORMATION: artificial antibody framework region

<400> SEQUENCE: 79

Phe Gly Cys Gly Thr Lys Leu Thr Val Leu Gly
1               5                   10

<210> SEQ ID NO 80
<211> LENGTH: 11
<212> TYPE: PRT
<213> ORGANISM: artificial sequence
<220> FEATURE:
<223> OTHER INFORMATION: artificial antibody framework region

<400> SEQUENCE: 80

Phe Gly Cys Gly Thr Lys Val Thr Val Leu Gly
1               5                   10

<210> SEQ ID NO 81
<211> LENGTH: 113
<212> TYPE: PRT
<213> ORGANISM: artificial sequence
<220> FEATURE:
<223> OTHER INFORMATION: artificial antibody variable domain

<400> SEQUENCE: 81

Asp Ile Val Met Thr Gln Ser Pro Asp Ser Leu Ala Val Ser Leu Gly
1               5                   10                  15

Glu Arg Ala Thr Ile Asn Cys Gln Ala Ser Glu Asn Ile Tyr Ser Phe
            20                  25                  30

Leu Ala Trp Tyr Gln Gln Lys Pro Gly Gln Pro Pro Lys Leu Leu Ile

```
                35                  40                  45
Tyr Ser Ala Ser Lys Leu Ala Ala Gly Val Pro Asp Arg Phe Ser Gly
 50                  55                  60
Ser Gly Ser Gly Thr Asp Phe Thr Leu Thr Ile Ser Ser Leu Gln Ala
65                  70                  75                  80
Glu Asp Val Ala Val Tyr Tyr Cys Gln Gln Thr Asn Arg Tyr Ser Asn
                85                  90                  95
Pro Asp Ile Tyr Asn Val Phe Gly Gln Gly Thr Lys Val Glu Ile Lys
                100                 105                 110
Arg

<210> SEQ ID NO 82
<211> LENGTH: 111
<212> TYPE: PRT
<213> ORGANISM: artificial sequence
<220> FEATURE:
<223> OTHER INFORMATION: artificial antibody variable domain

<400> SEQUENCE: 82

Asp Ile Gln Met Thr Gln Ser Pro Ser Ser Leu Ser Ala Ser Val Gly
1               5                   10                  15
Asp Arg Val Thr Ile Thr Cys Gln Ala Ser Gln Ser Ile Ser Asp Trp
                20                  25                  30
Leu Ala Trp Tyr Gln Gly Lys Pro Gly Lys Ala Pro Lys Leu Leu Ile
                35                  40                  45
Tyr Gly Ala Ser Arg Leu Ala Ser Gly Val Pro Ser Arg Phe Ser Gly
 50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Gly Trp Ser Asp Ser Tyr
                85                  90                  95
Val Asp Asn Leu Phe Gly Gly Gly Thr Lys Leu Thr Val Leu Gly
                100                 105                 110

<210> SEQ ID NO 83
<211> LENGTH: 122
<212> TYPE: PRT
<213> ORGANISM: artificial sequence
<220> FEATURE:
<223> OTHER INFORMATION: artificial antibody variable domain

<400> SEQUENCE: 83

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Ser Leu Ser Ser Gly
                20                  25                  30
Ala Met Ser Trp Val Arg Gln Ala Pro Gly Lys Gly Leu Glu Trp Val
                35                  40                  45
Ser Val Ile Ile Ser Ser Gly Ala Thr Tyr Tyr Ala Ser Trp Ala Lys
 50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                85                  90                  95
Arg Gly Gly Pro Asp Asp Ser Asn Ser Met Gly Thr Phe Asp Pro Trp
                100                 105                 110
Gly Gln Gly Thr Leu Val Thr Val Ser Ser
```

```
                      115                 120

<210> SEQ ID NO 84
<211> LENGTH: 122
<212> TYPE: PRT
<213> ORGANISM: artificial sequence
<220> FEATURE:
<223> OTHER INFORMATION: artificial antibody variable domain

<400> SEQUENCE: 84

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Gly
            20                  25                  30

Ala Met Ser Trp Ile Arg Gln Pro Pro Gly Lys Gly Leu Glu Trp Ile
        35                  40                  45

Gly Val Ile Ile Ser Ser Gly Ala Thr Tyr Tyr Ala Ser Trp Ala Lys
    50                  55                  60

Gly Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Pro Asp Asp Ser Asn Ser Met Gly Thr Phe Asp Pro Trp
            100                 105                 110

Gly Gln Gly Thr Leu Val Thr Val Ser Ser
        115                 120

<210> SEQ ID NO 85
<211> LENGTH: 111
<212> TYPE: PRT
<213> ORGANISM: artificial sequence
<220> FEATURE:
<223> OTHER INFORMATION: artificial antibody variable domain

<400> SEQUENCE: 85

Asp Ile Val Leu Thr Gln Ser Pro Ala Thr Leu Ser Leu Ser Pro Gly
1               5                   10                  15

Glu Arg Ala Thr Leu Ser Cys Gln Ala Ser Gln Ser Ile Ser Asp Trp
            20                  25                  30

Leu Ala Trp Tyr Gln Gln Lys Pro Gly Gln Ala Pro Arg Leu Leu Ile
        35                  40                  45

Tyr Gly Ala Ser Arg Leu Ala Ser Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Trp Ser Asp Ser Tyr
                85                  90                  95

Val Asp Asn Leu Phe Gly Gly Gly Thr Lys Leu Thr Val Leu Gly
            100                 105                 110
```